United States Patent
Fernandez Rodriguez et al.

(10) Patent No.: US 12,098,372 B2
(45) Date of Patent: Sep. 24, 2024

(54) MICROBIOME MODULATION OF A HOST BY DELIVERY OF DNA PAYLOADS WITH MINIMIZED SPREAD

(71) Applicant: Eligo Bioscience, Paris (FR)

(72) Inventors: Jesus Fernandez Rodriguez, Paris (FR); Xavier Duportet, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 18/348,929

(22) Filed: Jul. 7, 2023

(65) Prior Publication Data

US 2024/0102026 A1    Mar. 28, 2024

Related U.S. Application Data

(60) Division of application No. 17/565,060, filed on Dec. 29, 2021, now Pat. No. 11,746,352, which is a continuation-in-part of application No. 17/138,084, filed on Dec. 30, 2020, now abandoned, and a continuation-in-part of application No. PCT/EP2020/088043, filed on Dec. 30, 2020.

(60) Provisional application No. 63/132,090, filed on Dec. 30, 2020, provisional application No. 63/132,190, filed on Dec. 30, 2020, provisional application No. 63/137,989, filed on Jan. 15, 2021, provisional application No. 62/955,278, filed on Dec. 30, 2019.

(51) Int. Cl.
| | |
|---|---|
| C12N 15/74 | (2006.01) |
| C12N 15/113 | (2010.01) |
| C12N 15/70 | (2006.01) |
| A61K 48/00 | (2006.01) |

(52) U.S. Cl.
CPC .......... *C12N 15/70* (2013.01); *C12N 15/113* (2013.01)

(58) Field of Classification Search
CPC .............................. C12N 15/70; C12N 15/113
See application file for complete search history.

(56) References Cited

U.S. PATENT DOCUMENTS

| | | | |
|---|---|---|---|
| 4,920,048 | A | 4/1990 | Diderichsen |
| 5,691,185 | A | 11/1997 | Dickely et al. |
| 5,863,560 | A | 1/1999 | Osborne |
| 6,291,245 | B1 | 9/2001 | Kopetzki et al. |
| 6,413,768 | B1 | 7/2002 | Galen |
| 6,752,994 | B2 | 6/2004 | Jacobs, Jr. et al. |
| 7,338,800 | B2 | 3/2008 | Elledge |
| 10,113,163 | B2 | 10/2018 | Liu et al. |
| 11,224,621 | B2 | 1/2022 | Duportet |
| 2005/0096286 | A1 | 5/2005 | Caron et al. |
| 2005/0186666 | A1 | 8/2005 | Schneider et al. |
| 2011/0218216 | A1 | 9/2011 | Mvek et al. |
| 2015/0064138 | A1 | 3/2015 | Lu et al. |
| 2015/0166980 | A1 | 6/2015 | Liu et al. |
| 2018/0155729 | A1 | 6/2018 | Beisel et al. |
| 2020/0254035 | A1 | 8/2020 | Haaber |

FOREIGN PATENT DOCUMENTS

| | | |
|---|---|---|
| WO | 2014/124226 A1 | 8/2014 |
| WO | 2016/141108 A1 | 9/2016 |
| WO | 2017/075485 A1 | 5/2017 |
| WO | 2017/141173 A2 | 8/2017 |
| WO | 2018/236548 A1 | 12/2018 |
| WO | 2020/181178 A1 | 9/2020 |
| WO | 2020/181180 A1 | 9/2020 |
| WO | 2020/181193 A1 | 9/2020 |
| WO | 2020/181195 A1 | 9/2020 |
| WO | 2020/181202 A1 | 9/2020 |
| WO | 2021/204967 A1 | 10/2021 |
| WO | 2021/250284 A1 | 12/2021 |

OTHER PUBLICATIONS

Kiga et al. Development of CRISPR-Cas13a-based antimicrobials capable of sequence-specific killing of target bacteria. Nature Communications 11:2934; doi.org/10.1038/s41467-020-16731-6, 11 pages; (Year: 2020).*
Ram et al. Conversion of staphylococcal pathogenicity islands to CRISPR-carrying antibacterial agents that cure infections in mice. Nature Biotechnology 36:971-976 plus 2 pages of Online Methods; (Year: 2018).*
Abudayyeh et al. RNA targeting with CRISPR-Cas13a. Nature. Oct. 12, 2017; 550(7675): 280-284.
Anzalone et al. Search-and-replace genome editing without double-strand breaks or donor DNA. Nature. Dec. 2019 ; 576(7785): 149-157.
Cambray et al. Measurement and modeling of intrinsic transcription terminators. Nucleic Acids Research, 2013, vol. 41, No. 9 5139-5148.
Chen et al. Characterization of 582 natural and synthetic terminators and quantification of their design constraints. Nature, 2013, 10(7), 659-666.
Chen et al. Precise and programmable C:G to G:C base editing in genomic DNA. BioRxiv. 2020, 1-19, doi: https://doi.org/10.1101/2020.07.21.213827.
Cotter et al. Bacteriocins—a viable alternative to antibiotics? Nature Reviews: Microbiology. 2013, 11, 95-105.
Dickely et al. Isolation of Lactococcus lactis nonsense suppressors and construction of a food-grade cloning vector. Molecular Microbiology (1995) 15(5), 839-847.
Farzadfard et al. Genomically E1-18. ncoded Analog Memory with Precise In vivo DNA Writing in Living Cell Populations. Science. 2014, 346(6211), 1-18.
Fiedler et al. proBA complementation of an auxotrophic E. coli strain improves plasmid stability and expression yield during fermenter production of a recombinant antibody fragment. Gene 274 (2001) 111-118.

(Continued)

*Primary Examiner* — Quang Nguyen
(74) *Attorney, Agent, or Firm* — Arrigo, Lee, Guttman & Mouta-Bellum LLP

(57) ABSTRACT

The present invention concerns nucleic acids of interest for modulating the microbiome of a host, to vectors encoding the nucleic acids and to methods for in vivo modulating the microbiome of a subject by delivering the nucleic acid of interest.

8 Claims, 17 Drawing Sheets

Specification includes a Sequence Listing.

(56) References Cited

OTHER PUBLICATIONS

Fillol-Salom et al. Phage-inducible chromosomal islands are ubiquitous within the bacterial universe. The ISME Journal, 2018, 12, 2114-2128.

Fillol-Salom et al. Hijacking the Hijackers: *Escherichia coli* Pathogenicity Islands Redirect Helper Phage Packaging for Their Own Benefit. Molecular Cell 2019, 75, 1020-1030.

Flensburg et al. Bacteriophage P4 Dna Replication Nucleotide Sequence of the P4 Replication Gene and the cis Replication Region. J. Mol. Biol, 1987, 195, 439-445.

Fonfara et al. Phylogeny of Cas9 determines functional exchangeability of dual-RNA and Cas9 among orthologous type II CRISPR-Cas systems. Nucleic Acids Research, 2014, vol. 42, No. 4, 2577-2590.

Gaudelli et al. Programmable base editing of A•T to G•C in genomic DNA without DNA cleavage. Nature. 2017, 551 (7681), 464-471.

Grunewald et al. A dual-deaminase CRISPR base editor enables concurrent adenine and cytosine editing. Nat Biotechnol. 2020, 38(7): 861-864.

Henkel et al. Toxins from Bacteria. EXS. 2010, 100, 1-29.

Jinek et al. A programmable dual RNA-guided DNA endonuclease in adaptive bacterial immunity. Science. 2012, 337 (6096), 816-821.

Kanhere et al. A novel method for prokaryotic promoter prediction based on DNA stability. BMC Bioinformatics, 2005, 6 (1), 1-10.

Karberg et al. Group II introns as controllable gene trageting vectors for genetic manipulation of bacteria. Nature Biotechnology, 2001, 19, 1162-1167.

Komor et al. Programmable editing of a target base in genomic DNA without double-stranded DNA cleavage. Nature, 533(7603), 420-424.

Koonin et al. Diversity, classification and evolution of CRISPR-Cas systems. Curr Opin Microbiol. 2017, 37, 67-78.

Kurt et al. CRISPR C-to-G base editors for inducing targeted DNA transversions in human cells. Nat Biotechnol. Jan. 2021 ; 39(1): 41-46.

Li et al. Targeted, random mutagenesis of plant genes with dual cytosine and adenine base editors. Nature Biotechnology. 2020, 38, 875-882.

MacCormick et al. Construction of a food-grade host/vector system for Lactococcus lactis based on the lactose operon. FEMS h4ierebiology Letters 127 (1995), 105-109.

Matsumoto-Mashimo et al. A new family of conditional replicating plasmids and their cognate *Escherichia coli* host strains. Research in Microbiology 155 (2004), 455-461.

Mutalik et al. Precise and reliable gene expression via standard transcription and translation initiation elements. Nature Methods. 2013, 10(14), 354-368.

Negi et al. Gut bacterial peptides with autoimmunity potential as environmental trigger for late onset complex diseases: In-silico study. PLOS One. 2017, 12(7), 1-17.

Panayotatos. DNA replication regulated by the priming promoter. Nucleic Acids Research. 1984, 12(6), 1-8.

Rees et al. Base editing: precision chemistry on the genome and transcriptome of living cells. Nat Rev Genet. 2018, 19 (12), 770-788.

Sharon et al. Functional genetic variants revealed by massively parallel precise genome editing. Cell. 2018, 175(2): 544-557.

Shmakov et al. Diversity and evolution of class 2 CRISPR-Cas systems. Nat Rev Microbiol. 2017,15(3), 169-182.

Simon et al. Survey and Summary: Retrons and their applications in genome engineering. Nucleic Acids Research, 2019, 47(21), 11007-11019.

Sorensen et al. A Food-Grade Cloning System for Industrial Strains of Lactococcus lactis. Applied and Environmental Microbiology. 2000, 66(4), 1253-1258.

Stanton et al. Genomic Mining of Prokaryotic Repressors for Orthogonal Logic Gates. Nat Chem Biol. 2014; 10(2): 99- 105.

Struhl et al. Functional genetic expression of eukaryotic DNA in Escherichia coli. Proc. Natl. Acad. Sci. USA, 73(5), 1471-1475,.

Tilg et al. The intestinal microbiota fuelling metabolic inflammation. Nature Reviews: Immunology. 2019, 20, 40-54.

Wannier et al. Improved bacterial recombineering by parallelized protein discovery. 2020, pp. 1-70, doi: https://doi.org/10.1101/2020.01.14.906594.

Weigele. Biosynthesis and Function of Modified Bases in Bacteria and Their Viruses. Chem. Rev. 2016, 116, 12655-12687.

Yan et al. Cas13d is a compact RNA-targeting type Vi Crispr effector positively modulated by a WYL domain-containing accessory protein. Mol Cell. 2018, 70(2), 327-339.

Zhao et al. New base editors change C to A in bacteria and C to G in mammalian cells. Nature Biotechnology. 2020, 39, 35-40.

Ziegelin et al. The repA Gene of the Linear Yersinia enterocolitica Prophage PY54 Functions as a Circular Minimal Replicon in *Escherichia coli*. Journal of Bacteriology, 2005, 187(10), 3445-3454.

Johnston et al. Systematic evasion of the restriction-modification barrier in bacteria. PNAS, 2019, 116, 11454-11459.

\* cited by examiner

SEQUENCE LISTING

```
Sequence total quantity: 30
SEQ ID NO: 1            moltype = AA  length = 17
FEATURE                 Location/Qualifiers
source                  1..17
                        mol_type = protein
                        note = insulin B9-25 epitope
                        organism = synthetic construct
SEQUENCE: 1
SHLVEALYLV CGERGFF                                                    17

SEQ ID NO: 2            moltype = AA  length = 15
FEATURE                 Location/Qualifiers
source                  1..15
                        mol_type = protein
                        note = T cell (Beta2GPI) epitope
                        organism = synthetic construct
SEQUENCE: 2
KVSFFCKNKE KKCSY                                                      15

SEQ ID NO: 3            moltype = AA  length = 11
FEATURE                 Location/Qualifiers
source                  1..11
                        mol_type = protein
                        note = B cell epitope
                        organism = synthetic construct
SEQUENCE: 3
VSRGGMRKFI C                                                          11
```

| SEQ ID NO: 4 | moltype = DNA  length = 282 |
|---|---|
| FEATURE | Location/Qualifiers |
| source | 1..282 |
| | mol_type = other DNA |
| | note = primase ori from the PICI of the Escherichia coli strain CFT073 |
| | organism = synthetic construct |

SEQUENCE: 4

```
tttgttgcaa tggctgtcta ccctgtctac ctgagtaaag aaaaatacat ttaattcagt   60
acattaactt gggtagacag cctttttttta ctgtctacct actatctacc ctctctacct  120
gattttacct gaatcagaca gggaggtaga tacggggtag atagtggata aaagcactct  180
accccactga aagccgcgcc attactggca tggtggccag taaggtagat aaggtagaca  240
aggggaggca caactcaaaa ctttttaaac gaggggtaa aa                      282
```

| SEQ ID NO: 5 | moltype =   length = |
|---|---|
SEQUENCE: 5
000

| SEQ ID NO: 6 | moltype = DNA  length = 282 |
|---|---|
| FEATURE | Location/Qualifiers |
| source | 1..282 |
| | mol_type = other DNA |
| | note = Primase ori deltaGAAABCC |
| | organism = synthetic construct |

SEQUENCE: 6

```
tttgttgcaa tggctgtcta ccctgtctac ctgagtaaag aaaaatacat ttaattcagt   60
acattaactt gggtagacag cctttttttta ctgtctacct actatctacc ctctctacct  120
gattttacct gaatcagaca gggaggtaga tacggggtag atagtggata aaagcactct  180
accccactga aagcagcgcc attactggca tggtggccag taaggtagat aaggtagaca  240
aggggaggca caactcaaaa ctttttaaac gaggggtaa aa                      282
```

| SEQ ID NO: 7 | moltype = DNA  length = 282 |
|---|---|
| FEATURE | Location/Qualifiers |
| source | 1..282 |
| | mol_type = other DNA |
| | note = Primase ori devoid of restriction sites |
| | organism = synthetic construct |

SEQUENCE: 7

```
tttgttgcaa tggctgtcta ccctgtctac ctgagtaaag aaaaatacat ttaattcagt   60
atattaactt gggtagacag cctttttttta ctgtctacct tctgtctacc ctctctacct  120
gattttacct gaatcagaca gggaggtaga cacggggtag acagtggata aaagcactct  180
accccactga aagcagtgcc attactggca tggttgccag taaggttgat aaggtagaca  240
aggggaggga caactcaaaa ctttttaaac gaggggtaa aa                      282
```

| SEQ ID NO: 8 | moltype = AA  length = 584 |
|---|---|
| FEATURE | Location/Qualifiers |
| source | 1..584 |
| | mol_type = protein |
| | note = PICI primase-helicase |
| | organism = synthetic construct |

SEQUENCE: 8

```
MKLAPNVKQQ SRGIKHKETE VIIFAGSDAW SHAKQWQEHD ARMAGDNEPP VWLGEQQLSE   60
LDKLQIVPEG RKSVRIFRAG YLAPVMIKAI GQKLAAAGVQ DANFYPDGMH GQKVENWREY  120
LARERQNLSD GLVIELPVKQ KAQLSQMADS ERAQLLADRF DGVCVHPESE IVHVWCGGVW  180
CPVSTMELSR EMVAIYSEHR ATFSKRVINN AVEALKVIAE PMGEPSGDLL PFANGALDLK  240
TGEFSPHTPE NWITTHNGIE YTPPAPGENI RDNAPNFHKW LEHAAGKDPR KMMRICAALY  300
MIMANRYDWQ MFIEATGDGG SGKSTFTHIA SLLAGKQNTV SAEMTSLDDA GGRAQVVGSR  360
LIVLADQPKY TGEGTGIKKI TGGDPVEINP KYEKRFTAVI RAVVLATNNN PMIFTERAGG  420
VARRRVIFRF DNIVSEAEKD RELPEKIAAE IPVIIRRLLA NFADPEKARA LLIEQRDGDE  480
ALAIKQQTDP VIEFCQFLNF LEEARGLMMG GGGDSVKYTT RNSLYRVYLA FMAYAGRSKP  540
LNVNDFGKAM KPAAKVYGHE YITRKVKGVT QTNAITTDDC DAFL                   584
```

| SEQ ID NO: 9 | moltype = DNA  length = 1752 |
|---|---|
| FEATURE | Location/Qualifiers |
| source | 1..1752 |
| | mol_type = other DNA |
| | note = PICI primase-helicase |
| | organism = synthetic construct |

SEQUENCE: 9

```
atgaaactgg caccgaacgt aaaacagcag tcacgcggca taaaacacaa agaaacagaa   60
gtcattattt ttgcgggtag tgatgcctgg tcacacgcaa acaatggca ggaacatgac   120
gcgcgtatgg ccggagataa tgagcctcct gtgtggcttg gggagcagca gttatccgaa  180
ctggataagc tgcaaattgt gccggaaggc agaaaatccg tgcgcatatt cagggccgga  240
tatcttgcgc cgtaatgat aaaggcgatt ggtcagcag tggcggcggc aggcgtacag  300
gatgcaaatt tttaccctga tggtatgcac ggtcagaagg tggagaactg gcgcgaatat  360
ctggcccgtg agcgccagaa tctttctgat ggtctggtca ttgagcttcc ggtaaagcaa  420
aaggcgcaac tttcgcagat ggcggacagt gagcgcgcgc agctgcttgc cgatcgcttt  480
gatggcgttt gcgtacatcc tgaaagtgaa atcgttcacg tatggtgcgg cggggtatgg  540
tgtccggtca gcacaatgga gctgagccgc gaaatggtgg cgatctattc agagcacagg  600
```

-continued

```
gccactttca gcaagcgcgt aatcaataac gccgtggaag cgttaaaagt tattgccgaa  660
ccaatgggcg agccgtccgg cgatttgctg ccgttcgcca atggtgcgct tgacctgaaa  720
acggggggaat tttccccgca cacgccgag aactggatca ccacgcacaa cggcattgag  780
tacacgccac cagcacccgg ggagaacatc cgcgataacg cgccaaactt tcataaatgg  840
cttgagcacg cagccggaaa agacccgcgc aagatgatgc gtatatgtgc cgcgctgtac  900
atgattatgg cgaaccggta cgactggcag atgtttattg aggccaccgg agacggcggg  960
agcggtaaaa gtacattcac acacatagcc agccttctgg cagggaaaca aaacacggta  1020
agcgctgaaa tgacatcgct tgatgatgct ggtgggcgtg cgcaggttgt cgggagtcgt  1080
cttatcgtcc tggcagacca gccgaaatat acaggcgaag gaacgggcat caagaaaatc  1140
acgggcggcg accccgtgga aattaacccg aaatatgaaa agcgttttac ggccggtaatc  1200
agggcggtgg tgctggcaac caataacaat ccgatgatat tcaccgaacg ggccggaggt  1260
gtggcacgtc gtcgggtgat attccggttc gataacatcg taagcgaggc agaaaaagac  1320
agggagctac cggaaaagat cgcggctgaa atccctgtca ttatccgccg cttgctggcg  1380
aactttgccg accctgaaaa ggcacgggct ttactcattg aacagcgtga cggtgatgaa  1440
gcactggcaa taaagcaaca gacggatccg gttattgagt tttgccagtt cctgaatttt  1500
ctggaggaag cacgcggcct gatgatgggc ggcggtggcg attcagtgaa gtacacgacc  1560
agaaacagcc tttaccgcgt ctatctggcg tttatgcgct acgcaggcag gagcaaaccg  1620
ctaaacgtaa atgactttgg caaggctatg aagccagccg cgaaagttta cggacatgaa  1680
tatattacgc ggaaagttaa aggagtaacg cagactaacg caataacaac agacgattgc  1740
gacgcgtttt ta                                                     1752

SEQ ID NO: 10         moltype = DNA   length = 11615
FEATURE               Location/Qualifiers
source                1..11615
                      mol_type = other DNA
                      note = payload p1392 plasmid
                      organism = synthetic construct
SEQUENCE: 10
gtttgcaata agggacaagt tacgagtgta gacacgcaga attatccagc ctttagtctt   60
taggaaggca aagctattgt acgcggtagc cgtcgtagca atttaccaac tgtagaatta  120
ttggacacac gtaacaaggg cttacgattg aagtttaata aggtcacacg caaaaccgct  180
aaggaataat cgcaccgtta gcgaaagaat atttcagagc ggttagtaaa ggttgagtaa  240
agtgagattc caaagtgagc ctttataaaa agtaaagagc tataatakaa ccgtcgatcg  300
gaaaacaatc gcctgaaatc tcaagcacgt tgccctttct aacgtcgcta aggtttcgta  360
aacccgtttg attaggaaga agaataagta acccgattag gtttgagatc gcgggttatc  420
ggtttggatt aaaagtggat accagcggag tcaacgccga cgcaaacgta cagtgatcca  480
atcctgttcc acggtcaagc acaatcagct agcaagatct tggaatagag tcgttgcacc  540
gctttgattt acatgctctc cattgcacaa cattccggaa ggactggctt ctctgccatg  600
atcggataat gaaaaacatc atatgccct gtcattttttc tttgggtgtc ctcaaataat  660
tgccctcacg ttatcgtatg tgacgcgctc atctatgctc gaagtattcc ttgttctccc  720
atcttttaat agaaagtctt taatgaacgt gtcgttacgc agtgtatgaa ctcttgtttt  780
ataggggcaga ctttggcgtg gcctaagtgt gttcgataag aaggcaagga caactagctg  840
acgcgctgta atacggatat tatggcacgg ttgatacaaa cgctgatatc ctgatttgct  900
aatgtgccca acactttagt tgagtgccac gttccgacta caagttgctt caagaggga  960
atttggattt ggcaatagcc cccgtttcct acctcaagag gcgacgagta ttaaccgcgc  1020
cagctttcgg cacaagggcc aaagaagatt ccaatttctt attcccgaat aacctccgaa  1080
tccctgcggg aaaatcaccg accgaatagc ctagaagcaa ataggtataa  1140
ttagcttaag agagtaccag ccgtgacaac accgtagtaa ccacaaactt acgctgggc  1200
ttctttggcg gatttttaca gatactaaca aggtgatttg aagtacctta gttgaggatt  1260
taaacgcgct atccggtagt ctacaaattg gaaataccg ttcaaagagg gctagaatta  1320
cttaaaagcc ttcacaccgc ctgcgctata cgcgcccact ctcccgttta tccgtccaag  1380
cggaagcagg gcgaacttcc gctaagatat tcttacgtgt aacgtagcta agtatcccaa  1440
atagctggcg tacgcgttga acaccgccta gaggatcggg agtcgccgga cgagcgtgtt  1500
attgggggact tacgccagcg tagactacaa cgcgcccaga ttaaccctgc acgtattgcc  1560
ttgaataacg tactaatctc tccggctctc gacaatctat cgagcgactc gattatcaac  1620
gggtgtcttg cagttctaat ctcttgcccc cgcccgtaat agcctccaag tgattcaaga  1680
tagtaaaggg caagagctta ttcggcgttg aaggatagcg gactttcggt caaccacaat  1740
tcccccactcg acaaaaccag ccgtgcgaag aactctgaaa gtacaagcaa cccaagaggg  1800
ctgagcctaa actcagctaa ttcctaagtg agctaaagac tcgaagtgac agctattaat  1860
aaatagagcg ggaacgtcga acggtcgtga aagtaataagt acaacgggta ttaacttact  1920
gaggatattg cttgaagctg taccgtttta ttgggtgaac gaataagatc cagcaattca  1980
gccaaagaag ctaccaattt ttagtttaag agtgtcacgt ctgacctcgc gggtggatag  2040
ccgaacgtag agcttacgag ccagcggaaa cagtagccgc aggataagta aggggagtaa  2100
gtgatcgaac gaatcagaag tgacaatata cttaggctgg atctcgtccc gtgaatcgaa  2160
accctcacca actacgagat aagaggtaag ccagaaatcg gcatggtggc gaccaacgac  2220
tgttcccccc ctgtaactaa tcgttccgtc aaacctgac ttacttcaag gccaattcca  2280
agcgcaaaca ataccgtcct agttcttcgg ttaagtttcc gaagtaggag tgagcctacc  2340
tccgtttgcg tcttgttacc actgacccag ctatttactt tgtattgcct gcaatcgaat  2400
ttctgaactc tcagatagtg gggataacgg gaaagttcct atatttgcga actaacttag  2460
ccgtccacct cgaagctacc tactcacacc cacccccgcgc ggggtaaata aggcactaat  2520
cccagcttag agcttgcgta gcacttagcc acaagttaat taacagttgt ctggtagttt  2580
ggcggtatta cgcgagatcct agaagcaagg cagagttagt tctaacctaa agccacaaat  2640
aagcaggtt gccaaagccc gccggaaatt aaatcttgct cagttcggta acggagtttc  2700
cctcccggtt acttaattcc caataagaaa cgcgcccaag tcctatcagg caaaattcag  2760
cccttcccg tgttagaacg aggtaaaaa tacaagccga ttgaacaagg gttgggggct  2820
tcaaatcgtc gttacccca ctttacacg gagggtaagt agttcaccct atagtacgaa  2880
gcagaactat ttcgaggggc gtgcaataat cgaatcttct gcggttgact taacacgcta  2940
gggacgtgcc ctcgattcag tcgcaggtac tcctactcag actgcctcac acccagctag  3000
tcactgagcg ataaaattga cccgcccctct aaggtagcga gtacgtccca aagggctccg  3060
```

-continued

```
gacagggcta tataggagag tttgatctcg ccccgacaac tgcaaccctc aactcccttg  3120
gataatattg ttagccgaag ttgcacgacc cgccgtccac ggactgctct tagggtgtgg  3180
ctccttaatc tgacaacgtg caaccccctat cgagggcgat tgtttctgcg aaaggtgttg  3240
tcctaatagt cgcgacattt ggcccttgta ggtgtgaaac cacttagctt cgcgccgtag  3300
tcctaaaggc ccacctattg actttgtttc gggtagcact aggaatctta acaatttgaa  3360
tttggacgtg gaacgcgtac accttgatct tcgaataatt ctagggattt ggaagtcctc  3420
tacgttgaca cacctacaat gctccaagta aatatacgaa taacgcgggc ctcgcggagc  3480
cgttccgaat cgtcacgtgt tcgtttactg ttaattggtg gcaaataagc aatatcgtag  3540
tccgtcaggc ccagccctgt tatccacggc gttatttgtc aaattgcgta gaactggatt  3600
gactgcctga caatacctaa ttatcggtac gaagtcccg aatctgtccg gctatttcac  3660
taatactttc caaacgcccc gtatccaaga agaacgaatt tatccacgct cccgtctttg  3720
ggacgaatac cgctacaagt ggacagagga tcggtacggg cctctaataa atccaacact  3780
ctacgccctc ttcaagagct agaagaacag ggtgcagttg gaaagggaat tatttcgtaa  3840
ggcgagccaa taccgtaatt aattcggaag agttaacacg attggaagta ggaatagttt  3900
ctaaccacgg ttactaatcc taataacgga acgctgtctg atagattagt gtcagcgctc  3960
actaccaaag aaaaataaaa agacgctgaa aagcgtcttt ttattttcg gtccagtgta  4020
actcaggcaa aagcacgtaa tattcgtact caccaaacga aactcatccg gcgcatcgcg  4080
cttcttcctc cgtaagcgtc accccattca cttaaagagt gcatgtgcat attttgttat  4140
caataaaaaa ggccgcgatt tgcggcctta ttgttcgtct tgccggatta gatagctacc  4200
ggtgctttaa tacccggatg cggatcatag ccttcgattt cgaagtcctc aaaacgataa  4260
tcgaagatgc tttccggttt gcgtttgata atcagtttcg ggagcgggcg tggctcacgg  4320
cttaattgta aatgcgtctg atccatgtga tttgagtaca ggtgagtatc ccaccagtc  4380
caaacaaagt caccaacttc cagatcacac tgctgtgcca tcatatgaac taataaggcg  4440
taggaggcaa tgttaaacgg taagcccaga aacacgtcgc aagaacgctg gtacagttgg  4500
cacgataact taccatccgc aacatagaat tgaaagaagg catgacacgg tgctaaagcc  4560
attttgtcta attcccccac gttccatgcg gacacgataa tccggcgaga gtccggatca  4620
tttttcagtt ggttaagaac ggtagtgatc tgatcaatat gccgaccatc cggcgtaggc  4680
catgcacgcc attgcttacc atacactggc cctaagtcac cgttttcatc tgcccactca  4740
tcccagatgg taacgttatt ctcgtgcagg tacgcaatgt tcgtatcgcc ttgcagaaac  4800
cataataact cgtgaataat agaacggagg tggcaacgct tggtagtgac cagcgggaaa  4860
ccgtcttgca ggttgaaacg catctgatga ccaaagatag acagcgtacc agtgccagta  4920
cgatcattct tctgagtgcc ttcgtccagc acttttgca tcagttccag atactgtttc  4980
attttagctt ccttagcttg cgaaatctcg ataactcaaa aaatagtagt gatcttattt  5040
cattatggtg aaagttgtct tacgtgcaac attttcgcaa aaagttggcg ctttatcaac  5100
actgtccgaa tgacaaatgg ttacaattat tgaacaccct tcggggtgtt tttttgtttc  5160
tggtttcccg aggccgaact tttgttgcaa tggctgtcta ccctgtctac ctgagtaaag  5220
aaaaatacat ttaattcagt atattaactt gggtagacag ccttttttta ctgtctacct  5280
tctgtctacc ctctctacct gatttttacct gaatcagaca gggaggtaga cacggggtag  5340
acagtggata aaagcactct accccactga aagcagtgcc attactggca tggttgccag  5400
taaggttgat aaggtagaca aggggaggga caactcaaaa cttttttaaac gaggggtaa  5460
aacgcagatc aaaacgatct caagaagatc atcttattaa tcagataaaa tatttctaga  5520
tttcagtgca atttatctct tcaaatgtag caccggcgcg ccgtgaccaa ttattgaagg  5580
ccgctaacgc ggccttttt tgtttctggt ttcccgaata gagcgacttc tccccaaaaa  5640
gcctcgcttt cagcacctgt cgtttccttt cttttcagag ggtatttaa ataaaaacat  5700
taagttatga cgaagaagaa cggaaacgcc ttaaaccgga aaattttcat aaatagcgaa  5760
aacccgcgag gtcgccgccc cgtaacctgt cggatcaccg gaaagaacct gtaaagtgat  5820
aatgattatc atctacatat cacaacgtgc gtaaagggta agtatgaagg tcgtgtactc  5880
catcgctacc aaattccaga aaacagacgc tttcgagcgt ctttttttcgt tttggtcacg  5940
acgtacggtg gaagattcgt taccaattga cagctagctc agtcctaggt atatacatac  6000
atgcttgttt gtttgtaaac tactgttttc attaaagagg agaaaggaag ccatgtccat  6060
ctatcaggag tttgttaaca agtattccct gtctaaaacc ctgcgttttg aactgatccc  6120
gcagggcaaa actttggaaa acattaaagc gcgtggcctg attctggatg acgaaaaacg  6180
tgcaaaggat tacaagaaag ctaaacagat catcgacaaa tatcaccagt tctttatcga  6240
agaaattctg tcctcggtgt gcatcagtga ggatctgtta cagaattatt ctgatgtata  6300
cttttaactt aaaaagtccg atgacgataa tctgcaaaaa gatttcaagt cagccaaaga  6360
taccatcaag aaaacgatct cagaatatat taaagatagc gaaaagttca aaaacctgtt  6420
taaccaaaac ctcattgatg ctaagaaagg ccaagaatct gacctgatct tatggctgaa  6480
acagagcaaa gataacggca ttgaactgtt caaagctaat agcgacatca ccgatattga  6540
tgaagcgctc gaaatcatca agtctttcaa aggctgagca acgtatttca aaggttttca  6600
tgaaaaccgt aagaatgtat attcgagcaa cgatattccg acctctatta tttatcgtat  6660
cgtggacgac aacctgccga gtttctgga aaacaaagcg aaatatgaat ctctgaaaga  6720
caaagcaccg gaagctattta actatgaaca gatcaagaaa gatctggcgg aagaactgac  6780
cttcgacatc gactataaaa cctccgaagt taaccagcgt gttttctcac tggacgaggt  6840
tttcgaaatc gctaatttca acaattacct gaatcaactc ggcatcacca aattcaacac  6900
cattattggt ggcaaatttg ttaacgcgca aacaccaag cgtaagggca tcaacgaata  6960
cattaacctc tatagccaac aaatcaacga caaaaccctg aaaagtata aaatgtccgt  7020
tctgtttaaa cagatttat cggacaccga atctaaatcc ttcgtaattg ataaactgga  7080
agatgatagc gacgttgtca ccacgatgca gagctgtaga tgagcagatg cggcgttcaa  7140
aaccgtgata gagaaatcta ttaaagaaac tctgtccctg ctctttgacg acctcaaagc  7200
gcagaaacta gatctgtcta agatttactt taaaaacgac aaatctctga ccgatctcag  7260
tcaacaagtt tttcgatgact atagcgtgat cggcacggca gtttggaat acatcaccca  7320
acaaatcgcg ccgaaaaatc tggacaaccc gtccaagaag aacaggaac tgattgcaaa  7380
gaaaacagaa aaagctaaat acctgagctt agaaactatc aaactggcac ttgaggaatt  7440
taataaacat cgtgatattg ataaacagta tcgttttgag gaaatttcgg tgaactttgc  7500
ggcaatcccg atgatcttcg acgaaattgc tcaaaacaaa gacaatctgg cgcagatctc  7560
tatcaagtac cagaatcagg gtaagaaaga tctgcttcaa gcatctgcgg aggacgatgt  7620
caaagcaatt aaagacttat tagatcagac gaataactta ttacacaagc tcaaaatctt  7680
ccacatcagc cagagcgagg acaaggcgaa cattctggat aaagatgaac acttctatct  7740
ggtgttcgaa gaatgttact tcgaactggc aaacatcgta cctctctaca ataaaatccg  7800
```

```
caactacatc acgcagaagc cttacagtga cgagaaattc aaactgaact tcgaaaacag    7860
cacgctggcg aacggctggg ataagaacaa agagccggac aacaccgcaa tcctgttcat    7920
caaagacgac aaatactatc tgggcgtaat gaacaagaag aacaacaaga tcttcgacga    7980
taaagcgatc aaagaaaaca agggtgaagg ctataagaaa atcgtgtaca agctcctgcc    8040
gggtgcgaac aaaatgttac cgaaagtgtt cttttccgtg aaaagcatca aattctacaa    8100
cccgtctgag gatattctgc gcatccgcaa tcatagcacg cacactaaaa acggtagccc    8160
gcagaaaggg tatgaaaaat tcgaatttaa tatagaggac tgccgtaaat tcatcgactt    8220
ctataaacag agcatttcca aacatccgga atggaaagac ttcggcttcc gtttctctga    8280
cactcagcgc tataatagca tcgacgagtt ctaccgcgaa gtggagaatc agggctataa    8340
actgaccttc gagaacatta gtgagtcgta catcgactcc gttgtgaatc agggtaaact    8400
gtacctgttt cagatctata ataaagactt tagcgcgtac agcaaaggcc gcccgaatct    8460
gcacacccttt tactggaaag cattatttga cgaacgtaac ctgcaagatg tggtgtataa    8520
actgaacggt gaggcggaac ttttctaccg taaacagagt atcccgaaga aaatcacgca    8580
tccggcaaaa gaagctattg ccaacaaaaa caaagacaac ccgaagcaaa aaagtgtatt    8640
cgaatatgac ctgatcaaag ataaacgttt caccgaagat aagttctttt tccactgtcc    8700
gattaccatc aacttcaaat ctagcggtgc gaacaagttc aacgatgaaa ttaacttatt    8760
actgaaagag aaagctaatg acgtacacat cttatctatt gatcgcggtg aacgtcattt    8820
agcatactat acactggtag acggtaaagg taatattatt aaacaggata cttttcaatat   8880
tatcggtaat gaccgtatga aaaccaacta tcacgataag ctggcggcga tcgaaaaaga    8940
tcgtgattct gcgcgtaaag attggaagaa aattaacaat atcaaagaaa tgaaagaagg    9000
ctatctgagc caagtggtgc acgagatcgc aaaactggtg attgaatata cgctatcgt    9060
ggttttcgaa gatctgaact ttggttttaa acgtggtcgc ttcaaagtag aaaaacaggt    9120
gtaccaaaaa ctgaaaaaa tgctgattga aaaactgaac tatctggttt ttaaagacaa    9180
cgaatttgac aaaacgggtg gcgtactccg tgcctatcag cttaccgctc cgttcgaaac    9240
gtttaagaaa atgggtaaac aaacgggat tatctattat gtgccagccg gtttcacctc    9300
caagatttgt ccagttacgg gcttcgttaa ccagctttac ccgaaatacg agagcgttag    9360
caaatctcaa gaatttttca gcaaattcga caagatctgc tataatctgg ataaaggcta    9420
tttcgagttc agctttttgatt acaaaaactt cggcgataaa gcggctaaag gtaagtggac    9480
tattgctagc tttggtagcc gtctgattaa cttttcgcaac tccgacaaaa accataattg    9540
ggacacgcgt gaagtgtatc cgaccaaaga actggaaaaa ttactgaaag actattcgat    9600
cgaatatggt catggggagt gcattaaagc ggcgatttgc ggtgaatccg ataagaaatt    9660
tttcgccaaa ctgaccagcg tgcttaacac cattctccaa atgcgtaatt ctaaaacggg    9720
tacggagctt gactacctga tttctccggt agccgacgtt aacggcaact tcttcgattc    9780
tcgtcaagca ccgaaaaata tgcccacaaga cgcggatgcc aacggtgcat accatatcgg    9840
ccttaaaggc ttaatgttat taggccgtat caagaataat caggagggca agaaattaaa    9900
tctggttatc aaaaacgaag aatacttcga gttcgttcag aatcgtaaca attaatgtat    9960
gcttaagcag atcggtaata aagacgaaca ataagacgct gaaaagcgtc ttttttcgtt   10020
ttggtcctgt tccggcgcga tagtgtgaac atgctataga cttctggtgc tacccgactg   10080
acaattaatc atccggctcg tataatgcta gcaattttca ctgttgtaga tcattccgga   10140
acgttccagc gctgcaattt ctactgttgt agatctgatt tttcacatgt taccttttcaa   10200
tttctactgt tgtagatccg aaaacgtaaa gcttcagctg taatttctac tgttgtagat   10260
atcatatctg gcgttaatgg agtttcgtga cgaacaataa gtcctcccta acgggggca   10320
attttttattg ataacaaaag taacttcgag cttgtctacc tcctagctcg taaattgcac   10380
gctgatagtc tcccaattgc gaaggaccaa aacgaaaaaa caccctttcg ggtgtctttt   10440
ctggaattttg gtacgcagta ctaggtatcg tgtaagtagc gaaggcccgt acgcgagata   10500
aactgctagg caaccgcgac tctacgactg gtgctcgatt taatttcgct gacgtaaaga   10560
aattatcggc agtgcgtcaa ctgccgtatc tttatcttaa ttaggtagtt ggacaagcgt   10620
ttgaaagaaa tagcaagagc ctgcctctct attgaagtca cggcgaaagt cgggtagaaa   10680
tcaaagaaag cagaaattaa atcggagtaa tactaagttg ggataactcc gtaactgact   10740
acgcctttct ctagacttta cttgaccaga tacactgtct ttgacacgtt gaaggattag   10800
agcaatcaaa tccaagactg gctaagcacg aagcaactct tgagtgttaa aaagttactt   10860
cctgtattcg ggacgagggt actagaagat tgcagggact ccgacgttaa gtaaattaca   10920
aagtaataag tatcgttcag gatcacgtta ccgcaataag aagcgagaat aatataattt   10980
ccgaagtgct taccccagta gtgactattc ctataaccct tctgagtgtc cggaggcgga   11040
aatttgccac gaaagagaaa gtatttcccc gacaataata aagggggcgct cctcagcttt   11100
tccacttggt tgggtaagct aggcaactct gaaaggagtt tcggcgaagt gaagccgaca   11160
cctttgaatt gttttagggg cgttattcga gggcaatcgg agctaacttc aagactactt   11220
ctttgttgaa tactaaatag tgcaaaggtc gtgtttcctc aaggatactc cgctaacaat   11280
ataggattcc aatcagattc agcactggcg gtacgggtgt tgcggtgagg cgttcgggtt   11340
tacggctcga agctagcacg gtaggaagcc tgacaatcac caagcaaaag ggccgtcgaa   11400
ggcccacaag atacgaaagc tctcgaagcc ttatccttga ccgatccacc tatttaggca   11460
gttacgcaca aaagctaccc aataatccgt gacaggcaca atatcacgga acaaaaccga   11520
aaactctcgt acacggttag gttttcgcta ggaagaataa acctctatct tgattataag   11580
aaggctcccc aagcacccc aaaaccgaaa tagcg                                11615
```

SEQ ID NO: 11        moltype = DNA   length = 11609
FEATURE              Location/Qualifiers
source               1..11609
                      mol_type = other DNA
                      note = payload p1900 plasmid
                      organism = synthetic construct
SEQUENCE: 11

```
tcccgcgtac ttaattccca ataagaaacg cgcccaagtc ctatcaggca aaattcagcc      60
ccttcccgtg ttagaacgag ggtaaaaata caagccgatt gaacaagggt tgggggcttc     120
aaatcgtcgt ttaccccact ttacaacgga gggtaagtag ttcacccctat agtacgaagc    180
agaactattt cgaggggcgt gcaataatcg aatcttctgc ggttgactta acacgctagg     240
gacgtgcccct cgattcagtc gcaggtactc ctactcagac tgcctcacac ccagctagtc    300
actgagcgat aaaattgacc cgccctctaa ggtagcgagt acgtcccaaa gggctccgga    360
cagggctata taggagagtt tgatctcgcc ccgacaactc caaccctcaa ctcccttaga    420
```

```
taatattgtt agccgaagtt gcacgacccg ccgtccacgg actgctctta gggtgtggct    480
ccttaatctg acaacgtgca acccctatcg agggcgattg tttctgcgaa aggtgttgtc    540
ctaatagtcg cgacatttgg cccttgtagg tgtgaaacca cttagcttcg cgccgtagtc    600
ctaaaggccc acctattgac tttgtttcgg gtagcactag gaatcttaac aatttgaatt    660
tggacgtgga acgcgtacac cttgatcttc gaataattct agggatttgg aagtcctcta    720
cgttgacaca cctacaatgc tccaagtaaa tatacgaata acgcgggcct cgcggagccg    780
ttccgaatcg tcacgtgttc gtttactgtt aattggtggc aaataagcaa tatcgtagtc    840
cgtcaggccc agccctgtta tccacggcgt tatttgtcaa attgcgtaga actggattga    900
ctgcctgaca atacctaatt atcggtacga agtcccgaca tctgtccggc tatttcacta    960
atactttcca aacgcccgt atccaagaag aacgaattta tccacgctcc cgtctttgg     1020
acgaataccg ctacaagtgg acagaggatc ggtacgggcc tctaataaat ccaacactct   1080
acgccctctt caagagctag aagaacaggg tgcagttgga aagggaatta tttcgtaagg   1140
cgagccaata ccgtaattaa ttcggaagag ttaacacgat tggaagtagg aatagtttct   1200
aaccacggtt actaatccta ataacgaac gctgtctgat agattagtgt cagcgctcac   1260
taccaaagaa aaataaaaag acgctgaaaa cgtctttttt attttcggt ccagtgtaac   1320
tcaggcaaaa gcacgtaata ttcgtactca ccaaacgaaa ctcatccggc gcatcgcgct   1380
tcttcctccg taagcgtcac ccccattact taaagagtgc atgtgcatat tttgttatca   1440
ataaaaaagg ccgcgatttg cggccttatt gttcgtcttg ccggattaga tagctaccgg   1500
tgctttaata cccggatgcg gatcatagcc ttcgatttcg aagtcctcaa aacgataatc   1560
gaagatgctt tccggtttgc gtttgataat cagtttcggg agcgggcgtg gctcacggct   1620
taattgtaaa tgcgtctgat ccatgtgatt tgagtacagg tgagtatccc caccagtcca   1680
aacaaagtca ccaacttcca gatcacactg ctgtgccatc atatgaacta ataaggcgta   1740
ggaggcaatg ttaaacggta agcccagaaa cacgctcgca gaacgctggt acagttggca   1800
cgataactta ccatccgcaa catagaattg aaagaaggca tgacacgtg ctaaagccat    1860
tttgtctaat tcccccacgt tccatgcgga cacgataatc cggcgagagt ccggatcatt   1920
tttcagttgg ttaagaacgg tagtgatctg atcaatatgc cgaccatccg gcgtaggcca   1980
tgcacgccat tgcttaccat acactggccc taagtcaccg ttttcatctg cccactcatc   2040
ccagatggta acgttattct cgtgcaggta cgcaatgttc gtatcgcctt gcagaaacca   2100
taataactcg tgaataatag aacggaggtg gcaacgcttg gtagtgacca gcgggaaacc   2160
gtcttgcagg ttgaaacgca tctgatgacc aaagatagac agcgtaccag tgccagtacg   2220
atcattcttc tgagtgcctt cgtccagcac tttttgcatc agttccagat actgtttcat   2280
tttagcttcc ttagcttgcg aaatctcgat aactcaaaaa atagtagtga tcttatttca   2340
ttatggtgaa agttgtctta cgtgcaacat tttcgcaaaa agttggcgct ttatcaacac   2400
tgtccgaatg acaaatggtt acaattattg aacacccttc ggggtgtttt tttgtttctg   2460
gtttcccgag gccgaacttt tgttgcaatg gctgtctacc ctgtctacct gagtaaagaa   2520
aaatacattt aattcagtat attaacttgg gtagacagcc ttttttttact gtctaccttc   2580
tgtctaccct ctctacctga ttttacctga atcagacagg gaggtagaca cggggtagac   2640
agtggataaa agcactctac cccactgaaa gcagtgccat tactggcatg gttgccagta   2700
aggttgataa ggtagacaag gggagggaca actcaaaact ttttaaacga ggggggtaaa   2760
cgcagatcaa aacgatctca agaagatcat cttattaatc agataaaata tttctagatt   2820
tcagtgcaat ttatctcttc aaatgtagca ccggcgcgcc gtgaccaatt attgaaggcc   2880
gctaacgcgg ccttttttg tttctggttt cccgaataga gcgacttctc cccaaaaagc   2940
ctcgctttca gcacctgtcg tttccttct tttcagaggt tatttaaat aaaaacatta   3000
agttatgacg aagaagaacg gaaacgcctt aaaccggaaa attttcataa atagcgaaaa   3060
cccgcgaggt cgccgccccg taacctgtcg gatcaccgga agaacctgt aaagtgataa    3120
tgattatcat ctacatatca caacgtgcgt aaagggtaag tatgaaggtc gtgtactcca   3180
tcgctaccaa attccagaaa acagacgctt tcgagcgtct ttttttcgttt tggtcacgac  3240
gtacggtgga agattcgtta ccaattgaca gctagctcag tcctaggtat atacatacat   3300
gcttgttttgt ttgtaaacta ctgttttcat taaagaggag aaaggaagcc atgaccaaaa   3360
cgtttgatag cgagttttttt aacctgtaca gcctgcaaaa aaccgtgcgc tttgaattaa   3420
aaccagtggg cgaaaccgcg agcttttgtgg aagattttaa aaacgaaggc ctgaaacgtg   3480
tggttagcga agatgaacgc cgtgcgtgg attatcagaa agtgaaagaa attattgatg   3540
attatcatcg cgattttatt gaagaaagtc tgaactattt tccggaacag gtgagcaaag   3600
atgcgctgga acaggcgttt catctgtatc agaaatttaaa ggccgcgaaa gttgaagaaa   3660
gagaaaaagc gctgaaagaa tgggaagcac tgcaaaaaaa actgcgtgaa aagtggtgta   3720
aatgctttag cgatagcaat aaagcgcgtt tctcccgcat tgataaaaag gaactgatta   3780
aagaagatct gattaactgg ctggtcgcgc agaatcgcga agatgatatc ccgaccgtgg   3840
aaacctttaa caactttacc acgtattta cgggcttcca tgaaaaccgt aaaaacattt   3900
atagcaaaga tgatcatgcg accgcgatta gctttcgcct gattcatgaa aactgcgca   3960
aattttttga taacgtgatt agctttaaca aactgaaaga aggttttccg gaactgaaat   4020
ttgataaagt gaaagaagat ttagaggtgg attatgatct gaaacatgcg tttgagattg   4080
aatattttgt taactttgtg acccaggcgg gcatagatca gtataactat ctgttaggcg   4140
gtaaaaccct ggaagatggc accaaaaagc agggcatgaa tgaacagatt aacctgttta   4200
aacagcaaca aacgcgat aaagcgcgtc agattccgaa actgatccg ctgtttaaac   4260
agatttaag cgaaaggacc gaaagtcaga gctttattcc gaaacagttt gaaagcgatc   4320
aggaattgtt tgatagcttg cagaaattac ataacaactg ccaggataaa tttaccgtgt   4380
tgcaacaagc gattctgggc ctggcggagg cggatctgaa aaaagtgttt attaaaacct   4440
ctgatctgaa cgcgctgtct aacaccattt ttggcaatta tagctgtgtt agcgatgcgc   4500
tgaatctgta taagaaagt ctgaaaacca aaaagcgag cgaaagtttt gaaaactgc   4560
cagcgcatag cattcatgat ctgattcagt atctggaaca gtttaactcc agcttggatg   4620
cggaaaaaca gcaaagcacc gataccgtcc tgaactattt tatcaaaacg gatgaactgt   4680
attctcgctt tattaaaagc accagcgaag ccttttccca ggtgcaaccg ttgtttgaac   4740
tggaagcgct gtccagcaaa cgtcgcccgc cggaaagcga agatgagggc gcgaaaggcc   4800
aggaaggcct cgaacaaatc aagctatta agcgtatct atgaaggcg gataccctg   4860
tgcactttgc gaaaccgctg tatctgtga aaggtcgtaa aatgatcgaa ggcctcgata   4920
aagatcagag cttttacgaa gcgtttgaaa tggcgtatca ggaattagaa agcttaatca   4980
ttccgatcta taacaaagcg cgtagctatt tgtcgcgcaa accgtttaaa gcggataaat   5040
ttaaaattaa cttttgataac aacacccctg taagcggttg gacgcgaac aaagaaaccg   5100
ccaacgcgtc cattctgttt aaaaaagatg gcctgtatta tctgggtatt atgccgaagg   5160
```

-continued

```
gtaaaacctt tctctttgat tattttgtgt cgagcgaaga tagcgaaaaa ctgaaacagc  5220
gtcgccagaa aaccgccgaa gaagcgctgg cgcaggatgg cgaaagctat tttgaaaaaa  5280
ttcgttataa actgttaccg ggcgcgagca aaatgttacc gaaagtgttt tttagcaaca  5340
aaaacattgg cttttataac ccgagcgacg atattctgcg catccgcaac accgccagcc  5400
ataccaaaaa cggcaccccg cagaaaggcc atagcaaagt ggaatttaac ctgaacgatt  5460
gccataagat gattgatttt tttaaatcca gcattcagaa acatccggaa tggggatctt  5520
ttggctttac ctttagcgat accagcgatt ttgaagatat gagcgcgttt tatcgcgaag  5580
tggaaaatca gggttacgtg attagctttg ataaaatcaa agaaacctat atccagagtc  5640
aggtggaaca gggtaatctg tatctgtttc agattataa caaagatttt agcccgtata  5700
gcaaaggcaa accaaacctg cacacccctgt attggaaagc gttatttgaa gaagccaacc  5760
tgaataacgt ggtggcgaaa ctgaacggtg aagcggaaat ctttttttcgt cgtcatagca  5820
ttaaagcgag cgataaagtg gtgcatccgg caaaccaggc gattgataac aaaaatccgc  5880
ataccgaaaa aacgcagagc acctttgaat atgatctggt gaaagataaa cgctataccc  5940
aagataaatt tttttttcac gtgccgatca gcctcaactt taaagcgcag ggcgtgagca  6000
aatttaacga taaagtgaac ggcttcctga aaggcaaccc ggatgtcaac attattggta  6060
ttgatcgggg cgagcgccat ctgcttatt ttaccgtggt gaatcagaaa ggtgaaattc  6120
tcgttcagga aagcttaaac accctgatga gcgataaagg ccatgtgaac gattatcagc  6180
aaaaactgga taaaaaagaa caggacgtg atgcggcacg taaatcttgg accacggtgg  6240
aaaacattaa agaattgaaa gaaggctatt taagccatgt ggtgcataaa ctggcgcacc  6300
tgatcattaa atataacgcg attgtgtgcc tggaggacct gaattttggc tttaaacgcg  6360
gtcgctttaa agtggaaaaa caggtttatc agaaatttga aaaagcgctg attgataaac  6420
tgaactatct ggtgtttaaa gaaaaagaat taggtgaagt gggcattat ctgaccgcgt  6480
atcaactgac cgcgccgttc gaaagcttta aaaactggg taaacagtct ggcattctgt  6540
tttacgtccc ggcggattat acctccaaaa tcgatccgac cacggcttc gttaactttc  6600
tggatctgcg ctatcagagc gtggaaaaag cgaaacagct tctgtccgat tttaacgcga  6660
ttcgtttaa cagcgtgcag aactattttg aatttgaatt tgattataaa aaactgaccc  6720
cgaaacgtaa agtcggcacc caaagtaaat gggttatttg cacctatggc gatgtgcgct  6780
atcagaatcg tcgcaatcag aaaggtcatt gggaaaccga agaagtgaac gtgaccgaaa  6840
agctgaaagc gttatttgcg agcgatagca aaacgaccac ggttatcgat tatgccaacg  6900
acgacaacct gattgatgtg attttagaac aggataaagc gagcttttt aaagaattat  6960
tgtggttact gaaactgacc atgaccctgc gccatagcaa aattaaaagc gaagatgatt  7020
ttattctgtc cccggtgaaa aatgaacagg gtgaatttta tgatagccgt aaagcgggcg  7080
aagtttggcc taaagatgcg gatgccaacg cgcgtatca tatcgcgctg aaaggccttt  7140
ggaatttaca gcaaattaac cagtgggaaa aaggtaaaac cctgaattta gcgatcaaaa  7200
accaggattg gtttagcttt atccaggaaa aaccgtatca ggaatgatga aagcttatgc  7260
agatcggtaa taaagacgaa caataagacg ctgaaaagcg tctttttttcg ttttggtcct  7320
gttccggcgc gatagtgtga acatgctata gacttctggt gctacccgac tgacaattaa  7380
tcatccggct cgtataatgc tagcaatttc tactgttgta gatcattccg gaacgttcca  7440
gcgctgcaat ttctactgtt gtagatctga tttttcacat gttaccttttc aatttctact  7500
gttgtagatc cgaaaacgta aagcttcagc tgtaattct actgttgtag atatcatatc  7560
tggcgttaat ggagtttcgt gacgaacaat aagtcctccc taacggggg caattttttat  7620
tgataacaaa agtaacttcg agcttgtcta cctcctagct cgtaaattgc acgctgatag  7680
tctcccaatt gcgaaggacc aaaacgaaaa aacacccttt cgggtgtctt ttctggaatt  7740
tggtacgcag tactaggtat cgtgtaagta gcgaaggccc gtacgcgaga taaactgcta  7800
ggcaaccgcg actctacgac tggtgctcga tttaatttcg ctgacgtaaa gaaattatcg  7860
gcagtgcgtc aactgccgta tctttatctt aattaggtag ttggacaagc ccttgaaaga  7920
aatagcaaga gcctgcctct ctattgaagt cacggcgaaa gtcgggtaga aatcaaagaa  7980
agcagaaatt aaatcggagt aatactaagt tgggataact ccgtaactga ctacgccttt  8040
ctctagactt tacttgacca gatacactgt cttttgacacg ttgaaggatt agagcaatca  8100
aatccaagac tggctaagca cgaagcaact cttgagtgtt aaaaagttac ttcctgtatt  8160
cgggacgagg gtactagaag attgcaggga ctccgacgtt aagtaaatta caaagtaata  8220
agtatcgttc aggatcacgt taccgcaata agaagcgaga ataatataat ttccgaagtg  8280
cttaccccag tagtgactat tcctataacc cttctgagtg tccggaggcg gaaatttgcc  8340
acgaaagaga aagtatttcc ccgacaataa taaaggggcg ctcctcagct tttccacttg  8400
gttgggtaag ctaggcaact ctgaaaggag tttcggcgaa gtgaagccga cacctttgaa  8460
ttgttttagg ggcgttattc gagggcaatc ggagctaact tcaagactac ttctttgttg  8520
aatactaaat agtgcaaagg tcgtgtttcc tcaaggatac tccgctaaca atataggatt  8580
ccaatcagat tcagcactgg cggtacgggt gttgcggtga ggcgttcggg tttacggctc  8640
gaagctagca cggtaggaag cctgacaatc accaagcaaa agggccgtcg aaggcccaca  8700
agatacgaaa gctctcgaag ccttatcctt gaccgatcca cctatttagg cagttacgca  8760
caaaagctac ccaataatcc gtgacaggca caatatcacg gaacaaaacc gaaaactctc  8820
gtacacggtt aggttttcgc taggaagaat aaacctctat cttgattata agaaggctcc  8880
ccaagcaccc ccaaaaccga aatagcggtt tgcaataagg acaagttac gagtgtagac  8940
acgcagaatt atccagcctt tagtctttag gaaggcaaag ctattgtacg cggtagccgt  9000
cgtagcaatt taccaactgt agaattattg gacacacgta acaagggctt acagttgaag  9060
tttaataagg tcacacgcaa aaccgctaag gaataatcgc accgttagcg aaagaatatt  9120
tcagagcggt tagtaaaggt tgagtaaagt gagattccaa agtgagcctt tataaaaagt  9180
aaagagctat aataaaaccg tcgatcggaa aacaatcgcc tgaaatctca agcacgttg  9240
cctttctaac gtcgctaagg tttcgtaaac ccgtttgatt aggaagaaga ataagtaacc  9300
cgattaggtt tgagatcgcg ggttatcggt ttggattaaa agtggatacc agcggagtca  9360
acgccgacgc aaacgtacag tgatccaatc ctgttccacg gtcaagcaca atcagctagc  9420
aagatcttgg aatagagtcg ttgcaccgct ttgatttaca tgctctccat tgcacaacat  9480
tccggaagga ctggcttctc tgccatgatc ggataatgaa aaacatcagt atgccctgtc  9540
atttttcttt gggtgctctc aaataattgc cctcacgtta tcgtatgtga cgcgctcatc  9600
tatgctcgaa gtattccttg ttctcccatc ttttaataga aagtcttaa tgaacgttgc  9660
gttacgcagt gtatgaactc ttgtttata gggcagactt tggcgtggcc taagtgtgtt  9720
cgataagaag gcaaggacaa ctagctgacg cgctgtaata cggatattat ggcacggttg  9780
atacaaacgc tgatatcctg atttgctaat gtgcccaaca ctttagttga gtgccacgtt  9840
ccgactacaa gttgcttcaa gaggggaatt tggatttggc aatagccccc cgtttctacc  9900
```

-continued

```
tcaagaggcg acgagtatta accgcgccag ctttcggcac aagggccaaa gaagattcca    9960
atttcttatt cccgaataac ctccgaatcc ctgcgggaaa atcaccgacc gaatagccta   10020
gaagcaaggg ggaacagata ggtataatta gcttaagaga gtaccagccg tgacaacacc   10080
gtagtaacca caaacttacg ctggggcttc tttggcggat ttttacagat actaacaagg   10140
tgatttgaag taccttagtt gaggatttaa acgcgctatc cggtagtcta caaattggga   10200
aataccgttc aaagagggct agaattactt aaaagccttc acaccgcctg cgctatacgg   10260
gcccactctc ccgtttatcc gtccaagcgc aagcagggcg aacttccgct aagatattct   10320
tacgtgtaac gtagctaagt atcccaaata gctggcgtac gcgttgaaca ccgcctagag   10380
gatcgggagt cgccggacga gcgtgttatt ggggacttac gccagcgtag actacaacgg   10440
gcccagatta accctgcacg tattgccttg aataacgtac taatctctcc ggctctcgac   10500
aatctatcga gcgactcgat tatcaacggg tgtcttgcag ttctaatctc ttgccccgc    10560
ccgtaatagc ctccaagtga ttcaagatag taaagggcaa gagcttattc ggcgttgaag   10620
gatagcggac tttcggtcaa ccacaattcc ccactcgaca aaaccagccg tgcgaagaac   10680
tctgaaagta caagcaaccc aagagggctg agcctaattc cagctaattc ctaagtgagc   10740
taaagactcg aagtgacagc tattaataaa tagagcggga acgtcgaacg gtcgtgaaag   10800
taatagtaca acgggtatta acttactgag gatattgctt gaagctgtac cgttttattg   10860
ggtgaacgaa taagatccag caattcagcc aagaagcta ccaattttta gtttaagagt    10920
gtcacgtctg accctcgcgg tggatagccg aacgtagagc ttacgagcca gcggaaacag   10980
tagccgcagg ataagtaagg ggagtaagtg atcgaacgaa tcagaagtga caatatactt   11040
aggctggatc tcgtcccgtg aatcccaacc ctcaccaact acgagataag aggtaagcca   11100
gaaatcggca tggtggcgac caacgactgt tccccccctg taactaatcg ttccgtcaaa   11160
acctgactta cttcaaggcc aattccaagc gcaaacaata ccgtcctagt tcttcggtta   11220
agtttccgaa gtaggagtga gcctacctcc gtttgcgtct tgttaccact gacccagcta   11280
tttactttgt attgcctgca atcgaatttc tgaactctca gatagtgggg ataacgggaa   11340
agttcctata tttgcgaact aacttagccg tccacctcga agctacctac tcacacccac   11400
cccgcgcggg gtaaataagg cactaatccc agcttagagc ttgctagca cttagccaca    11460
agttaattaa cagttgtctg gtagtttggc ggtattagcg agatcctaga agcaaggcag   11520
agttagttct aacctaaagc cacaaataag acaggttgcc aaagcccgcc ggaaattaaa   11580
tcttgctcag ttcggtaacg gagtttccc                                     11609
```

```
SEQ ID NO: 12       moltype = AA  length = 1196
FEATURE             Location/Qualifiers
source              1..1196
                    mol_type = protein
                    note = chimeric STF (STF-V10-[Helix])
                    organism = synthetic construct
SEQUENCE: 12
MAVKISGVLK DGTGKPVQNC TIQLKARRNS TTVVVNTVGS ENPDEAGRYS MDVEYGQYSV     60
ILQVDGFPPS HAGTITVYED SQPGTLNDFL CAMTEDDARP EVLRRLELMV EEVARNASVV   120
AQSTADAKKS AGDASASAAQ VAALVTDATD SARAASTSAG QAASSAQEAS SGAEAASAKA   180
TEAEKSAAAA ESSKNAAATS AGAAKTSETN AAASQQSAAT SASTAATKAS EAATSARDAV   240
ASKEAAKSSE TNASSSAGRA ASSATAAENS ARAAKTSETN ARSSETAAER SASAAADAKT   300
AAAGSASTAS TKATEAAGSA VSASQSKSAA EAAAIRAKNS AKRAEDIASA VALEDADTTR   360
KGIVQLSSAT NSTSETLAAT PKAVKVVMDE TNRKAPLDSP ALTGTPTAPT ALRGTNNTQI   420
ANTAFVLAAI ADVIDASPDA LNTLNELAAA LGNDPDFATT MTNALAGKQP KNATLTALAG   480
LSTAKNKLPY FAENDAASLT ELTQVGRDIL AKNSVADVLE YLGAGENSGS ATDVMIQLAA   540
NDGFKFIGQC PDILTLRTIE PEKNGQRITL RQHTIGTGLG GGVFRAVLDG TGYTDDDGVV   600
IKTAGGSVWL RVNADKVNPF MFGATGVADD TAALQKMLEC GRAAELGTNV WKASNLELNN   660
KSCSLSGSGL HVSRIEQISG ATGALLTITQ DCSLIYLSDC GLYGDITAG TSGVTMETGN    720
PGGAPSYPFN TAPDVRRDLY ISNVHITGFD ELGFDYPETN FSVSTHGLFI RNIKKTGAKI   780
GTTDFTWTNL QIDTCGQECL VLDGAGNCRI IGAKLIWAGS ENETPYSGLR ISNSQNVNMT   840
GVELQDCAYD GLYIKNSTVA ISGLNTNRNS ASSNLSYHNM VFENSIVTVD GYVCRNYAAT   900
SLYDLNSQAG NVRCIGSDST VLINGIYESE VNSERLMGDN NLIQPYSGDL IINGLKNYYT   960
YTGSVKNNIP TFDGVVTTAT YVSAPSILGQ GNMLKLTQSN KDKLLFSDKV SRHGCTIGLV  1020
LIPSFTGATT MTAFTLGSGY SPSGNSAVMQ FIVNSSGVQT IAILLSGDGI TQTLTSDLTT  1080
EQALASGGVY HFAMGFAPGR LWWSIIDINT GRRIRRAYRQ PDLHAAFNSI FNSGTSSITA  1140
FSGPLAGDIA CEGAGSHVYV GGFSSESDYA ASRMYGLFTP VDLDKQYSFR TLNGNI      1196
```

```
SEQ ID NO: 13       moltype = DNA  length = 3588
FEATURE             Location/Qualifiers
source              1..3588
                    mol_type = other DNA
                    note = chimeric STF (STF-V10-[Helix])
                    organism = synthetic construct
SEQUENCE: 13
atggcagtaa agatttcagg agtcctgaaa gacggcacag aaaaccggt acagaactgc      60
accattcagc tgaaagccag acgtaacagc accacggtgg tggtgaacac ggtgggctca   120
gagaatccgg atgaagccgg cgttacagc atggatgtgg agtacggtca gtacagtgtc    180
atcctgcagg ttgacggttt tccaccatcg cacgccggga ccatcaccgt gtatgaagat   240
tcacaaccgg gacgctgaa tgattttctc tgtgccatga cggaggatga tgcccggccg    300
gaggtgctgc gtcgtcttga actgatggtg gaagaggtgg cgcgtaacgc gtccgtggtg   360
gcacagagta cggcagacgc gaagaaatca gccggcgatg ccagtgcatc agctgctcag   420
gtcgcggccg ttgtgactga tgcaactgac tcagcacgcg ccgccagcac gtccgccgga   480
caggctgcat cgtcagctca ggaagcgtcc tccggcgcag aagccagcag caaaaggcgt   540
actgaagcgg aaaaaagtgc cgcagccgca gagtcctcaa aaaacgcggc ggccaccagt   600
gccggtgcgg cgaaaacgtc agaaacgaat gctgcagcgt cacaacaatc agccgccacg   660
tctgcctcca ccgcggccac gaaagcgtca gaggccgcca cttcagcacg gatgcggtg    720
gcctcaaaag aggcagcaaa atcatcagaa acgaacgcat catcaagtgc cggtcgtgca   780
gcttcctcgg caacggcggc agaaaattct gccaggcgcg caaaaacgtc cgagacgaat   840
```

```
gccaggtcat ctgaaacagc agcggaacgg agcgcctctg ccgcggcaga cgcaaaaaca   900
gcggcggcgg ggagtgcgtc aacggcatcc acgaaggcga cagaggctgc gggaagtgcg   960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatgatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccgtc  1380
atgactaacg cgcttgcggg taaacaaccg aagaatgcga cactgacggc gctggcaggg  1440
cttttccacgg cgaaaaataa attaccgtat tttgcgaaaa atgatgccgc cagcctgact  1500
gaactgactc aggttggcag ggatattctg caaaaaatt ccgttgcaga tgttcttgaa  1560
taccttgggg ccggtgagaa ttcggggagc gctacagacg ttatgattca gctggcggca  1620
aatgatggct tcaaattcat cggtcagtgc ccagacatct tgaccctgcg tactatcgga  1680
ccggaaaaaa acggtcagcg tatcacctta cgtcaacata cgattggcac tggcttaggc  1740
ggtggcgttt tccgtgcagt tctggacggc actggctata ccgatgacga cggtgtggtg  1800
atcaaaaccg ctggggcag cgtttggctg cgtgtcaacg ctgacaaagt taacccgttc  1860
atgttcggtg caaccggagt agcggacgac accgccgccc tgcaaaaaat gctggaatgc  1920
ggtcgtgcgg cggaactggg gactaacgta tggaaagcaa gcaatctgga actgaacaac  1980
aaatcttgct ctctgtccgg cagtggcctg cacgtttctc gtattgaaca gatttccggt  2040
gcaaccggag cattgttaac catcacccaa gactgttcgc tgatttacct gtccgattgt  2100
ggcctgtacg gcgatggcat caccgcaggc acgagcggtg ttactatgga aacgggtaat  2160
ccgggtggcg ctccgtctta cccttcaat accgctccgg acgttcgtcg tgacctgtac  2220
atctctaacg tgcacatcac gggcttcgac gagctgggtt ttgattatcc ggaaaccaat  2280
ttctctgttt cgacgcatgg cctcttcatc cgtaacatca aaaaaacggg tgcaaagatt  2340
ggtactacgg acttcacttg gactaacctg caaattgata cttgcggtca ggaatgtctg  2400
gtgctggacg gtgcgggtaa ctgccgtatt attggtgcaa aactgatttg gcaggtagc  2460
gaaaacgaaa cgccatactc tggcctgcgt attagcaact ctcaaaatgt aaatatgact  2520
ggcgtagagt tacaagactg cgcgtatgat ggtttataca tcaagaactc tacggttgca  2580
atttcaggct taaacaccaa tcgcaatagc gcatcctcta atctgtccta ccataacatg  2640
gtattcgaaa attctattgt aactgttgat ggttatgtgt gtcgtaacta cgcggcgact  2700
tcgctgtacg acctgaacag ccaagcaggc aacgtccgtt gcatcggtag cgacagcacc  2760
gtttttaatca acggcatcta cgaaagcgaa gtcaatagcg agcgcctgat gggtgataac  2820
aacctgatcc agccgtatag tggtgatctg atcattaacg gcctgaaaaa ttactacacc  2880
tatactggta gcgtaaaaaa caacattccg accttcgacg gcgttgttac tacggcaacc  2940
tatgtgagcg caccgtctat tctgggtcag ggcaatatgc tcaaactgac ccagtctaat  3000
aaagacaaac tgttatttag cgataaagtt agccgtcatg gctgtaccat cggcttagtt  3060
ctgattccgt ccttttacggg cgcgaccact atgacgcgt tcacgctggg tagcggttac  3120
tctccatccg gtaactccgc cgtgatgcag ttcattgtta acagttccgg tgtacaaacc  3180
attgcgattt tattccggg cgacggtatt acccaaaccc tgaccagcga tctgaccacg  3240
gaacaagcac tggcgagcgg tggcgtgtat catttttgcaa tgggttttgc gccgggtcgt  3300
ttatggtgga gcattatcga tattaacacg ggcaggcgta ttcgtcgcgc ctaccgtcag  3360
ccggatctgc acgcggcgtt caactctatc ttcaactcgc cgtcgtc tattaccgca  3420
tttagcgggc cactggcggg cgacattgct tgcgaaggtg caggtagcca tgtatacgtt  3480
ggcggttttt cgtcggaatc tgattacgcg gctagccgta tgtatggcct gttcactccg  3540
gtcgatctgg acaagcagta tagcttccgt accctgaacg gtaacatt          3588
```

```
SEQ ID NO: 14           moltype = AA  length = 1131
FEATURE                 Location/Qualifiers
source                  1..1131
                        mol_type = protein
                        note = chimeric gpJ (1A2)
                        organism = synthetic construct
SEQUENCE: 14
MGKGSSKGHT PREAKDNLKS TQLLSVIDAI SEGPIEGPVD GLKSVLLNST PVLDTEGNTN    60
ISGVTVVFRA GEQEQTPPEG FESSGSETVL GTEVKYDTPI TRTITSANID RLRFTFGVQA   120
LVETTSKGDR NPSEVRLLVQ IQRNGGWVTE KDITIKGKTT SQYLASVVMG NLPPRPFNIR   180
MRRMTPDSTT DQLQNKTLWS SYTEIIDVKQ CYPNTALGV QVDSEQFGSQ QVSRNYHLRG   240
RILQVPSNYN PQTRQYSGIW DGTFKPAYSN NMAWCLWDML THPRYGMGKR LGAADVDKWA   300
LYVIGQYCDQ SVPDGFGGTE PRITCNAYLT TQRKAWDVLS DFCSAMRCMP VWNGQTLTFV   360
QDRPSDKTWT YNRSNVVMPD DGAPFRYSFS ALKDRHNAVE VNWIDPNNGW ETATELVEDT   420
QAIARYGRNV TKMDAFGCTS RGQAHRAGLW LIKTELLETQ TVDFSVGAEG LRHVPGDVIE   480
ICDDDYAGIS TGGRVLAVNS QTRTLTLDRE ITLPSSGTAL ISLVDGSGNP VSVEVQSVTD   540
GVKVKVSRVP DGVAEYSVWE LKLPTLRQRL FRCVSIREND DGTYAITAVQ HVPEKEAIVD   600
NGAHFDGEQS GTVNGVTPPA VQHLTAEVTA DSGEYQVLAR WDTPKVVKGV SFLLRLTVTA   660
DDDGSERLVST ARTTETTYRF TQLALGNYRL TVRAVNAWGQ QGDPASVSFR IAAPAAPSRI   720
ELTPGYFQIT ATPHLAVYDP TVQFEFWFSE KQIADIRQVE TSTRYLGTAL YWIAASINIK   780
PGHDYYFYIR SVNTVGKSAF VEAVGRASDD AEGYLDFFKG KITESHLGKE LLEKVELTED   840
NASRLEEFSK EWKDASDKWN AMWAVKIEQT KDGKHYVAGI GLSMEDTEEG KLSQFLVAAN   900
RIAFIDPANG NETPMFVAQG NQIFMNDVFL KRLTAPTITS GGNPPAFSLT PDGKLTAKNA   960
DISGNVNANS GTLNNVTINE NCRVLGKLSA NQIEGDLVKT VGKAFPRDSR APERWPSGTI  1020
TVRVYDDQPF DRQIVIPAVA FSGAKHEKEH TDIYSSCRLI VRKNGAEIYN RTALDNTLIY  1080
SGVIDMPAGH GHMTLEFSVS AWLVNNWYPT ASISDLLVVV MKKATAGITI S          1131

SEQ ID NO: 15           moltype = DNA  length = 3393
FEATURE                 Location/Qualifiers
source                  1..3393
                        mol_type = other DNA
                        note = chimeric gpJ (1A2)
```

```
                  organism = synthetic construct
SEQUENCE: 15
atgggtaaag gaagcagtaa ggggcatacc ccgcgcgaag cgaaggacaa cctgaagtcc    60
acgcagttgc tgagtgtgat cgatgccatc agcgaagggc cgattgaagg tccggtggat   120
ggcttaaaaa gcgtgctgct gaacagtacg ccggtgctgg acactgaggg gaataccaac   180
atatccggtg tcacggtggt gttccgggct ggtgagcagg agcagactcc gccggaggga   240
tttgaatcct ccggctccga gacggtgctg gtacggaagt gaaatatga cacgccgatc   300
acccgcacca ttacgtctgc aaacatcgac cgtctgcgct ttaccttcgg tgtacaggca   360
ctggtggaaa ccacctcaaa gggtgacagg aatccgtcgg aagtccgcct gctggttcag   420
atacaacgta acggtggctg gaaagacatc accattaaggg caaaaccacc   480
tcgcagtatc tggcctcggt ggtgatgggt aacctgccgc cgcgcccgtt taatatccgg   540
atgcgcagga tgacgccgga cagcaccaca gaccagctgc agaacaaaac gctctggtcg   600
tcatacactg aaatcatcga tgtgaaacag tgctaccga cacggcact ggtcggcgtg   660
caggtggact cggagcagtt cggcagccag caggtgagcc gtaattatca tctgcgcgag   720
cgtattctgc aggtgccgtc gaactataac ccgcagacgc ggcaatacag cggtatctgc   780
gacggaacgt ttaaaccggc atacagcaac aacatgcct ggtgtctgtg ggatatgctg   840
acccatccgc gctacggcat ggggaaacgt cttggtgcgg cggatgtgga taaatgggcg   900
ctgtatgtca tcggccagta ctgcgaccag tcagtgccga acggctttgg cggcacggag   960
ccgcgcatca cctgtaatgc gtacctgacc acacagcgta aggcgtggga tgtgctcagc  1020
gatttctgct cggcgatgcg ctgtatgccg gtatggaacg ggcagacgct gacgttcgtg  1080
caggaccgac cgtcggataa gacgtggacc tataaccgca gtaatgtggt gatgccggat  1140
gatggcgcgc cgttccgcta cagcttcagc gccctgaagg accgccataa tgccgttgag  1200
gtgaactgga ttgacccgaa caacggctgg gagacggcga cagagcttgt tgaagatacg  1260
caggccattg cccgttacgg tcgtaatgtt acgaagatgg atgcctttgg ctgtaccagc  1320
cgggggcagg cacaccgcgc cgggctgtgg ctgattaaaa cagaactgct ggaaacgcag  1380
accgtggatt tcagcgtcgg cgcagaaggg cttcgccatg taccgggcga tgttattgaa  1440
atctgccgatg atgactatgc cggtatcagc accggtggtc gtgtgctggc ggtgaacagc  1500
cagacccgga cgctgacgct cgaccgtgaa atcacgctgc catcctccgg taccgcgctg  1560
ataagcctgg ttgacggaag tggcaatccg gtcagcgtgg aggttcagtc cgtcaccgac  1620
ggcgtgaagg taaaagtgag ccgtgttcct gacggtgttg ctgaatacag cgtatgggag  1680
ctgaagctgc cgacgctgcg ccagcgactg ttccgctgcg tgagtatccg tgagaacgac  1740
gacggcacgt atgccatcac cgccgtgcag catgtgccgg aaaaagaggc catcgtggat  1800
aacggggcgc actttgacgg cgaacagagt ggcacggtga atggtgtcac gccgccagcg  1860
gtgcagcacc tgaccgcaga gtcactgca gacagcgggg aatatcaggt gctgcgcgca  1920
tgggacacac cgaaggtggt gaagggcgtg agtttcctgc tccgtctgac cgtaacgacg  1980
gacgacggca gtgagcggct ggtcagcacg gcccggacga cggaaaccac ataccgcttc  2040
acgcaactgg cgctggggaa ctacaggctg acagtccggg cggtaaatgc gtgggggcag  2100
cagggcgatc cggcgtcgt atcgttccgg attgccgcac cggcagcacc gtcgaggatt  2160
gagctgaccg cgggctattt tcagataacc gccacgccgc atcttgccgt ttatgacccg  2220
acggtacagt ttgagttctg gttctcgaa aagcagattg cggatatcag acaggttgaa  2280
accagcacgc gttatcttgg tacgcgctg tactggatag ccgccagtat caatatcaaa  2340
ccgggccatg attattactt ttatatccgc agtgtgaaca ccgttggcaa atcggcattc  2400
gtggaggccg tcggtcgggc gagcgatgat gcggaaggtt acctggattt tttcaaaggc  2460
aagataaccg aatcccatct cggcaaggag ctgctggaaa aagtcgagct gacggaggat  2520
aacgccagca gactggagga gttttcgaaa gagtggaagg atgccagtga taagtggaat  2580
gccatgtggg ctgtcaaaat tgagcagacc aaagacggca acattatgt cgcgggtatt  2640
ggcctcagca tggaggacac ggaggaaggc aaactgagtc agtttctggt tgccgccaat  2700
cgtatcgcat ttattgaccc ggcaaacggg aatgaaacgc cgatgtttgt ggcgcagggc  2760
aaccagatat tcatgaacga cgtgttcctg aagcgcctga cggccccac cattaccagc  2820
ggcggcaatc ctccggcctt ttccctgaca ccggacggaa agctgaccgc taaaaatgcg  2880
gatatcagcg gtaacgtgaa tgcgaactcc gggacgctca acaacgtcac gattaacgag  2940
aactgtcggg ttctgggaaa attgtccgcg aaccagattg aaggcgatct cgttaaaaca  3000
gtgggcaaag cttttccccg ggactcccgt gcaccggagc ggtggccatc aggaaccatt  3060
accgtcaggg tttatgacga tcagccgttt gaccggcaga ttgttattcc ggcggtggca  3120
ttcagcggcg ctaaacatga gaaagagcat actgatattt actcctcatg ccgtctgata  3180
gtgcggaaaa acggtgctga aatttataac cgtaccgcgc tggataatac gctgatttac  3240
agtggcgtta tgatatgcc tgccggtcac ggtcacatga cactggagtt ttcggtgtca  3300
gcatggctgg taaataactg gtatcccaca gcaagtatca gcgatttgct ggttgtggtg  3360
atgaagaaag ccactgcagg catcacgatt agc                               3393

SEQ ID NO: 16           moltype = DNA   length = 2352
FEATURE                 Location/Qualifiers
source                  1..2352
                        mol_type = other DNA
                        note = p2.3 pri-ori p1319
                        organism = synthetic construct
SEQUENCE: 16
gttgtccata tttgctacgt ttaaatcaaa actggtgaaa ctcacccacg gatttgcact    60
gacgaaaaac atattttcga taaacccttt agggaaatat gctaagtttt caccgtaaca   120
cgccacatct tgactatata tgtgtagaaa ctgccggaaa tcgtcatggt attctgacca   180
gagcgatgag aacgtttcag tttgctcatg gaaaacggtg taacaagggt gaacactatc   240
ccatatcacc agttcaccgt ctttcattgc catacgaaac tccggatgtg cattcatcag   300
gcgggcaaga atgtgaataa aggccggata aacttgtgc ttattttct ttacggtttt   360
taaaaaggcc gtaatatcca gttgaacggt ttggttataa gtgcactgaa caactgactg   420
gaatgcctca aaatgttctt tacgatgcca ttgacttata tcaactgtag tatatccagt   480
gatttttttc tccattttag attccttagc ttgcgaaatc tcgataactc aaaaaatagt   540
agtgatctta tttcattatg gtgaaagttg tcttacgtgc aacattttcg caaaagttg   600
gcgctttatc aacactgtcc ctcctgttca gctactgacg gtactgcgga actgactaaa   660
gtagtgcgta acggcaaaag caccgccgga catcttttgt tgcaatggct gtctaccctg   720
```

```
tctacctgag taaagaaaaa tacatttaat tcagtacatt aacttgggta gacagccttt    780
ttttactgtc tacctactat ctaccctctc tacctgattt tacctgaatc agacagggag    840
gtagatacgg ggtagatagt ggataaaagc actctacccc actgaaagcc gcgccattac    900
tggcatggtg gccagtaagg tagataaggt agacaagggg aggcacaact caaaactttt    960
taaacgaggg ggtaaaacgc agaccaaaac gatctcaaga agatcatctt attaatcaga   1020
taaaatattt ctagatttca gtgcaattta tctcttcaaa tgtagcacgt ttagccgaac   1080
gccccaaaaa gcctcgcttt cagcacctgc cgtttccttt cttttcagag ggtatttaa   1140
ataaaaacat taagttatga cgaagaagaa cggaaacgcc ttaaaccgga aaattttcat   1200
aaatagcgaa aacccgcgag gtcgccgccc cgtaaccagt cggatcaccg gaaagtacct   1260
gtaaagtgat aatgattatc atcttcatat cacaacgtgc gtaaagggac tagtggatac   1320
tagtattata cctagcactg agcacgggta gcaccagaag tctatagcat gtgcatacct   1380
ttggtcgaaa aaaaaagccc gcactgtcag gtgcgggctt ttttcagtgt ttccttgccg   1440
gattatttgt agagttcatc catacccgtgc gtgataccac tagcggtaac gaactctaat   1500
aacaccatgt ggtcgcgctt ttcgttcgga tccttagaca gttttagactg ggtgacagg   1560
tagtggttat ccggcagtaa aacaggagcg tctccaatcg gagtgttttg ttggtaatga   1620
tccgcaagct ggacgctacc atcttcaacg ttatgtcgaa ttttaaagtt agctttgata   1680
ccgttctttt gtttgtctgc ggtgatgtaa acgttatggg agttgaagtt atattccagt   1740
ttgtggccta aaatattgcc gtcctctttg aaatcaatgc ctttcagttc aatacgattc   1800
accagagtgt caccttcaaa tttaacctct gcacggggttt tatacgtgcc atcgtctttg   1860
aaagaaatgg tgcgctcctg tacataacct tccggcattg cagatttgaa gaaatcatgt   1920
tgcttcatgt ggtcagggta acgagaaaaa cactgaacac cataggtcag ggtagtcacc   1980
agagtaggcc acggtactgg taattttcca gtagtgcaga tgaatttcag ggtcagctta   2040
ccgttggttg catcgccttc accttcacca cgaacactga atttatgacc gttaacatcg   2100
ccgtccagtt caactaagat cggaacaaca ccagtaaata attcctcacc tttactcatg   2160
gcttcctttc tcctctttaa tgaaaactta cgccccgccc tgccactcat cgcagtattg   2220
ttgtaattca ttaagcattc tgccgacatg gaagccatca caaacggcat gatgaacttg   2280
gatcgccagt ggcattaaca ccttgtcgcc ttgcgtataa tatttttccca tagtgaaaac   2340
gggggcgaag aa                                                      2352

SEQ ID NO: 17      moltype = DNA  length = 2778
FEATURE            Location/Qualifiers
source             1..2778
                   mol_type = other DNA
                   note = p2.8 p15a, p1220
                   organism = synthetic construct
SEQUENCE: 17
gttgtccata tttgctacgt ttaaatcaaa actggtgaaa ctcacccacg gatttgcact     60
gacgaaaaac atattttcga taaaccctttt agggaaatat gctaagtttt caccgtaaca   120
cgccacatct tgactatata tgtgtagaaa ctgccgaaaa tcgtcatgat attctgacca   180
gagcgatgag aacgtttcag tttgctcatg gaaaacggtg taacaagggt gaacactatc   240
ccatatcacc agttcaccgt cttttcattg catacgaaac tccggatgtg cattcatcag   300
gcgggcaaga atgtgaataa aggccggata aaacttgtgc ttattttttct ttacggtttt   360
taaaaaggcc gtaatatcca gttgaacggt tggttatag ggcgactgag caactgactg   420
gaatgcctca aaatgttctt tacgatgcca ttgacttata tcaactgtag tatatccagt   480
gattttttc tccattttag attccttagc ttgcgaaatc tcgataactc aaaaatagt    540
agtgatctta tttcattatg gtgaaagttg tcttacgtgc aacattttcg caaaaagttg   600
gcgctttatc aacactgtcc ctcctgttca gctactgacg atctgcgga actgactaaa   660
gtagtgcgta acggcaaaag caccgccgga catctcgcgct agcggagtgt atactggctt   720
actatgttgg cactgatgag ggtgtaagtg aagtgcttca tgtggcagga gaaaaaaggc   780
tgcatcggtg cgtcagcaga atatgtgata caggatatat tccgcttcct cgctcactga   840
ctcgctacgc tcggtcgttc gactgtggcg agcggaaatg gcttacgaac ggggctgaga   900
tttcctggaa gatgccagga agatacttaa cagggaagtg agagggtcgc ggcaaagccg   960
tttttccata ggctccgccc ccctgacaag catcacgaaa tctgacgctc aaatcagtgg  1020
tggcgaaacc tgacaggact ataaagatac caggcgtttc cccctggcgg ctccctcgtg  1080
cgctctcctg ttcctgcctt tcggttttgcc ggtgtcattc tctgttact gccgagttg   1140
tctcattcca cgcctgacac tcagttccgg gtaggcagtt cgctccaagc tggactgtat  1200
gcacaaaccc ccgttcagt ccgaccgctg cgccttatcc ggtaactatc gtcttgagtc  1260
caacccggaa agacatgcaa aagcaccact ggcagcagcc actggtaatt gatttagagg  1320
agttagtctt gaagtcatgc gccggataag gctaaactga aaggacaagt tttggcgaaa  1380
gcgctcctcc aagcagtta cctcggtcca aagagttggt agctcagagg accttcgaaa  1440
aaccgccctg caaggcggtt ttttcgtttt cagagcaaga gattacgcgc agaccaaaac  1500
gatctcaagc caaaaagcct cgctttcagc acctgccgtt tcctttcttt tcagagggta  1560
ttttaaataa aaacattaag ttatgacgaa gaagaacgga aacgccttaa accggaaaat  1620
tttcataaat agcgaaaacc cgcgaggtcg ccgccccgta accgga tcaccggaaa       1680
gtacctgtaa agtgataatg attatcatct tcatatcaca acgtgcgtaa agggactagt  1740
ggatactagt attataccta gcactgagca cgggtagcac cagaagtcta tagcatgtgc  1800
atacctttgg tcgaaaaaaa aagcccgcac tgtcaggtgc gggctttttt cagtgttttcc 1860
ttgccggatt atttgtagag ttcatccata ccgtgcgtga taccactagc ggtaacgaac  1920
tctaataaca ccatgtggtc gcgcttttcg ttcggatcct tagacagttt agactgggtg  1980
gacaggtagt ggttatccgg cagtaaaaca ggagcgtctc caatcggagt gttttgttgg  2040
taatgatccg caagctggac gctaccatct tcaacgttat gtcgaatttt aaagttagct  2100
ttgataccgt tcttttgttt gtctgcggtg atgtaaacgt tatgggagtt gaagttatat  2160
tccagttttgt ggcctaaaat attgccgtcc tctttgaaat caatgccttt cagttcaata  2220
cgattcacca gagtgtcacc ttcaaattta acctctgcac gggttttata cgtgccatcg  2280
tctttgaaag aaatggtgcg ctcctgtaca taaccttccg gcattgcaga tttgaagaaa  2340
tcatgttgct tcatgtggtc agggtaacga gaaaaacact gaacaccata ggtcaggta   2400
gtcaccagag taggccacgg tactggtaat tttccagtag tgcagatgaa tttcagggtc  2460
agcttaccgt tggttcatc gccttccact tcaccacgaa cactgaattt atgaccgtta  2520
acatcgccgt ccagttcaac taagatcgga acaaccag taaataattc ctcacccttta  2580
```

```
ctcatggctt cctttctcct ctttaatgaa aacttacgcc ccgccctgcc actcatcgca   2640
gtattgttgt aattcattaa gcattctgcc gacatggaag ccatcacaaa cggcatgatg   2700
aacttggatc gccagtggca ttaacacctt gtcgccttgc gtataatatt tcccatagt    2760
gaaaacgggg gcgaagaa                                                 2778

SEQ ID NO: 18          moltype = DNA   length = 27
FEATURE                Location/Qualifiers
source                 1..27
                       mol_type = other DNA
                       note = primase RBS 1
                       organism = synthetic construct
SEQUENCE: 18
cttgattaaa cgattctggt gtaaaaa                                       27

SEQ ID NO: 19          moltype = DNA   length = 27
FEATURE                Location/Qualifiers
source                 1..27
                       mol_type = other DNA
                       note = primase RBS 2
                       organism = synthetic construct
SEQUENCE: 19
cttgactaaa cgattcagtg gcaaaaa                                       27

SEQ ID NO: 20          moltype = DNA   length = 27
FEATURE                Location/Qualifiers
source                 1..27
                       mol_type = other DNA
                       note = primase RBS 3
                       organism = synthetic construct
SEQUENCE: 20
cgtgattaaa cgatcccgtt ttcaaaa                                       27

SEQ ID NO: 21          moltype = DNA   length = 27
FEATURE                Location/Qualifiers
source                 1..27
                       mol_type = other DNA
                       note = primase RBS 4
                       organism = synthetic construct
SEQUENCE: 21
cgtgattaaa cgatactgtt gcaaaaa                                       27

SEQ ID NO: 22          moltype = DNA   length = 27
FEATURE                Location/Qualifiers
source                 1..27
                       mol_type = other DNA
                       note = primase RBS 5
                       organism = synthetic construct
SEQUENCE: 22
cgtgactaaa cgatccgggg ggcaaaa                                       27

SEQ ID NO: 23          moltype = DNA   length = 27
FEATURE                Location/Qualifiers
source                 1..27
                       mol_type = other DNA
                       note = primase RBS 6
                       organism = synthetic construct
SEQUENCE: 23
cttgattaaa cgatccaggt ttaaaaa                                       27

SEQ ID NO: 24          moltype = DNA   length = 27
FEATURE                Location/Qualifiers
source                 1..27
                       mol_type = other DNA
                       note = primase RBS 7
                       organism = synthetic construct
SEQUENCE: 24
cttgactaaa cgatactgtt tccaaaa                                       27

SEQ ID NO: 25          moltype = DNA   length = 11789
FEATURE                Location/Qualifiers
source                 1..11789
                       mol_type = other DNA
                       note = plasmid lacz6 pri-ori, p1322
                       organism = synthetic construct
SEQUENCE: 25
ctaatctctt gccccgccc gtaatagcct ccaagagatt gaagatagta aagggcaaga    60
gctgattcgg cgttgaagga tagcggactt tcggtcaacc acaattcccc actcgacaaa   120
accagccgtg cgaataactc tgaaagtaca agcaacccaa gagggctgag cctaaactca   180
gctaattcct aagtgagcta aagactcgaa gtgacagctc ttaataaata gagcgggaac   240
```

```
gtcgaacggt cgtgaaagta atagtacaac gggtattaac ttactgagga tattgcttga  300
agctgtaccg tttttattggg tgaacgaata agatccagca attcagccaa agaagctacc  360
aattttttagt ttaagagtgt cacgtctgac ctcgcgggta gattgccgaa cgtagagctt  420
acgagccagc ggaaacagta gccgcaggat aagtaagggg agtaagtgat cgaacgaatc  480
agaagtgaca atatacttag gctggatctc gtcccgtgca tcccaaccct caccaactac  540
gagataagag gtaagccaaa aatcgacttg gtggcgacca acgactgttc cccccctgta  600
actaatcgtt ccgtcaaaac ctgacttact tcaaggccaa ttccaagcgc aaacaatacc  660
gtcctagttc ttcggttaag tttccgaagt aggagtgagc ctacctccgt ttgcgtcttg  720
ttaccactga cccagctatt tactttgtat tgcctgcact cgaatttctg aactctcaga  780
tagtggggat aacgggaaag ttcctatatt tgcgaactaa cttagccgtc cacctcgaag  840
ctacctactc acacccaccc cgcgcggggt aaataaggca ctaatcccag ctgagagctg  900
gcgtagcact tagccacaag ttaattaaca gttgtctggt agtttggcgg tattaggaag  960
atcctagaag caaggcagag ttagttctaa cctaaagcca caaataagac aggttgccaa 1020
agcccgccgg aaattaaatc ttgctcagtt cggtaacgga gtttccctcc cgcgtactta 1080
attcccaata agaaacgcgc ccaagtccta tcaggcaaaa ttcagcccct tcccgtgtta 1140
gaacgagggt aaaaatacaa gccgattgaa caagggttgg gggcttcaaa tcgtcgttta 1200
ccccactttta caacggagat taagtagttc accctatagt acgaagcaga actatttcga 1260
ggggcgtgca ataatcgaat cttctgcggt tgacttaaca cgctagggac gtgccctcga 1320
ttcaatcgaa ggtactccta ctcagactgc ctcacaccca gctagtcact gagcgataaa 1380
attgacccgc cctctaggga agcgagtacg tcccaagggg ctccggacag ggctatatag 1440
gagagtttga tctcgcccg acaactgcaa ccctcaactc cctagataa tattgttagc 1500
cgaagttgca cgacccgccg tccacggact gctcttaggg tgtggctcct taatctgaca 1560
acgtgcaacc cctatcgaag tcgattgttt ctgcgaaagg tgttgtccta atagtcccga 1620
aatttggccc ttgtaggtgt gaaaccactt agcttcgcgc cgtagtccta aaggcccacc 1680
tattgacttt gtttcgggta gcactaggaa tcttaacaat ttgaatttgg acgtggaacg 1740
cgtacaccctt aatctccgaa taattctagg gatttggaag tcctctacgt tgacacacct 1800
acactgctcg aagtaaatat acgaataacg cgggcctcgc ggagccgttc cgaatcgtca 1860
cgtgttcgtt tactgttaat tggtggcaaa taagcaatat cgtagtccgt caggcccagc 1920
cctgttatcc acggcgttat ttgtcaaatt gcgtagaact ggattgactg cctgacaata 1980
cctaattatc ggtacgaagt cccgaatct gtcgggctat ttcactaata ctttccaaac 2040
gccccgtatc caagaagaac gaatttatcc acgctcccgt cttttgggacg aataccgcta 2100
caagtggaca gaggatcggt acgggcctct aataaatcca acactctacg ccctcttcaa 2160
gagctagaag aacagggtgc agttggaaag ggaattattt cgtaaggcga gccaataccg 2220
taattaattc ggaagagtta acacgattgg aagtaggaat agtttctaac cacggttact 2280
aatcctaata acggaacgct gtctgataga ttagtgtcag cgctcggtac caaagaaaaa 2340
taaaagacg ctgaaaagcg tctttttatt tttcggtcca gtgtaactca ggcaaaagca 2400
cgtaatattc gtactttctt cctccgtaag cgtcacccac attccttaaa gagtgcatgt 2460
gcatatttg ttatcaataa aaaaggccgc gatttgcggc cttattgttc gtcttgccgg 2520
attacgcccc gccctgccac tcatcgcagt attgttgtaa ttcattaagc attctgccga 2580
catggaagcc atcacaaacg gcatgatgaa cttggatcgc cagtggcatt aacaccttgt 2640
cgccttgcgt ataatatttt cccatagtga aaacgggggc gaagaagttg tccatatttg 2700
ctacgtttaa atcaaaactg gtgaaactca cccacggatt ggcactgacg aaaaacatat 2760
tttcgataaa ccctttaggg aaatatgcta agttttcacc gtaacacgcc acatcttgac 2820
tatatatgtg tagaaactgc cggaaatcgt cgtggtattc tgaccagagc gatgaaaacg 2880
tttcagtttg ctcatggaaa acggtgtaac aagggtgaac actatcccat atcaccagct 2940
caccgtcttt cattgccata cgaaactccg gatgtgcatt catcaggcgg gcaagaatgt 3000
gaataaaggc cggataaaac ttgtgcttat ttttcttac ggttttaaa aaggccgtaa 3060
tatccagctg aacggtttgg ttataggtgc actgagcaac tgactggaat gcctcaaaat 3120
gttctttacg atgccattga cttatatcaa ctgtagtata tccagtgatt ttttttctcca 3180
ttttagcttc cttagcttgc gaaatctcga taactcaaaa aatagtagtg atcttatttc 3240
attatgtga aagttgtctt acgtgcaaca ttttcgcaaa aagttggcgc tttatcaaca 3300
ctgtcggaat gacaaatggt tccaattatt gaacacccttt cggggtgttt ttttgtttct 3360
ggtttcccga ggcggccttt tgttgcaat ggctgtctac cctgtctacc tgagtaaaga 3420
aaaatacatt taattcagta cattaacttg ggtagacagc cttttttttac tgtctaccta 3480
ctatctaccc tctctacctg atttttacctg aatcagacag ggaggtagat acggggtaga 3540
tagtggataa aagcactcta cccccactgaa agccgcgcca ttactggcat ggtggccagt 3600
aagtagata aggtagacaa ggggaggcac aactcaaaac ttttttaaacg aggggtaaa 3660
acgcagacca aaacgatctc aagaagatca tcttattaat cagataaaat atttctagat 3720
ttcagtgcaa tttatctctt caaatgtagc accggcgcgc cgtgaccaat tattgaaggc 3780
cgctaacgcg gccttttttt gtttctggta tcccgaatgg agcgacttct ccccaaaaag 3840
cctcgctttc agcacctgtc gttttccttttc ttttcagagg gtattttaaa taaaaacatt 3900
aagttatgac gaagaagaac ggaaacgcct taaccggaa aatttcata aatagcgaaa 3960
acccgcgagg tcgccgcccc gtaacctgtc ggatcaccgg aaaggacccg taagtgata 4020
atgattatca tctacatatc acaacgtgcg taaagggtaa gtatgaaggt cgtgtactcc 4080
atcgctacca aattcagaa aacagacgct ttcgagcgtc ttttttcgtt ttggtcacga 4140
cgtacggtgg aagattcgtt accaattgac agctagctca gtcctaggta tatacataca 4200
tgcttgtttg tttgtaaact actgttttca ttaaagagga gaaggaagc catgtccatc 4260
tatcaggagt ttgttaacaa gtattccctg tctaaaaccc tgcgttttga actgatcccg 4320
cagggcaaaa cttttggaaaa cattaaagcg cgtggcctga ttctggatga cgaaaaacgt 4380
gcaaaggatt acaagaaagc taaacagatc atcgacaaat atcaccagtt ctttatcgaa 4440
gaaattctgt cgtcggtgtg catcagtgag gatctgttac agaattattc tgatgtatac 4500
tttaaactta aaagtccgaa tgacgataat ctgcaaaaag atttcaagtc agccaaagat 4560
accatcaaga aacagatctc agaatatatt aaagatagcg aaaagttcaa aaacctgttt 4620
aaccaaaacc tcattgatgc taagaaaggc caagaatctg acctgatctt atggctgaaa 4680
cagagcaaag ataacggcat tgaactgttc aaagctaata gcgacatcac cgatattgat 4740
gaagcgctcg aaatcatcaa gtctttcaaa ggctggacga cgtatttcaa aggttttcat 4800
gaaaaccgta agaatgtata ttcgagcaac gatattccga cctctattat ttatcgtatc 4860
gtggacgaca acctgccgaa gtttctggaa aacaaagcga aatatgaatc tctgaaagac 4920
aaagcaccgg aagctattaa ctatgaacag atcaagaaag atctggcgga agaactgacc 4980
```

```
ttcgacatcg actataaaac ctccgaagtt aaccagcgtg ttttctcact ggacgaggtt   5040
ttcgaaatcg ctaatttcaa caattacctg aatcaatctg gcatcaccaa attcaacacc   5100
attattggtg gcaaatttgt taacggcgaa acaccaagc gtaagggcat caacgaatac    5160
attaacctgt atagccaaca aatcaacgac aaaaccctga aaaagtataa aatgtccgtt   5220
ctgttaaac agatttatc ggacaccgaa tctaaatcct tcgtaattga taaactggaa     5280
gatgatagcg acgttgtcac cacgatgcag agcttttatg agcagattgc ggcgttcaaa   5340
accgtggaag agaaatctat taaagaaact ctgtccctgc tctttgacga cctcaaagcg   5400
cagaaactag atctgtctaa gatttacttt aaaaacgaca aatctctgac cgatctcagt   5460
caacaagttt tcgatgacta tagcgtgatc ggcacggcag ttttggaata catcacccaa   5520
caaatcgcgc cgaaaaatct ggacaacccg tccaagaagg aacagaaact gattgcaaag   5580
aaaacagaaa aagctaaata cctgagctta gaaactatca aactggcact tgaggaattt   5640
aataaacatc gtgatattga taaacagtgt cgtttgagg aaattctggc gaactttgcg    5700
gcaatcccga tgatcttcga cgaaattgct caaaacaaag acaatctggc gcagatctct   5760
atcaagtacc agaatcaggg taagaaagat ctgcttcaag catctgcgga ggacgatgtg   5820
aaagcaatta aagacttatt agatcagacg aataacttat tacacaagct caaaatcttc   5880
cacatcagcc agagcgagga caaggcgaac attctggata aagatgaaca cttctatctg   5940
gtgttcgaag aatgttactt cgaactggca aacatcgtcc ctctctacaa taaaatccgc   6000
aactacatca cgcagaagcc ttactctgac gagaaattca aactgaactt cgaaaacagc   6060
acgctggcga acggctggga taagaacaaa gagccggaca acaccgcaat cctgttcatc   6120
aaagacgaca aatactatct gggcgtaatg aacaagaaga caacaagat cttcgacgat    6180
aaagcgatca aagaaaacaa gggtgaaggc tataagaaaa tcgtgtacaa gctcctgccg   6240
ggtgcgaata aaatgttacc gaaagtgttc ttttccgcga aaagcatcaa attctacaac   6300
ccgtctgagg atattctgcg catccgcaat catgcacgc acactaaaaa cggtagcccg     6360
cagaaagggt atgaaaaatt cgaatttaat atagaggact gccgtaagtt catcgacttc   6420
tataaacaga gcatttccaa acatccgaaa tggaaagact tcggcttccg tttctctgac   6480
actcagcgct ataatagcat cgacgagttc taccgcagga tggagaatca gggctataaa   6540
ctgaccttcg agaacattag tgagtcgtac atcgactccg ttgtgaatca gggtaaactg   6600
tacctgtttc agatctataa taagacttt agccgcgtaca gcaaaggccg tccgaatctg    6660
cacacccttt actggaaagc attatttgac gaacgtaacc tgcaagatgt ggtgtataaa   6720
ctgaacggtg aggcggaact tttctaccgt aaacagagta tcccgaagaa aatcacgcat   6780
ccggcaaaag aagctattgc caacaaaaac aaagacaacc cgaagaaaga atcagtattc   6840
gaatatgacc tgatcaaaga taaacgtttc accgaagata agttcttttt ccactgtccg   6900
attaccatca acttcaaatc tagcggtgcg aacaagttca acgatgaaat taacttatta   6960
ctgaaagaga aagctaatga cgtacacatc ttatctattg atcgcggtga acgtcattta   7020
gcatactata cactggtaga tggtaaaggt aatattatta aacaggatac tttcaatatt   7080
atcggtaatg accgtatgaa aaccaactat cacgataagc tggcggcgat cgaaaaagat   7140
cgtgattctg cgcgtaaaga ttggaagaaa attaacaata tcaaagaaat gaagaaggc    7200
tatctgagcc aagtggtgca cgagatcgca aaactggtga ttgaatataa cgctatcgtg   7260
gttttcgaag atctgaactt tggtttaaa cgtggtcgct tcaaagtaga aaaacaggtg    7320
taccaaaaac tggaaaaaat gctgattgaa aaactgaact atctggtttt taagacaac    7380
gaatttgaca aaacgggtgg cgtactccgt gcctatcagc tgaccgctcc gttcgaaacg   7440
ttcaagaaaa tgggtaaaca aacggggatt atctattatg tgccagctgg tttcacctcc   7500
aagatttgtc cagttacggg cttcgttaac cagctgtgca cgaaatacga gagcgttagc   7560
aaatctcaag aattttttcag caaattcgac aagatctgct ataatctgga taaaggctat   7620
ttcgagttca gcttcgatta caaaaacttc ggcgataaag cggctaaagg taagtggact   7680
attgctagct ttggtagccg tctgattaac tttcgcaact ccgacaaaaa ccataattgg   7740
gacacgctg aagtgtatcc gaccaaagaa ctggaaaaat tactgaaaga ctattccatc    7800
gaatatggtc atgggagtg cattaaagcg gcgatttgcg gtgaatccga taagaaattt    7860
ttcgccaaac tgaccagcgt gcttaacacc attctgcaaa tgcgtaattc taaaacgggt   7920
acggagctga actacctgat ttctccggta gccgacgtta acggcaactt cttcgattct   7980
cgtcaagcac cgaaaaatat gccacaagac gcggatgcca acggtgcata ccatatcgtg   8040
ttaaaaggct taatgttatt aggccgtatc aagaataatc aggagggcaa gaaattaaat   8100
ctggttatca aaacgaaga atacttcgag ttcgttcaga atcgtaacaa ttaatgtatg    8160
cttaagcagc tcggtaccaa agacgaacaa taagacgctg aaaagcgtct ttttcgttt    8220
tggtcctgtt gcggcgcgat agtgtgaaca tgctatagac tctggtgct acccgactga    8280
caattaatca tccggctcgt ataatgctag caatttctac tgttgtagat cccgatgtac   8340
gcgcgcgtgg atgatcgaga cgaacaataa ggcctcccta acgggggcc ttttttattg     8400
ataacaaaag taacttcgag cttgtctacc tcctagcacc attattgcaa ttaataaaca   8460
actaacggac aattctacct aacagttttc atatatgacg agcagttaag tgatgagtaa   8520
aggtgaggaa ttatttactg gtgttgttcc gatcttagtt gaactggacg gcgatgttaa   8580
cggtcataaa ttcagtgttc gtggtgaagg tgaaggtgat gcaaccaacg gtaagctgac   8640
cctgaaattc atctgcacta ctggaaaatt accagtaccg tggcctactc tggtgactac   8700
cctgacctat ggtgttcagt gttttctctg ttaccctgac cacatgaagc aacatgattt   8760
cttcaaatct gcaatgccgg aaggttatgt acaggagcga accatttctt tcaaagtgac   8820
tgcacgtat aaaacccgtg cagaggttaa atttgaaggt gacactctgg tgaatctat     8880
tgaactgaaa gcattgatt tcaaagagga cggcaatatt ttaggccaca aactggaata   8940
taacttcaac tcccataacg tttacatcac cgcagacaaa cagaagaacg gtatcaaagc   9000
taacttcaaa attcgccata acgttgaaga tggtagcgta cagctggcgg atcattacca   9060
acagaacact ccgattggag atgctcctgt tttactgccg gataaccact acctgtccac   9120
ccagtctaaa ctgtcgaagg atcccgaacga aaagcgcgac cacatggtgt tattagagtt    9180
cgttaccgct agtggtatca cgcacggtat ggatgaactc tacaaataag acgaacaata   9240
aggggagcgg gaaccgctc cctttttta ttgataacaa agtaaattg cacgctgata       9300
gtctcccaat tgcgaaggac caaaacgaaa aacacccctt tcgggtgtct tttctggaat   9360
ttgcgcga gtactaggta tcgtgtaagt agcgaaggcc gtacgcgag ataaactgct        9420
aggcaaccgc gactctacga ctggtgctcg atttaatttc gctgacgtaa agaaattatc   9480
ggcagtgcgt caactgccgt atctttatct taattaggta gttggacaag ccccttgaaag   9540
aaatagcaag agcctgcctc tctattgaag tcacggcgaa agtcgggtag aaatcaaaga   9600
aagcagaaat taaatcggag taacactaag gtgggataac tccgtaactg actacgcctt   9660
tctctagact ttacttgacc agatacactg tctttgacac gttgaaggat tagagcaatc   9720
```

-continued

```
aaatccaaga ctggctaagc acgaagcaac tcttgagtgt taaaaagtta tctcctgtat    9780
tcgggaagcg ggtactagaa gattgcaggg actccgacgt taagtaaatt acaaagtaat    9840
aagtatcgtt caggatcacg ttaccgcaat aagaagcgag aataatataa tttccgaagt    9900
gcttacccca gtagtgacta ttcctataac ccttctgagt gtccggaggc ggaaatttgc    9960
cacgaaagag aaagtatttc cccgacaata ataaagggcg gctcctcagc ttttccactt   10020
ggttgggtaa gctaggcaac tctgaaagga gtttcggcga attgaagccg acagctttga   10080
attgttttag gggcgttatt cgagggcaat cggagctaac ttcaagacta cttctttgtt   10140
gaatactaaa tagtgcaaag gtcgtgtttc ctcaaggata ctccgctaac aatataggat   10200
tccaatcaga ttcagcactg gcggtacggg tgttgcggtg aggcgttcgg gtttacggct   10260
cgaagctagc acggtaggaa gcctgacaat caccaagcaa aagggccgtc gaaggcccac   10320
aagtacgaa agctctcgaa gccttatcct tgaccgatcc acctatttag gcagttacgc   10380
acaaaagcta cccaataatc cgtgacaggc acaatatcac ggaacaaaac cgaaactct    10440
cgtacacggt taggttttcg ctaggaagaa taaacctcta tcttgattat aagaaggctc   10500
cccaagcacc cccaaaaccg aaatagcggt ttgcaataga cgaagtta cgagtgtaga    10560
cacgcagaat tatccagcct ttagtcttta ggaaggcaaa gctattgtac gcggtagccg   10620
tcgtagcaat ttaccaactg tagaattatt ggacacacgt aggaagggct tacagttgaa   10680
gtttaataag gtcacacgca aaaccgctaa ggaataatcg caccgttagc gaaagaatat   10740
ttcagagcgg ttagtaaagg ttgagtaaag tgagattcca aagtgagcct ttataaaaag   10800
taaagagcta taataaaacc gtcgagcaga aaacaatcgc ctgaaatctc aagcacgttg   10860
cccttttctaa cgtcgctaag gtttcgtaaa cccgtttgat taggaagaag aataagtaac   10920
ccgattaggt ttgagatcgc gggttatcgg tttggattaa aagtggatac cagcggagtc   10980
aacgccgacg caaacgtaca gtgatccaat cctgttcgac ggtcaagcac aatcagctcg   11040
caagatcttg gaatagtgtg cccaacagtt tagttgaggg ccacgttccg actacaagtt   11100
gcttcaagag gggaatttgg atttggcaat agccccccgt ttctacctca agaggcgacg   11160
agtattaacc gcgccagctg tcggcacaag ggccaaagaa gattccaatt tcttattccc   11220
gaataacctc cgaatccctg cgggaaaatc accgaccgaa tagcctagaa gcaaggggga   11280
acagataggt ataattagct taagagagta ccagccgtga caacagcgta gtaaccacaa   11340
acttacgctg gggcttcttt ggcggatttt tacagatact aacaaggtga tttgaagtac   11400
cttagttgag gatttaaacg cgctatccgg taatctccaa attgggaaat accgttcaaa   11460
gagggctaga attacttaaa agccttcaca ccgcctgcc tatacgcgcc cactctcccg   11520
tttatccgtc caagcggaag cagggcgatc ctccgctaag atattcttac gtgtaacgta   11580
gctaagtatc ccaaatagct ggcgtacgcg ttgaacaccg cctagaggat cgtgactcgc   11640
cggacgagcg tgttattggg gacttacgcc agcgtagact acaacgcgcc cagattaacc   11700
ctgcacgtat tgccttgaat aacgtactaa tctctccggc tctcgacaat ctatcgagcg   11760
actcgattat caacgggtgt cttgcagtt                                       11789

SEQ ID NO: 26          moltype = DNA  length = 27
FEATURE                Location/Qualifiers
source                 1..27
                       mol_type = other DNA
                       note = primase RBS 11
                       organism = synthetic construct
SEQUENCE: 26
cttgattaaa cgattctgtg ttcaaaa                                          27

SEQ ID NO: 27          moltype = DNA  length = 12299
FEATURE                Location/Qualifiers
source                 1..12299
                       mol_type = other DNA
                       note = plasmid LacZ6 p15a, p780
                       organism = synthetic construct
SEQUENCE: 27
ctaatctctt gccccgccc gtaatagcct ccaagagatt gaagatagta aagggcaaga      60
gctgattcgg cgttgaagga tagcggactt tcggtcaacc acaattcccc actcgacaaa    120
accagccgtg cgaataactc tgaaagtaca agcaacccaa gagggctgag cctaaactca    180
gctaattcct aagtgagcta aagactcgaa gtgacagctc ttaataaata gagcgggaac    240
gtcgaacggt cgtgaaagta atagtacaac gggtattaac ttactgagga tattgcttga    300
agctgtaccg ttttattggg tgaacgaata agatccagca attcagccaa agaagctacc    360
aattttagt ttaagagtgt cacgtctgac ctcgcgggta gattgccgaa cgtagagctt     420
acgagccagc ggaaacagta gccgcaggat aagtaaggggg agtaagtgat cgaacgaatc   480
agaagtgaca atatacttag gctggatctc gtcccgtgaa tcccaaccct caccaactac    540
gagataagag gtaagccaaa aatcgacttg gtggcgacca acgactgttc cccccctgta    600
actaatcgtt ccgtcaaaac ctgacttact tcaaggccaa ttccaagcgc aaacaatacc    660
gtcctagttc ttcggttaag tttccgaagt aggagtgagc ctaccctccgt ttgcgtcttg    720
ttaccactga cccagctatt tactttgtat tgcctgcaat cgaatttctg aactctcaga    780
tagtggggat aacgggaaag ttcctatatt tgcgaactaa cttagccgtc cacctcgaag    840
ctacctactc acacccaccc cgcgcggggt aaataaggca ctaatcccag ctgagagctg    900
gcgtagcact tagccaaagc ttaattaaca gttgtctggt agttggcgg tattaggaag     960
atcctagaag caaggcagta ttagttctaa cctaaagcca caataagac aggttgccaa    1020
agcccgccgg aaattaaatc ttgctcagtt cggtaacgga gttccctcc cgcgtactta    1080
attcccaata gaaaacgcgc ccaagtccta tcaggcaaaa ttcagcccct tcccgtgtta   1140
gaacgagggt aaaaatacaa gccgattgaa caagggttgg ggggcttcaaa tcgtcgttta   1200
ccccacttta caacggagat taagtagttc acctatagt acgaagcaga actatttcga    1260
ggggcgtgca ataatcgaat cttctgcggt tgacttaaca cgctagggac gtgccctaga   1320
ttcaatcgaa ggtactccta ctcagactgc ctcacaccca gctagtcact gagcgataaa   1380
attgacccgc cctctaggga agcgagtacg tcccaaaggg ctccggacag ggctatatag   1440
gagagttgta tctcgccccg acaactgcaa ccctcaactc ccttagataa tattgttagc   1500
cgaagttgca cgaccgcggg tccacggact gctcttaggg tgtggctcct taatctgaca   1560
acgtgcaacc cctatcgaag tcgattgttt ctgcgaaagg tgttgtccta atagtcccga   1620
```

-continued

```
aatttggccc ttgtaggtgt gaaaccactt agcttcgcgc cgtagtccta aaggcccacc 1680
tattgacttt gtttcgggta gcactaggaa tcttaacaat ttgaatttgg acgtggaacg 1740
cgtacacctt aatctccgaa taattctagg gatttggaag tcctctacgt tgacacacct 1800
acactgctcg aagtaaatat acgaataacg cgggcctcgc ggagccgttc cgaatcgtca 1860
cgtgttcgtt tactgttaat tggtggcaaa taagcaatat cgtagtccgt caggcccagc 1920
cctgttatcc acggcgttat ttgtcaaatt gcgtagaact ggattgactg cctgacaata 1980
cctaattatc ggtacgaagt ccccgaatct gtcgggctat ttcactaata ctttccaaac 2040
gccccgtatc caagaagaac gaatttatcc acgctcccgt ctttgggacg aataccgcta 2100
caagtggaca gaggatcggt acgggcctct aataaatcca acactctacg ccctcttcaa 2160
gagctagaag aacagggtgc agttggaaag ggaattattt cgtaaggcga gccaataccg 2220
taattaattc ggaagagtta acacgattgg aagtaggaat agtttctaac cacgttact 2280
aatcctaata acgaacgct gtctgataga ttagtgtcag cgctcggtac caagaaaaa 2340
taaaaagacg ctgaaaagcg tctttttatt tttcggtcca gtgtaactca ggcaaaagca 2400
cgtaatattc gtactttctt cctccgtaag cgtcacccac attccttaaa gagtgcatgt 2460
gcatattttg ttatcaataa aaaaggccgc gatttgcggc cttattgttc gtcttgccgg 2520
attacgcccc gccctgccac tcatcgcagt attgttgtaa ttcattaagc attctgccga 2580
catggaagcc atcacaaacg gcatgatgaa cttggatcgc cagtggcatt aacacctgt 2640
cgccttgcgt ataatatttt cccatagtga aaacggggc gaagaagttg tccatatttg 2700
ctacgtttaa atcaaaactg gtgaaactca cccacggatt ggcactgacg aaaaacatat 2760
tttcgataaa ccctttaggg aaatatgcta agttttcacc gtaacacgcc acatcttgac 2820
tatatatgtg tagaaactgc cggaaatcgt cgtggtattc tgaccagagc gatgaaaacg 2880
tttcagtttg ctcatggaaa acggtgtaac aagggtgaac actatcccat atcaccagct 2940
caccgtcttt cattgccata cgaaactccg gatgtgcatt catcaggcgg gcaagaatgt 3000
gaataaaggc cggataaaac ttgtgcttat ttttctttac ggttttaaaa aaggccgtaa 3060
tatccagctg aacggtttgg ttataggtgc actgagcaac tgactggaat gcctcaaaat 3120
gttctttacg atgccattga cttatatcaa ctgtagtata tccagtgatt tttttctcca 3180
ttttagcttc cttagcttgc gaaatctcga taactcaaaa aatagtagtg atcttatttc 3240
attatggtga aagttgtctt acgtgcaaca ttttcgcaaa aagttggcgc tttatcaaca 3300
ctgtcggaat gacaaatggt tccaattatt gaacacccctt cggggtgttt ttttgtttct 3360
ggtttcccga ggccggcctg cgctagcgga gtgtatactg gcttactatg ttggcactga 3420
tgagggtgta agtgaagtgc ttcatgtggc aggagaaaaa aggctgcatc ggtgcgtcag 3480
cagaatatgt gatacaggat atattccgct tcctcgctca ctgactcgct acgctcggtc 3540
gttcgactgt ggcgagcgga aatggcttac gaacggggcg gagatttcct ggaagatgcc 3600
aggaagatac ttaacaggga agtgagaggg tcgcggcaaa gccgttttc cataggctcc 3660
gccccctga caagcatcac gaaatctgac gctcaaatca gtggtggcga aacctgacag 3720
gactataaag ataccaggcg tttccccctg gcggctccct cgtgcgctct cctgttcctg 3780
cctttcggtt tgccggtgtc attcctctgt tacggccgag tttgtctcat tccacgcctg 3840
acactcagtt ccgggtaggc agttcgctcc aagctggact gtatgcacga acccccgtt 3900
cagtccgacc gctgcgcctt atccggtaac tatcgtcttg agtccaaccc ggaaagacat 3960
gcaaaagcac cactgcagc agccactggt aattgattta gaggagttag tcttgaagtc 4020
atgcgccgga taaggctaaa ctgaaaggac aagtttttggc gactgcgctc ctccaagcca 4080
gttacctcgg ttcaaagagt tggtagctca gagaaccttc gaaaaccgc cctgcaaggc 4140
ggttttttcg ttttcagagc aaagagattac gcgcagacca aagatctc aagaagatca 4200
tcttattaat cagataaaat atttctagat ttcagtgcaa tttatctctt caaatgtagc 4260
accggcgcgc cgtgaccaat tattgaaggc cgctaacgcg gccttttttt gtttctggta 4320
tcccgaatgg agcgacttct ccccaaaaag cctcgctttc agcacctgtc gtttcctttc 4380
ttttcagagg gtatttttaaa taaaaacatt aagttatgac gaagaagaac ggaaacgcct 4440
taaaccggaa aattttcata aatagcgaaa acccgcgagg tcgccgcccc gtaacctgtc 4500
ggatcaccga aaaggacccg taagtgata atgattatca tctacatatc acaacgtgcg 4560
taaagggtaa gtatgaaggt cgtgtactcc atcgctacca aattcagaa acagacgct 4620
ttcgagctgtc ttttttcgtt ttggtcacga cgtacggtgg aagattcgtt accaattgac 4680
agctagctca gtcctaggta tatacataca tgcttgtttg tttgtaaact actgttttca 4740
ttaaagagga gaaggaagc catgtccatc tatcaggagt ttgttaacaa gtattccctg 4800
tctaaaaccc tgcgttttga actgatcccg cagggcaaaa ctttgaaaaa cattaaagcg 4860
cgtggcctga ttctgatga cgaaaaacgt gcaaaggatt acaagaaagc taaacagatc 4920
atcgacaaat atcaccagtt ctttatcgaa gaaattctgt cgtcggtgtg catcagtgag 4980
gatctgttac agaattattc tgatgtatac tttaaactta aaaagtccga tgacgataat 5040
ctgcaaaaag atttcaagtc agccaaagat accatcaaga aacagatctc agaatatatt 5100
aaagatagcg aaaagttcaa aaacctgttt aaccaaaacc tcattgatgc taagaaaggc 5160
caagaatctg acctgatctt atggctgaaa cagagcaaag ataacggcat tgaactgttc 5220
aaagctaata gcgacatcac cgatattgat gaagcgctcg aaatcatcaa gtctttcaaa 5280
ggctggacga cgtatttcaa aggttttcat gaaaaccgta agaatgtata ttcgagcaac 5340
gatattccga cctctattat ttatcgtatc gtggacgaca acctgccgaa gtttctggaa 5400
aacaaagcga aatatgaatc tctgaaagac aaagcaccgt agctattaa ctatgaacag 5460
atcaagaaag atctgcggga agaactgacc ttcgacatcg actataaaac ctccgaagtt 5520
aaccagcgtg ttttctcact ggacgaggtt ttcgaaatcg ctaatttcaa caattacctg 5580
aatcaatctg gcatcaccaa attcaacacc attattggtg gcaaatttgt taacggcgaa 5640
aacaccaagc gtaagggcat caacgaatac attaacctgt atagccaaca aatcaacgac 5700
aaaccctga aaaagtataa aatgtccgtt ctgttaaa agattttatc ggacaccgaa 5760
tctaaatcct tcgtaattga taaactgaaa gatgatagcg acgttgtcac cacgatgcag 5820
agcttttatg agcagattgc ggcgttcaaa accgtgaaag agaaatctat taagaaact 5880
ctgtccctgc tctttgacga cctcaaagcg cagaaactag atctgtctaa gatttacttt 5940
aaaaacgaca aatctctgac cgatctcagt caacaagttt tcgatgacta tagcgtgatc 6000
ggcacggcga ttttggaata catcacccaa caaatcgcag gacaaccg 6060
tccaagaagg aacaggaact gattgcaaag aaaacagaaa aagctaaata cctgagctta 6120
gaaactatca aactggcact tgaggaattt aataaaatc gtgatattga taacagtgt 6180
cgttttgagg aaattctggc gaactttgcg caatcccga tgatcttcga cgaaattgct 6240
caaaacaaag acaatctggc gcagatctct atcaagtacc agaatcaggg taagaaagat 6300
ctgcttcaag catctgcgga ggacgatgtg aaagcaatta aagacttatt agatcagacg 6360
```

```
aataacttat tacacaagct caaaatcttc cacatcagcc agagcgagga caaggcgaac   6420
attctggata aagatgaaca cttctatctg gtgttcgaag aatgttactt cgaactggca   6480
aacatcgtcc ctctctacaa taaaatccgc aactacatca cgcagaagcc ttactctgac   6540
gagaaattca aactgaactt cgaaaacagc acgctggcga acggctggga taagaacaaa   6600
gagccggaca acaccgcaat cctgttcatc aaagacgaca aatactatct gggcgtaatg   6660
aacaagaaga acaacaagat cttcgacgat aaagcgatca aagaaaacaa gggtgaaggc   6720
tataagaaaa tcgtgtacaa gctcctgccg ggtgcgaata aaatgttacc gaaagtgttc   6780
ttttccgcga aaagcatcaa attctacaac ccgtctgagg atattctgcg catccgcaat   6840
catagcacgc acactaaaaa cggtagcccg cagaaagggt atgaaaaatt cgaatttaat   6900
atagaggact gccgtaagtt catcgacttc tataaacaga gcatttccaa acatccggaa   6960
tggaaagact tcggcttccg tttctctgac actcagcgct ataatagcat cgacgagttc   7020
taccgcgaag tggagaatca gggctataaa ctgaccttcg agaacattag tgagtcgtac   7080
atcgactccg ttgtgaatca gggtaaactg tacctgtttc agatctataa taaagacttt   7140
agcgcgtaca gcaaaggccg tccgaatctg cacacccttt actggaaagc attatttgac   7200
gaacgtaacc tgcaagatgt ggtgtataaa ctgaacggtg aggcggaact tttctaccgt   7260
aaacagagta tcccgaagaa aatcacgcat ccggcaaaag aagctattgc caacaaaaac   7320
aaagacaacc cgaagaaaga atcagtattc gaatatgacc tgatcaaaga taaacgtttc   7380
accgaagata agttcttttt ccactgtccg attaccatca acttcaaatc tagcggtgcg   7440
aacaagttca acgatgaaat taacttatta ctgaaagaga aagctaatga cgtacacatc   7500
ttatctattg atcgcggtga acgtcattta gcatactata cactggtaga tggtaaaggt   7560
aatattatta aacaggatac tttcaatatt atcggtaatg accgtatgaa aaccaactat   7620
cacgataagc tggcggcgat cgaaaaagat cgtgattctg gctgtaaaga ttggaagaaa   7680
attaacaata tcaaagaaat gaagaaggc tatctgagcc aagtggtgca cgagatcgca   7740
aaactggtga ttgaatataa cgctatcgtg gttttcgaag atctgaactt tggttttaaa   7800
cgtggtcgct tcaaagtaga aaaacaggtg taccaaaaac tggaaaaaat gctgattgaa   7860
aaactgaact atctggtttt taaagacaac gaatttgaca aaacgggtgg cgtactccgt   7920
gcctatcagc tgaccgctcc gttcgaaacg ttcaagaaaa tgggtaaaaa aacgggggatt   7980
atctattatg tgccagctgg tttcacctcc aagatttgtc cagttacggg cttcgttaac   8040
cagctgtacc cgaaatacga gagcgttagc aaatctcaag aattttttcag caaattcgac   8100
aagatctgct ataatctgga taaagtctat ttcgagttca gcttcgatta caaaaacttc   8160
ggcgataaag cggctaaagg taagtggact attgctagct ttggtagccg tctgattaac   8220
tttcgcaact ccgacaaaaa ccataattgg gacacgcgtg aagtgtatcc gaccaaagaa   8280
ctggaaaaat tactgaaaga ctattccatc gaatatggtc atgggagtg cattaaagcg   8340
gcgatttgcg gtgaatccga taagaaattt ttcgccaaac tgaccagcgt gcttaacacc   8400
attctgcaaa tgcgtaattc taaaacgggt acggagctgg actactgat ttctccggta   8460
gccgacgtta acggcaactt cttcgattct cgtcaagcac cgaaaaatat gccacaagac   8520
gcggatgcca acggtgcata ccatatcggc ttaaaaggct taatgttatt aggccgtatc   8580
aagaataatc aggagggcaa gaaattaaat ctggttatca aaaacgaaga atacttcgag   8640
ttcgttcaga atcgtaacaa ttaatgtatg cttaagcagc tcggtaccaa agacgaacaa   8700
taagacgctg aaaagcgtct tttttcgttt tggtcctgtt gcggcgcgat agtgtgaaca   8760
tgctatagac ttctggtgct acccgactga caattaatca tccggtcgt ataatgctag   8820
caatttctac tgttgtagat cccgatgtac gcgcgcgtgg atgatcgaga cgaacaataa   8880
ggcctcccta acgggggggcc tttttttattg ataacaaaag taacttcgag cttgtctacc   8940
tcctagcacc attattgcaa ttaataaaca actaacggac aattctacct aacagttttc   9000
atatatgacg agcagttaag tgatgagtaa aggtgaggaa ttatttactg gtgttgttcc   9060
gatcttagtt gaactggacg gcgatgttaa cggtcataaa ttcagtgttc gtggtgaagg   9120
tgaagtgat gcaaccaacg gtaagctgac cctgaaattc atctgcacta ctggaaaatt   9180
accagtaccg tggcctactc tggtgactac cctgacctat ggtgttcagt gttttctcg   9240
ttaccctgac cacatgaagc aacatgattt cttcaaatct gcaatgccgg aaggttatgt   9300
acaggagcgc accatttctt tcaaagacga tggcacgtat aaaacccgtg cagaggttaa   9360
atttgaaggt gacactctgg tgaatcgtat tgaactgaaa ggcattgatt tcaaagagga   9420
cggcaatatt ttaggccaca aactggaata aacttcaac tcccataacg tttacatcac   9480
cgcagacaaa cagaagaacg gtatcaaagc taacttcaaa attcgccata cgttgaaga   9540
tggtagcgta cagctggcgg atcattacca acagaacact ccgattggag atgctcctgt   9600
tttactgccg gataaccact acctgtccac ccagtctaaa ctgtcgaagg atccgaacga   9660
aaagcgcgac cacatggtgt tattagagtt cgttaccgct agtggtatca cgcacgtat   9720
ggatgaactc tacaaataag acgaacaata aggggagcgg gaaaccgctc cccttttta   9780
ttgataacaa aagtaaattg cacgctgata gtctcccaat tgcgaggac caaaacgaaa   9840
aaacacccctt tcgggtgtct tttctggaat ttggtaccga gtactaggta tcgtgtaagt   9900
agcgaaggcc cgtacgcgag ataaactgct aggcaaccgc gactctacga ctggtgctcg   9960
atttaatttc gctgacgtaa agaaattatc ggcagtgcgt caactgccgt atctttatct  10020
taattaggta gttggacaag cccttgaaag aaatagcaag agcctgcctc tctattgaag  10080
tcacggcgaa agtcgggtag aaatcaaaga aagcagaaat taaatcggag taacactaag  10140
gtgggataac tcctaactg actacgcctt tctctagact ttacttgacc agatacactg  10200
tctttgacac gttgaaggat tagagcaatc aaatccaaga ctggctaagc acgaagcaac  10260
tcttgagtgt taaaaagtta tctcctgtat tcgggaagcg ggtactagaa gattgcaggg  10320
actccgacgt taagtaaatt acaaagtaat aagtatcgtt caggatcacg ttaccgcaat  10380
aagaagcgag aataatataa tttccgaagt gcttacccca gtagtgacta ttcctataac  10440
ccttctgagt gtccggaggc ggaaatttgc cacgaaagag aaagtatttc cccgacaata  10500
ataaaggggc gctcctcagc ttttccactt ggttgggtaa gctaggcaac tctgaaagga  10560
gtttcggcga attgaagccg acagctttga attgttttag gggcgttatt cgagggcaat  10620
cggagctaac ttcaagacta cttctttgtt gaatactaaa tagtgcaaag gtcgtgtttc  10680
ctcaaggata ctccgctaac aatataggat tccaatcaga ttcagcactg gcggtacggg  10740
tgttgcgga aggcgttcgg gtttacggct cgaagctagc acggtaggca gcctgacaat  10800
caccaagcaa aagggccgtc gaaggccac aagatacgaa agctctcgaa gcctttatcct  10860
tgaccgatcc acctatttag gcagttacgc acaaaagcta cccaatatc cgtgacaggc  10920
acaatatcac ggaacaaaac cgaaaactct cgtacacggt taggttttcg ctaggaagaa  10980
taaacctcta tcttgattat aagaaggctc cccaagcacc cccaaaaccg aaatagcggt  11040
ttgcaataag ggacaagtta cgagtgtaga cacgcagaat tatccagcct ttagtcttta  11100
```

-continued

```
ggaaggcaaa gctattgtac gcggtagccg tcgtagcaat ttaccaactg tagaattatt    11160
ggacacacgt aggaagggct tacagttgaa gtttaataag gtcacacgca aaaccgctaa    11220
ggaataatcg caccgttagc gaaagaatat ttcagagcgg ttagtaaagg ttgagtaaag    11280
tgagattcca aagtgagcct ttataaaaag taaagagcta taataaaacc gtcgagcaga    11340
aaacaatcgc ctgaaatctc aagcacgttg cccttcctaa cgtcgctaag gtttcgtaaa    11400
cccgtttgat taggaagaag aataagtaac ccgattaggt ttgagatcgc gggttatcgg    11460
tttggattaa aagtggatac cagcggagtc aacgccgacg caaacgtaca gtgatccaat    11520
cctgttgcac ggtcaagcac aatcagctcg caagatcttg gaatagtgtg cccaacagtt    11580
tagttgaggg ccacgttccg actacaagtt gcttcaagag gggaatttgg atttggcaat    11640
agccccccgt ttctacctca agaggcgacg agtattaacc gcgccagctg tcggcacaag    11700
ggccaaagaa gattccaatt tcttattccc gaataacctc cgaatccctg cgggaaaatc    11760
accgaccgaa tagcctagaa gcaaggggga acagataggt ataattagct taagagagta    11820
ccagccgtga caacagcgta gtaaccacaa acttacgctg gggcttcttt ggcggatttt    11880
tacagatact aacaaggtga tttgaagtac cttagttgag gatttaaacg cgctatccgg    11940
taatctccaa attgggaaat accgttcaaa gagggctaga attacttaaa agccttcaca    12000
ccgcctgcgc tatacgcgcc cactctcccg tttatccgtc caagcggaag cagggcgatc    12060
ctccgctaag atattcttac gtgtaacgta gctaagtatc ccaaatagct ggcgtacgcg    12120
ttgaacaccg cctagaggat cgtgactcgc cggacgagcg tgttattggg gacttacgcc    12180
agcgtagact acaacgcgcc cagattaacc ctgcacgtat tgccttgaat aacgtactaa    12240
tctctccggc tctcgacaat ctatcgagcg actcgattat caacgggtgt cttgcagtt     12299
```

SEQ ID NO: 28        moltype = DNA   length = 11782
FEATURE              Location/Qualifiers
source               1..11782
                       mol_type = other DNA
                       note = plasmid LacZ6 pri-ori deltaGAAABCC, p1326
                       organism = synthetic construct
SEQUENCE: 28

```
ctaatctctt gccccgccc gtaatagcct ccaagagatt gaagatagta aagggcaaga      60
gctgattcgg cgttgaagga tagcggactt tcggtcaacc acaattcccc actcgacaaa    120
accagccgtg cgaataactc tgaaagtaca agcaacccaa gagggctgag cctaaactca    180
gctaattcct aagtgagcta aagactcgaa gtgacagctc ttaataaata gagcgggaac    240
gtcgaacggt cgtgaaagta atagtacaac gggtattaac ttactgagga tattgcttga    300
agctgtaccg ttttattggg tgaacgaata agatccagca attcagccaa agaagctacc    360
aattttttagt ttaagagtgt cacgtctgac ctcgcgggtg gattgccgaa cgtagagctt    420
acgagccagc ggaaacagta gccgcaggat aagtaagggg agtaagtgat cgaacgaatc    480
agaagtgaca atatacttag gctggatctc gtcccgtgaa tcccaaccct caccaactac    540
gagataagag gtaagccaaa aatcgacttg gtggcgacca acgactgttc ccccctgta     600
actaatcgtt ccgtcaaaac ctgacttact tcaaggccaa ttccaagcgc aaacaatacc    660
gtcctagttc ttcggttaag tttccgaagt aggagtgagc ctacctccgt ttgcgtcttg    720
ttaccactga cccagctatt tactttgtat tgcctgcaat cgaatttctg aactctcaga    780
tagtggggat aacgggaaag ttcctatatt tgcgaactaa cttagccgtc cacctcgaag    840
ctacctactc acacccaccc cgcgcggggt aaataaggca ctaatcccag ctgagagctg    900
gcgtagcact tagccacaag ttaattaaca gttgtctggt agtttggcgg tattaggaag    960
atcctagaag caaggcagag ttagttctaa cctaaagcca caaataagac aggttgccaa    1020
agcccgccgg aaattaaatc ttgctcagtt cggtaacgga gtttccctcc cgcgtactta    1080
attcccaata agaaacgcgc ccaagtccta tcaggcaaaa ttcagccct tcccgtgtta    1140
gaacgagggt aaaaatacaa gccgattgaa caagggttgg gggcttcaaa tcgtcgttta    1200
ccccactttta caacggagat taagtagttc accctatagt acgaagcaga actatttcga    1260
ggggcgtgca ataatcgaat cttctgcggt tgacttaaca cgctagggac gtgccctcga    1320
ttcaatcgaa ggtactccta ctcagactgc ctcacaccca gctagtcact gagcgataaa    1380
attgacccgc cctctaggga agcgagtacg tcccaaaggg ctccggacag ggctatatag    1440
gagagtttga tctcgccccg acaactgcaa ccctcaactc ccttagataa tattgttagc    1500
cgaagttgca cgaccgccg tccacggact gtcttaggg tgtggctcct taatctgaca    1560
acgtgcaacc cctatcgaag tcgattgttt ctgcgaaagt tgttgtccta atagtcccga    1620
aatttggccc ttgtaggtgt gaaaccactt agcttcgcgc cgtagtccta aaggcccacc    1680
tattgacttt gtttcgggta gcactaggaa tcttaacaat ttgaatttgg acgtggaacg    1740
cgtacaccttt aatctccgaa taattctagg gatttggaag tcctctacgt tgacacacct    1800
acactgctcg aagtaaatat acgaataacg cgggcctcgc ggagccgttc cgaatcgtca    1860
cgtgttcgtt tactgttaat tggtggcaaa taagcaatat cgtagtccgt caggcccagc    1920
cctgttatcc acggcgttat ttgtcaaatt gcgtagaact ggattgactg cctgacaata    1980
cctaattatc ggtacgaagt cccgaatct gtcgggctat ttcactaata ctttccaaac    2040
gccccgtatc caagaagaac gaatttatcc acgctcccgt ctttgggacg aataccgcta    2100
caagtggaca gaggatcggt acgggcctct aataaatcca acactctacg ccctcttcaa    2160
gagctagaag aacagggtgc agttggaaag ggaattattt cgtaaggcga gccaataccg    2220
taattaattc ggaagagtta acacgattgg aagtaggaat agtttctaac cacgttact    2280
aatcctaata acgaacgct gtctgataga ttagtgtcag cgctcggtac caaagaaaaa    2340
taaaaagacg ctgaaaagcg tcttttttatt tttcggtccg gtgtaactca ggcaaaagca    2400
cgtaatattc gtactttctt cctccgtaag cgtcacccac attccttaa gagtgcatgt    2460
gcatattttg ttatcaataa aaaaggccgc gatttgcggc cttattgttc gtcttgccgg    2520
attacgcccc gccctgccac tcatcgcagt attgttgtaa ttcattaagc attctgccga    2580
catggaagcc atcacaaacg gcatgatgaa cttggatcgc cagtggcatt aacaccttgt    2640
cgccttgcgt ataatatttt cccatagtga aaacgggggc gaagaagttg tccatatttg    2700
ctacgtttaa atcaaaactg gtgaaactca cccacgagt cgactgacg aaaaacatat    2760
tttcgataaa ccctttaggg aaatatgcta agttttcacc gtaacacgcc acatcttgac    2820
tatatatgtg tagaaactgc ggaaatcgt cgtggtattc tgaccagagc gatgaaaacg    2880
tttcagtttt ctcatggaaa acggtgtaac aagggtgaac actatcccat atcaccagct    2940
caccgtcttt cattgccata cgaaactccg gatgtgcatt catcaggcgg gcaagaatgt    3000
gaataaaggc cggataaaac ttgtgcttat ttttctttac ggtttttaaa aaggccgtaa    3060
```

```
tatccagctg aacggtttgg ttataggtgc actgagcaac tgactggaat gcctcaaaat   3120
gttctttacg atgccattga cttatatcaa ctgtagtata tccagtgatt ttttctccca   3180
ttttagcttc cttagcttgc gaaatctcga taactcaaaa aatagtagtg atcttatttc   3240
attatgtgta aagttgtctt acgtgcaaca ttttcgcaaa aagttggcgc tttatcaaca   3300
ctgtcggaat gacaaatggt tccaattatt gaacacccft tcggggtgttt ttttgtttcc   3360
cgaggccggc cttttgttgc aatggctgtc taccctgtct acctgagtaa agaaaaatac   3420
atttaattca gtacattaac ttgggtagac agccttttt tactgtctac ctactatcta   3480
ccctctctac ctgattttac ctgaatcaga cagggaggta gatacggggt agatagtgga   3540
taaaagcact ctaccccact gaaagcagcg ccattactgg catggtggcc agtaaggtag   3600
ataaggtaga caaggggagg cacaactcaa aactttttaa acgagggggt aaaacgcaga   3660
ccaaaacgat ctcaagaaga tcatcttatt aatcagataa aatatttcta gatttcagtg   3720
caatttatct cttcaaatgt agcaccggcg cgccgtgacc aattattgaa ggccgctaac   3780
gcggcctttt tttgtttctg gtatcccgaa tggagcgact tctccccaaa aagcctcgct   3840
ttcagcacct gtcgtttcct ttcttttcag agggtatttt aaataaaaac attaagttat   3900
gacgaagaag aacggaaacg ccttaaaccg gaaaattttc ataaatagcg aaaacccgcg   3960
aggtcgccgc cccgtaacct gtcggatcac cggaaaggac ccgtaaagtg ataatgatta   4020
tcatctacat atcacaacgt gcgtaaaggg taagtatgaa ggtcgtgtac tccatcgcta   4080
ccaaattcca gaaaacagac gctttcgagc gtcttttttc gttttggtca cgacgtacgg   4140
tggaagattc gttaccaatt gacagctagc tcagtcctag gtatatacat acatgcttgt   4200
ttgtttgtaa actactgttt tcattaaaga ggagaaagga agccatgtcc atctatcagg   4260
agtttgttaa caagtattcc ctgtctaaaa ccctgcgttt tgaactgatc ccgcagggca   4320
aaactttgga aaacattaaa gcgcgtggcc tgattctgga tgaacgaaaa cgtgcaaagg   4380
attacaagaa agctaaacag atcatcgaca aatatcacca gttctttatc gaagaaattc   4440
tgtcgtcggt gtgcatcagt gaggatctgt tacagaatta ttctgatgta tactttaaac   4500
ttaaaaagtc cgatgacgat aatctgcaaa aagatttcaa gtcagccaaa gataccatca   4560
agaaacagat ctcagaatat attaaagata gcgaaaagtt caaaaacctg tttaaccaaa   4620
acctcattga tgctaagaaa ggccaagaat ctgacctgat cttatggctg aaacagagca   4680
aagataacgg cattgaactg ttcaaagcta atagcgacat caccgatatt gatgaagcgc   4740
tcgaaatcat caagtctttc aaaggctgga cgacgtattt caaggttttt catgaaaacc   4800
gtaagaatgt atattcgagc aacgatattc cgacctctat tatttatcgt atcgtggacg   4860
acaacctgcc gaagtttctg gaaaacaaag cgaaatatga atctctgaaa gacaaagcac   4920
cggaagctat taactatgaa cagatcaaga aagatctggc ggaagaactg accttcgaca   4980
tcgactataa aacctccgaa gttaaccagc gtgttttctc actggacgag gttttcgaaa   5040
tcgctaattt caacaattac ctgaatcaat ctggcatcac caattcaaac accattattg   5100
gtggcaaatt tgttaacggc gaaaacacca agcgtaaggg catcaacgaa tacattaacc   5160
tgtatagcca acaaatcaac gacaaaaccc tgaaaaagta taaaatgtcc gttctgttta   5220
aacagatttt atcggacacc gaatctaaat ccttcgtaat tgataaactg gaagatgata   5280
gcgacgttgt caccacgatg cagagctttt atgagcagat tgcggcgttc aaaaccgtgg   5340
aagagaaatc tattaaagaa actctgtccc tgctctttga cgacctcaaa gcgcagaaac   5400
tagatctgtc taagatttac tttaaaaacg acaaatctct gaccgatctc agtcaacaag   5460
ttttcgatga ctatagcgtg atcggcacgg cagttttgga atacatcacc caacaaatcg   5520
cgccgaaaaa tctggacaac ccgtccaaga aggaacagga actgattgca aagaaaacag   5580
aaaaagctaa ataactgagc ttagaaacta tcaaactgac acttgaggaa tttaataaac   5640
atcgtgatat tgataaacag tgtcgttttg aggaaattct ggcgaacttt gcggcaatcc   5700
cgatgatctt cgacgaaatt gctcaaaaca aagacaatct ggcgcagatc tctatcaagt   5760
accagaatca gggtaagaaa gatctgcttc aagcatctgc ggaggacgat gtgaaagcaa   5820
ttaaagactt attagatcag acgaataact tattacacaa gctcaaaatc ttccacatca   5880
gccagagcga ggacaaggcg aacattctgg ataaagatga acacttctat ctggtgttcg   5940
aagaatgtta cttcgaactg gcaaacatcg tccctctcta caataaaatc cgcaactaca   6000
tcacgcagaa gccttactct gacgagaaat caaactgaa cttcgaaaac agcacgctgg   6060
cgaacggctg ggataagaac aaagagccgg acaacaccgc aatcctgttc atcaaagcag   6120
acaaatacta tctgggcgta atgaacaaga gaacaacaa gatcttcgac gataaagcga   6180
tcaaagaaaa caagggtgaa ggctataaga aaatcgtgta caagctcctg ccgggtgcga   6240
ataaaatgtt accgaaagtg ttcttttccg cgaaaagcat caaattctac aacccgtctg   6300
aggatattct gcgcatccgc aaatcatagca cgcacactaa aaacggtagc cgcagaaag   6360
ggtatgaaaa attcgaattt aaatatagagg actgccgtaa gttcatcgac ttctataaac   6420
agagcatttc caaacatccg gaatggaaag acttcggctt ccgttctctct gacactcagc   6480
gctataatag catcgacgag ttctaccgcg aagtggagaa tcagggctat aaaactgacct   6540
tcgagaacat tagtgagtcg tacatcgact ccgttgtaa tcagggtaaa ctgtacctgt   6600
ttcagatcta taataaagac ttagcgcgt acagcaaagg ccgtccgaat ctgcacaccgt   6660
tttactggaa agcattattt gacgaacgta acctgcaaga tgtggtgtat aaactgaacg   6720
gtgaggcgga acttttctac cgtaaacaga gtatcccgaa gaaaatcacg catccggcaa   6780
aagaagctat tgccaacaaa aacaaagaca acccgaagaa agaatcagta ttcgaatatg   6840
acctgactca agataaacgt ttcaccgaag ataagttctt tttccactgt ccgattacca   6900
tcaacttcaa atctagcggt gcgaacaagt tcaacgatga aattaactta ttactgaaag   6960
agaaagctaa tgacgtacac atcttatcta ttgatcgcgg tgaacgtcat ttagcatact   7020
atacactggt agatggtaaa ggtaatatta ttaaacagga tacatttcaat attatcggta   7080
atgaccgtat gaaaaccaac tatcacgata agctggcgga gatcgaaaaa gatcgtgatt   7140
ctgcgcgtaa agattcgaag aaaattaaca atatcaaaga aatgaaagaa ggctatctga   7200
gccaagtggt gcacgagatc gcaaaactgg tgattgaata taacgctatc gtggttttcg   7260
aagatctgaa ctttggtttt aaacgtggtc gcttcaaagt agaaaacag gtgtaccaaa   7320
aactggaaaa aatgctgatt gaaaactga actatctggt ttaaagac aacgaatttg   7380
acaaaacggg tggcgtactc cgtgcctatc agctgaccgc tccgtcgaa acgttcaaga   7440
aatgggtaa caaacgggg attatctatt atgtgccagc tgtgttcacc tccaagattt   7500
gtccagttac gggcttcgtt aaccagctgt acccgaaata cgagagcgtt agcaatctc   7560
aagaattttt cagcaaattc gacaagatct gctataatct ggataaaggc tatttcgagt   7620
tcagcttcga ttacaaaaac ttcggcgata agcggctaa aggtaagtgg actattgcta   7680
gctttggtag ccgtctgatt aactttcgca actccgacaa aaaccataat tgggacacgc   7740
gtgaagtgta tccgaccaaa gaactggaaa aattactgaa agactattcc atcgaatatg   7800
```

```
gtcatgggga gtgcattaaa gcggcgattt gcggtgaatc cgataagaaa ttttcgcca      7860
aactgaccag cgtgcttaac accattctgc aaatgcgtaa ttctaaaacg ggtacggagc      7920
tggactacct gatttctccg gtagccgacg ttaacggcaa cttcttcgat tctcgtcaag      7980
caccgaaaaa tatgccacaa gacgcggatg ccaacggtgc ataccatatc ggcttaaaag      8040
gcttaatgtt attaggccgt atcaagaata atcaggaagg caagaaatta aatctggtta      8100
tcaaaaacga agaatacttc ggagttcgttc agaatcgtaa caattaatgt atgcttaagc      8160
agctcggtac caaagacgaa caataagacg ctgaaaagcg tcttttttcg ttttggtcct      8220
gttgcggcgc gatagtgtga acatgctata gacttctggt gctacccgac tgacaattaa      8280
tcatccggct cgtataatgc tagcaatttc tactgttgta gatcccgatg tacgcgcaga      8340
tggatgatcg agacgaacaa taaggcctcc ctaacgtggg gccttttta ttgataacaa      8400
aagtaacttc gagcttgtct acctcctagc accattattg caattaataa acaactaacg      8460
gacaattcta cctaacagtt ttcatatatg acgagcagtt aagtgatgag taaaggtgag      8520
gaattattta ctggtgttgt tccgatctta gttgaactgg acggcgatgt taacggtcat      8580
aaattcagtg ttcgtggtga aggtgaaggt gatgcaacca acggtaagct gaccctgaaa      8640
ttcatctgca ctactggaaa attaccagta ccgtggccta ctctggtgac taccctgacc      8700
tatggtgttc agtgttttc tcgttaccct gaccacatga agcaacatga tttcttcaaa      8760
tctgcaatgc cggaaggta tgtacaggag cgcaccattt cttccaaaga cgatggcacg      8820
tataaaaccc gtgcagaggt taaattgaa ggtgacactc tggtgaatcg tattgaactg      8880
aaaggcattg atttcaaaga ggacggcaat atttaggcc acaaactgga atataacttc      8940
aactcccata acgtttacat caccgcagac aaacagaaga acggtatcaa agctaacttc      9000
aaaattcgcc ataacgttga agatgggtagc gtacagctgg cggatcatta ccaacagaac      9060
actccgattg gagatgctcc tgttttactg ccggataacc actacctgtc cacccagtct      9120
aaactgtcga aggatccgaa cgaaaagcgc gaccacatgg tgttattaga gttcgttacc      9180
gctagtggta tcacgcacgg tatggatgaa ctctacaaat aagacgaaca ataaggggag      9240
cgggaaaccg ctcccctttt ttattgataa caaaagtaaa ttgcacgctg atagtctccc      9300
aattgcgaag gaccaaaacg aaaaaacacc ctttcgggtg tcttttctgg aatttggtac      9360
cgagtactag gtatcgtgta agtagcgaag gccgtacgc gagataaaact gctaggcaac      9420
cgcgactcta cgactggtgc tcgatttaat ttcgctgacg taaagaaatt atcggcagtg      9480
cgtcaactgc cgtatctta tcttaattag gtagttggac aagcccttga agaaatagc      9540
aagagcctgc ctctctattg aagtcacggc gaaagtcggg tagaaatcaa agaaagcaga      9600
aattaaatcg gagtaacact aaggtgggat aactccgtaa ctgactacgc ctttctctag      9660
actttacttg accagataca ctgtctttga cacgttgaag gattagagca atcaaatcca      9720
agactggcta agcacgaagc aactcttgag tgttaaaaag ttatctcctg tattcggaa      9780
gcgggtacta gaagattgca gggactccga cgttaagtaa attacaaagt aataagtatc      9840
gttcaggatc acgttaccgc aataagaagc gagaataata taatttccga agtgcttacc      9900
ccagtagtga ctattcctat aacccttctg agtgtccgga ggcggaaatt tgccacgaaa      9960
gagaaagtat ttccccgaca ataataaagg ggcgctcctc agcttttcca cttggttggg     10020
taagctaggc aactctgaaa ggagtttcgg cgaattgaag ccgacagctt tgaattgttt     10080
taggggcgtt attcgagggc aatcggagct aacttcagaa ctacttcttt gttgaatact     10140
aaatagtgca aaggtcgtgt ttcctcaagg atactccgct aacaatatag gattccaatc     10200
agattcagca ctgcggtac gggtgttgcg gtgaggcgtt cgggtttacg gctcgaagct     10260
agcacggtag gaagcctgac aatcaccaag caaaagggcc gtcgaaggcc cacaagatac     10320
gaaagctctc gaagccttat ccttgaccga tccacctatt taggcagtta cgcacaaaag     10380
ctacccaata atccgtgaca ggcacaatat cacggaacaa aaccgaaaac tctcgtacac     10440
ggttaggttt tcgctaggaa gaataaacct ctatcttgat tataagaagg ctccccaagc     10500
acccccaaaa ccgaaatagc ggtttgcaat aagggacaag ttacgagtgt agacacgcag     10560
aattatccag cctttagtct ttaggaaggc aaagctattg tacgcggtag ccgtcgtagc     10620
aatttaccaa ctgtagaatt attggacaca cgtaggaagg gcttacagtt gaagtttaat     10680
aaggtcacac gcaaaaccgc taaggaataa tcgcaccgtt agcgaaagaa tatttcagg     10740
cggttagtaa aggttgagta aagtgagatt ccaaagtgag cctttataaa agtaaagag     10800
ctataataaa accgtcgagc agaaaacaat cgcctgaact ctcaagcacg ttgccctttc     10860
taacgtcgct aaggtttcgt aaacccgttt gattaggaag aagaataagt aacccgatta     10920
ggtttgagat cgcgggttat cggtttggat taaaagtgga taccagcgga gtcaacgccg     10980
acgcaaacgt acagtgatcc aatcctgttg cacggtcaag cacaatcagc tcgcaagatc     11040
ttggaatagt gtgcccaaca gtttagttga gggccacgtt ccgactacaa gttgcttcaa     11100
gaggggaatt tggatttggc aatagccccc cgtttctacc tcaagaggcg acgagtatta     11160
accgcgccag ctgtcggcac aagggccaaa gaagattcca atttcttatt cccgaataac     11220
ctccgaatcc ctgcgggaaa atcaccgacc gaatagccta gaagcaaggg ggaacagata     11280
ggtataatta gcttaagaga gtaccagccg tgacaacagc gtagtaacca caaacttacg     11340
ctggggcttc tttggcggat ttttacagat actaacaagg tgatttgaag taccttagtt     11400
gaggatttaa acgcgctatc cggtaatctc caaattggga aataccgttc aaagagggct     11460
agaattactt aaaagccttc acaccgcctg cgctatacgc gcccactctc ccgtttatcc     11520
gtccaagcgg aagcagggcg atcctccgct aagatattct tacgtgtaac gtagctaagt     11580
atcccaaata gctggcgtac gcgttgaaca ccgcctagag gatcgtgact cgccggacga     11640
gcgtgttatt ggggacttac gccagcgtag actacaacgc gcccagatta accctgcacg     11700
tattgccttg aataacgtac taatctctcc ggctctcgac aatctatcga gcgactcgat     11760
tatcaacggg tgtcttgcag tt                                             11782

SEQ ID NO: 29             moltype = DNA  length = 11915
FEATURE                   Location/Qualifiers
source                    1..11915
                          mol_type = other DNA
                          note = plasmid 4stx pri-ori deltagaaabcc, p1327
                          organism = synthetic construct
SEQUENCE: 29
ctaatctctt gccccgccc gtaatagcct ccaagagatt gaagatagta aagggcaaga        60
gctgattcgc cgttgaagga tagcggactt tcggtcaacc acaattcccc actcgacaaa      120
accagccgtg cgaataactc tgaaagtaca agcaacccaa gagggctgag cctaaactca      180
gctaattcct aagtgagcta aagactcgaa gtgacagctc ttaataaata gagcgggaac      240
```

```
gtcgaacggt cgtgaaagta atagtacaac gggtattaac ttactgagga tattgcttga  300
agctgtaccg ttttattggg tgaacgaata agatccagca attcagccaa agaagctacc  360
aattttttagt ttaagagtgt cacgtctgac ctcgcgggta gattgccgaa cgtagagctt  420
acgagccagc ggaaacagta gccgcaggat aagtaagggg agtaagtgat cgaacgaatc  480
agaagtgaca atatacttag gctggatctc gtcccgtgca tcccaaccct caccaactac  540
gagataagag gtaagccaaa aatcgacttg gtgcgcacca acgactgttc cccccctgta  600
actaatcgtt ccgtcaaaac ctgacttact tcaaggccaa ttccaagcgc aaacaatacc  660
gtcctagttc ttcggttaag tttccgaagt aggagtgagc ctacctccgt ttgcgtcttg  720
ttaccactga cccagctatt tactttgtat tgcctgcaat cgaatttctg aactctcaga  780
tagtggggat aacggaaaag ttcctatatt tgcgaactaa cttagccgtc cacctcgaag  840
ctacctactc acacccaccc cgcgcggggt aaataaggca ctaatcccag ctgagagctg  900
gcgtagcact tagccacaag ttaattaaca gttgtctggt agtttggcgg tattaggaag  960
atcctagaag caaggcagag ttagttctaa cctaaagcca caaataagac aggttgccaa 1020
agcccgccgg aaattaaatc ttgctcagtt cggtaacgga gtttccctcc cgcgtactta 1080
attcccaata agaaacgcgc ccaagtccta tcaggcaaaa ttcagcccct tcccgtgtta 1140
gaacgagggt aaaaatacaa gccgattgaa caagggttgg gggcttcaaa tcgtcgttta 1200
ccccacttta caacggagat taagtagttc accctatagt acgaagcaga actatttcga 1260
ggggcgtgca ataatcgaat cttctgcggt tgacttaaca cgctagggac gtgccctcga 1320
ttcaatcgaa ggtactccta ctcagactgc ctcacaccca gctagtcact gagcgataaa 1380
attgaccccgc cctctaggga agcgagtacg tcccaagggg ctccggacag ggctatatag 1440
gagagtttga tctcgcccccg acaactgcaa ccctcaactc cctagataa tattgttagc 1500
cgaagttgca cgacccgccg tccacggact gctcttaggt tgtggctcct taatctgaca 1560
acgtgcaacc cctatcgaag tcgattgttt ctgcgaaagt tgttgtccta atagtcccga 1620
aatttggccc ttgtaggtgt gaaaccactt agcttcgcgc cgtagtccta aaggcccacc 1680
tattgacttt gtttcgggta gcactaggaa tcttaacaat ttgaatttgg acgtggaacg 1740
cgtacacctt aatctccgaa taattctagg gatttgaaag tcctctacgt tgacacacct 1800
acactgctcg aagtaaatat acgaataacg cgggcctcgc ggagccgttc cgaatcgtca 1860
cgtgttcgtt tactgttaat tggtggcaaa taagcaatat cgtagtccgt caggcccagc 1920
cctgttatcc acggcgttat ttgtcaaatt gcgtagaact ggattgactg cctgacaata 1980
cctaattatc ggtacgaagt ccccgaatct gtcgggctat ttcactaata ctttccaaac 2040
gccccgtatc caagaagaac gaatttatcc acgctcccgt cttttgggacg aataccgcta 2100
caagtggaca gaggatcggt acgggcctct aataaatcca acactctacg ccctcttcaa 2160
gagctagaag aacagggtgc agttggaaag ggaattattt cgtaaggcga gccaataccg 2220
taattaattc ggaagagtta acacgattgg aagtaggaat agtttctaac cacggttact 2280
aatcctaata acgaaacgct gtctgataga ttagtgtcag cgctcggtac caaagaaaaa 2340
taaaagacg ctgaaaagcg tcttttttatt tttcggtcca gtgtaactca ggcaaaagca 2400
cgtaatattc gtactttctt cctccgtaag cgtcacccac attccttaaa gagtgcatgt 2460
gcatattttg ttatcaataa aaaaggccgc gatttgcggc cttattgttc gtcttgccgg 2520
attacgccc gccctgccac tcatcgcagt attgttgtaa ttcattaagc attctgccga 2580
catggaagcc atcacaaacg gcatgatgaa cttggatcgc cagtggcatt aacaccttgt 2640
cgccttgcgt ataatatttt cccatagtga aaacgggggc gaagaagttg tccatatttg 2700
ctacgtttaa atcaaaactg gtgaaactca cccacggatt ggcactgacg aaaaacatat 2760
tttcgataaa ccctttaggg aaatatgcta agttttcacc gtaacacgcc acatcttgac 2820
tatatatgtg tagaaaactgc cggaaatcgt cgtggtattc tgaccagagc gatgaaaacg 2880
tttcagtttg ctcatggaaa acggtgtaac aagggtgaac actatcccat atccaccagct 2940
caccgtcttt cattgccata cgaaactccg gatgtgcatt catcaggcgg gcaagaatgt 3000
gaataaaggc cggataaaac ttgtgcttat tttctcttac ggttttttaaa aaggccgtaa 3060
tatccagctg aacggtttgg ttataggtgc actgagcaac tgactggaat gcctcaaaat 3120
gttctttacg atgccattga cttatatcaa ctgtagtata tccagtgatt ttttttctcca 3180
ttttagcttc cttagcttgc gaaatctcga taactcaaaa aatagtagtg atcttatttc 3240
attatgtgaa aagttgtctt acgtgcaaca ttttcgcaaa aagttggcgc tttatcaaca 3300
ctgtcggaat gacaaatggt tccaattatt gaacacccctt cggggtgttt ttttgtttct 3360
ggtttcccga ggcggccctt tttgcaaggc tgtctaccct gtctacctga gtaaagaaaa 3420
atacatttaa ttcagtacat taacttgggt agacagcctt tttttactgt ctacctacta 3480
tctacccctct ctaccctgatt ttacctgaat cagacaggga ggtagatacg gggtagatag 3540
tggataaaag cactctaccc cactgaaagc agcgccatta ctggcatggt ggccagtaag 3600
gtagataagg tagacaaggg gaggcacaac tcaaaacttt ttaaacgagg gggtaaaacg 3660
cagaccaaaa cgatctcaag aagatcatct tattaatcag ataaaatatt tctagatttc 3720
agtgcaattt atctcttcaa atgtagcacc ggcgcgccgt gaccaattat tgaaggccgc 3780
taacgcggcc ttttttttgtt tctggtatcc cgaatggagc gacttctccc caaaaagcct 3840
cgctttcagc acctgtcgtt tccttttcttt tcagagggta ttttaaataa aaacattaag 3900
ttatgacgaa gaagaacgga aacgccttaa accggaaaat tttcataaat agcgaaaacc 3960
cgcgaggtcg ccgccccgta acctgtcgga tcaccggaaa ggaccccgtaa agtgataatg 4020
attatcatct acatatcaca gcatgcgtaa agggtaagta tgaaggtcgt gtactccatc 4080
gctaccaaat tccagaaaac agacgctttc gagcgtcttt tttcgttttg gtcacgacgt 4140
acggtgaaag attcgttacc aattgacagc tagctcagtc ctaggtatat acatacatgc 4200
ttgtttgttt gtaaactact gttttcatta aagaggagaa aggaagccat gtccatctat 4260
caggagtttg ttaacaagta ttccctgtct aaaacctgc gttttgaact gatcccgcag 4320
ggcaaaactt tggaaaacat taaagcgcgt ggcctgattc tggatgacga aaaacgtgaa 4380
aaggattaca agaaagctaa acagatcatc gacaaatatc accagttctt tatcgaagaa 4440
attctgtcgt cggtgtgcat cagtgaggat ctgttacaga attattctga tgtatacttt 4500
aaacttaaaa agtccgatga cgataatctg caaaaagatt tcagtcagc caaagatacc 4560
atcaagaaac agatctcaga atatattaaa gatagcgaaa agttcaaaaa cctgtttaac 4620
caaaacctca ttgatgctaa gaaaggccaa gaatctgacg tgatcttatg gctgaaacag 4680
agcaaagata acggcattga actgttcaaa gctaatagcg acatcaccga tattgatgaa 4740
gcgctcgaaa tcatcaagtc tttcaaaggc tggacgacgt atttcaaagg ttttcatgaa 4800
aaccgtaaga atgtatattc gagcaacgat attccgacct ctattattta tcgtatcgtg 4860
gacgacaacc tgccgaagtt tctggaaaac aaagcgaaat atgaatctct gaaagacaaa 4920
gcaccggaag ctattaacta tgaacagatc aagaaagatc tggcggaaga actgaccttc 4980
```

```
gacatcgact ataaaacctc cgaagttaac cagcgtgttt tctcactgga cgaggttttc  5040
gaaatcgcta atttcaacaa ttacctgaat caatctggca tcaccaaatt caacaccatt  5100
attggtggca aatttgttaa cggcgaaaac accaagcgta agggcatcaa cgaatacatt  5160
aacctgtata gccaacaaat caacgacaaa accctgaaaa agtataaaat gtccgttctg  5220
tttaaacaga ttttatcgga caccgaatct aaatccttcg taattgataa actggaagat  5280
gatagcgacg ttgtcaccac gatgcagagc ttttatgagc agattgcggc gttcaaaacc  5340
gtggaagaga aatctattaa agaaactctg tccctgctct ttgacgacct caaagcgcag  5400
aaactagatc tgtctaagat ttactttaaa aacgacaaat ctctgaccga tctcagtcaa  5460
caagttttcg atgactatag cgtgatcggc acggcagttt tggaatacat cacccaacaa  5520
atcgcgccga aaaatctgga caacccgtcc aagaaggaac aggaactgat tgcaaagaaa  5580
acagaaaaag ctaaatacct gagccttaga actatcaaac tggcacttga ggaatttaat  5640
aaacatcgtg atattgataa acagtgtcgt tttgaggaaa ttctggcgaa ctttgcggca  5700
atcccgatga tcttcgacga aattgctcaa aacaaagaca atctggcgca gatctctatc  5760
aagtaccaga atcagggtaa gaaagatctg cttcaagcat ctgcggagga cgatgtgaaa  5820
gcaattaaag acttattaga tcagacgaat aacttattac acaagctcaa aatcttccac  5880
atcagccaga gcgaggacaa ggcgaacatt ctggataaag atgaacactt ctatctggtg  5940
ttcgaagaat gttacttcga actggcaaac atcgtccctc tctacaataa aatccgcaac  6000
tacatcacgc agaagcctta ctctgacgag aaattcaaac tgaacttcga aaacagcacg  6060
ctggcgaacg gctgggataa gaacaaagag ccggacaaca ccgcaatcct gttcatcaaa  6120
gacgacaaat actatctggg cgtaatgaac aagaagaaca acaagatctt cgacgataaa  6180
gcgatcaaag aaaacaaggg tgaaggctat aagaaaatcg tgtacaagct cctgccgggt  6240
gcgaataaaa tgttaccgaa agtgttcttt tccgcgaaaa gcatcaaatt ctacaaccog  6300
tctgaggata ttctgcgcat ccgcaatcat agcacgcaca ctaaaaacgg tagcccgcag  6360
aaagggtatg aaaaattcga atttaatata gaggactgcc gtaagttcat cgacttctat  6420
aaacagagca tttccaaaca tccggaatgg aaagacttcg gcttccgttt ctctgacact  6480
cagcgctata atagcatcgc cgagttctac cgcgaagtgg agaatcaggg ctataaactg  6540
accttcgaga acattagtga gtcgtacatc gactccgttg tgaatcaggg taaactgtac  6600
ctgtttcaga tctataataa agactttagc gcgtacagca aaggccgtcc gaatctgcac  6660
accctttact ggaaagcatt atttgacgaa cgtaacctgc aagatgtggt gtataaactg  6720
aacggtgagg cggaacttt ctaccgtaaa cagagtacta cgaagaaaat cacgcatccg  6780
gcaaaagaag ctattgccaa caaaaacaaa gacaacccga agaaagaatc agtattcgaa  6840
tatgacctga tcaaagataa acgtttcacc gaagataagt tcttttttcc ctgtccgatt  6900
accatcaact tcaaatctag cggtgcgaac aagttcaacg atgaaattaa cttattactg  6960
aaagagaaag ctaattgatc gt acacatctta tctattgatc gcggtgaacg tcatttagca  7020
tactatacac tggtagatgg taaaggtaat attattaaac aggatacttt caatattatc  7080
ggtaatgacc gtatgaaaac caactatcac gataagctgg cggcgatcga aaaagatcgt  7140
gattctgcgc gtaaagattg gaagaaaatt aacaatatca aagaaatgaa agaaggctat  7200
ctgagccaag tggtgcacga gatcgcaaaa ctggtgattg aaatataacgc tatcgtggtt  7260
ttcgaagatc tgaactttgg ttttaaacgt ggtcgcttca aagtagaaaa acagtgtac  7320
caaaaactgg aaaaaatgct gattgaaaaa ctgaactatc tggttttaa agacaacgaa  7380
tttgacaaaa cgggtggcgt actccgtgcc tatcagctga ccgctccgtt cgaaacgttc  7440
aagaaaatgg gtaaacaaac ggggattatc tattatgtgc cagctggttt cacctccaag  7500
atttgtccag ttacgggctt cgttaaccag ctgtacccga aatacgagag cgttagcaaa  7560
tctcaagaat ttttcagcaa attcgacaag atctgctata atctggataa aggctatttc  7620
gagttcagct tcgattacaa aaacttcggc gataaagcgg ctaaaggtaa gtggactatt  7680
gctagctttg gtagccgtct gattaacttt cgcaactccg acaaaaacca taattgggac  7740
acgcgtgaag tgtatccgac caaagaactg gaaaaattac tgaaagacta ttccatcgaa  7800
tatggtcatg gggagtgcat taaagcggcg atttgcggtg aatccgataa gaaattttc  7860
gccaaactga ccagcgtgct taacaccatt ctgcaaatgc gtaattcaa aacgggtacg  7920
gagctggact acctgatttc tccggtagcc gacgttaacg gcaacttctt cgattctcgt  7980
caagcaccga aaatatgcc acaagacgcg gatgccaacg gtgcatacca tatcggctta  8040
aaaggcttaa tgttattagg ccgtatcaag aataatcagg agggcaagaa attaaatctg  8100
gttatcaaaa acgaagaata cttcgagttc gttcagaatc gtaacaatta atgtatgctt  8160
aagcagctcg gtaccaaaga cgaacaataa gacgctgaaa agcgtctttt ttcgttttgg  8220
tcctgttgcg gcgcgatagt gtgaacatgc tatagacttc tggtgctacc cgactgacaa  8280
ttaatcatcc ggctcgtata atgctagcaa tttctactgt tgtagatcat tccggaacgt  8340
tccagcgctg caatttctac tgttgtagat ctgatttttc acatgttacc tttcaatttc  8400
tactgttgta gatccgaaaa cgtaaagctt cagctgtaat ttctactgtt gtagatatca  8460
tatctggcgt taatggagtt tcgagacgaa caataaggcc tccctaacgg ggggcctttt  8520
ttattgataa caaaagtaac ttcgagcttg tctacctcct agcaccatta ttgcaattaa  8580
taaacaacta acgacaatt ctacctaaca gttttcatat atgacgagca gttaagtgat  8640
gagtaaaggt gaggaattat ttactggtgt tgttccgatc ttagttgaac tggacggcga  8700
tgttaacggt cataaaattca gtgttcgtgg tgaaggtgaa ggtgatgcaa ccaacggtaa  8760
gctgaccctg aaattcatct gcactactgg aaaattacca gtaccgtgcc ctactctgg  8820
gactaccctg acctatggtg ttcagtgttt ttctcgttac cctgaccaca tgaagcaaca  8880
tgatttcttc aaatctgcaa tgccggaagg ttatgtacag agcgcacca tttctttcaa  8940
agacgatggc acgtataaaa cccgtgcaga ggttaaattt gaaggtgaca ctctggtgaa  9000
tcgtattgaa ctgaaaggca ttgatttcaa agaggacggc aatatttag gccacaaact  9060
ggaatataac ttcaactccc ataacgttta catcaccgca gacaacaga agaacgttat  9120
caaagctaac ttcaaaattc gccataacgt tgaagatggt agcgtacagc tggcggatca  9180
ttaccaacag aacactccga ttggagatgc tcctgttttta ctgccggata accactacct  9240
gtccacccag tctaaactgt cgaaggatcc gaacgaaaag cgcgaccaca tggtgttatt  9300
agagttcgtt accgctagtg gtatcacgca cggtatggat gaactctaca aataagacga  9360
acaataaggg agcgggaaa ccgctccct tttttattga taacaaaagt aaattgcacg  9420
ctgatagtct cccaattgcg aaggaccaaa acgaaaaaac acccttcgg gtgtctttttc  9480
tggaatttgg taccgagtac taggtatcgt gtaagtagcg aaggcccgta cgcgagataa  9540
actgctaggc aaccgcgact ctacgactgg tgctcgattt aatttcgctg acgtaaagaa  9600
attatcggca gtgcgtcaac tgccgtatct ttatcttaat taggtagttg acaagccct  9660
tgaaagaaat agcaagagcc tgcctctcta ttgaagtcac ggcgaaagtc gggtagaaat  9720
```

-continued

```
caaagaaagc agaaattaaa tcggagtaac actaaggtgg gataactccg taactgacta  9780
cgcctttctc tagactttac ttgaccagat acactgtctt tgacacgttg aaggattaga  9840
gcaatcaaat ccaagactgg ctaagcacga agcaactctt gagtgttaaa aagttatctc  9900
ctgtattcgg gaagcgggta ctagaagatt gcagggactc cgacgttaag taaattacaa  9960
agtaataagt atcgttcagg atcacgttac cgcaataaga agcgagaata atataatttc  10020
cgaagtgctt accccagtag tgactattcc tataacccct ctgagtgtcc ggaggcggaa  10080
atttgccacg aaagagaaag tatttccccg acaataataa aggggcgctc ctcagctttt  10140
ccacttggtt gggtaagcta ggcaactctg aaaggagttt cggcgaattg aagccgacag  10200
ctttgaattg ttttaggggc gttattcgag ggcaatcgga gctaacttca agactacttc  10260
tttgttgaat actaaatagt gcaaaggtcg tgtttcctca aggatactcc gctaacaata  10320
taggattcca atcagattca gcactggcgg tacgggtgtt gcggtgaggc gttcgggttt  10380
acggctcgaa gctagcacgg taggaagcct gacaatcacc aagcaaaagg gccgtcgaag  10440
gcccacaaga tacgaaagct ctcgaagcct tatccttgac cgatccacct atttaggcag  10500
ttacgcacaa aagctaccca ataatccgtg acaggcacaa tatcacggaa caaaaccgaa  10560
aactctcgta cacggttagg ttttcgctag gaagaataaa cctctatctt gattataaga  10620
aggctcccca agcaccccca aaaccgaaat agcggtttgc aataagggac aagttacgag  10680
tgtagacacg cagaattatc cagcctttag tctttaggaa ggcaaagcta ttgtacgcgg  10740
tagccgtcgt agcaatttac caactgtaga attattggac acacgtagga agggcttaca  10800
gttgaagttt aataaggtca cacgcaaaac cgctaaggaa taatcgcacc gttagcgaaa  10860
gaatatttca gagcggttag taaaggttga gtaaagtgag attccaaagt gagcctttat  10920
aaaaagtaaa gagctataat aaaaccgtcg agcagaaaac aatcgcctga aatctcaagc  10980
acgttgccct ttctaacgtc gctaaggttt cgtaaaccg tttgattagg aagaagaata  11040
agtaacccga ttaggtttga gatcgcgggt tatcggtttg gattaaaagt ggataccagc  11100
ggagtcaacg ccgacgcaaa cgtacagtga tccaatcctg ttgcacggtc aagcacaatc  11160
agctcgcaag atcttggaat agtgtgccca acagtttagt tgagggccac gttccgacta  11220
caagttgctt caagagggga attttggattt ggcaatggcc ccccgttttct acctcaagag  11280
gcgacgagta ttaaccgcgc cagctgtcgg cacaagggcc aaagaagatt ccaatttctt  11340
attcccgaat aacctccgaa tccctgcggg aaaatcaccg accgaatagc ctagaagcaa  11400
gggggaacag ataggtataa ttagcttaag agagtaccag ccgtgacaac agcgtagtaa  11460
ccacaaactt acgctgggc ttcttttggcg gatttttaca gatactaaca aggtgatttg  11520
aagtacctta gttgaggatt taaacgcgct atccggtaat ctccaaattg ggaaataccg  11580
ttcaaagagg gctagaatta cttaaaagcc ttcacccgc ctgcgctata cgcgcccact  11640
ctcccgttta tccgtccaag cggaagcagg gcgatcctcc gctaagatat tcttacgtgt  11700
aacgtagcta agtatcccaa atagctggcg tacgcgttga acaccgccta gaggatcgtg  11760
actcgccgga cgagcgtgtt attggggact tacgccagcg tagactacaa cgcgcccaga  11820
ttaaccctgc acgtattgcc ttgaataacg tactaatctc tccggctctc gacaatctat  11880
cgagcgactc gattatcaac gggtgtcttg cagtt                              11915

SEQ ID NO: 30       moltype = DNA  length = 861
FEATURE             Location/Qualifiers
source              1..861
                    mol_type = other DNA
                    note = beta-lactamase gene
                    organism = synthetic construct
SEQUENCE: 30
atgagtattc aacatttccg tgtcgccctt attccctttt tgcggcatt ttgccttcct    60
gtttttgctc acccagaaac gctggtgaaa gtaaaagacg ctgaggatca gttgggagcc  120
cgtgtgggtt acatcgagct ggatctcaac agcggtaaga tccttgagag ttttcgcccc  180
gaagaacgtt ttccaatgat gagcactttt aaagttctgc tatgtggcgc ggtattatcc  240
cgtgttgatg ccggacaaga gcaacttggt cgccgtatac actattctca gaatgacttg  300
gttgagtact caccagttac cgaaaagcat cttacggatg gcatgacagt aagagaatta  360
tgcagtgctg ccataaccat gagtgataac acggcagcca acttactctt gacaacgatc  420
ggagggccga aggagctaac cgcttttttg cacaacatgg gggatcatgt aactcgcctt  480
gatcgttggg agccggagct gaatgaagcc ataccaaacg acgagcgtga caccacgatg  540
cccgcagcaa tggcaacaac gttgcgcaaa ctattaactg gcgaactact tactctagct  600
tctcgtcaac aattaataga ctggatggag gcggataaag ttgcaggcc acttctgcgt  660
tcggccttc cggctggctg gtttattgct gataaatctg gagcaggcga gcgtggatct  720
gcggtatca ttgcagcact ggggccagat ggtaagccct cccgtatcgt agttatctac  780
acgacgggga gtcaggcaac tatggatgaa cgaaatagac agatcgctga gataggtgca  840
tcactgatta gcattggta a                                             861
```

MICROBIOME MODULATION OF A HOST BY DELIVERY OF DNA PAYLOADS WITH MINIMIZED SPREAD

CROSS REFERENCE TO RELATED APPLICATIONS

This application is a divisional of U.S. application Ser. No. 17/565,060 filed on Dec. 29, 2021, which is a continuation-in-part of U.S. application Ser. No. 17/138,084 filed Dec. 30, 2020, and claims the benefit of U.S. application 63/132,090 filed Dec. 30, 2020, U.S. application 63/132,190 filed Dec. 30, 2020, U.S. application 63/137,989 filed Jan. 15, 2021, and is a continuation-in-part of PCT/EP2020/088043 filed Dec. 30, 2020, which claims the benefit of 62/995,278 filed on Dec. 30, 2019 all of which are herein incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Jul. 7, 2023, is named EB2020-06_USDiv.xml and is 120,547 bytes in size.

TECHNICAL FIELD

The present invention relates to nucleic acids of interest for modulating the microbiome of a host, to vectors encoding said nucleic acids and to methods for modulating the microbiome of a host by delivering said nucleic acids of interest.

BACKGROUND

Delivery of DNA payloads to express genes of interest in bacterial populations outside of the lab has a lot of applications among which medicine, agriculture, biofueling, cosmetics.

The strategy relies on the delivery of DNA to target bacterial cells in a pure or mixed bacterial population by a viral capsid, by bacterial conjugation or by other methods so that one or several genes of interest will be expressed at a sufficient level to produce a desired effect. The effect can be a direct therapeutic effect on the bacteria itself in or on the host, by killing the bacteria and therefore reducing its colonization level or modifying its ratio compared to other bacteria in the population if multiple species or multiple strains are present; by modifying its genome, by modifying its metabolism or its composition (protein, lipids, sugars, metabolites, RNA, etc.). The effect can also be an indirect effect by leveraging the target bacteria to produce, display or secrete one or multiple molecule(s) such as prophylactic or therapeutic molecule(s) that will have a direct or indirect effect on the host or on other members of the host microbiome.

One of the major concerns with such a strategy is that the exogenous DNA is transferred to progeny cells if the exogenous DNA is stably maintained in the cells in which it is delivered to, or is transferred to other bacteria via other gene transfer mechanism and then stably maintained in these other populations. More generally, the containment of the exogenous DNA payload once delivered in the bacterial populations is a concern.

To solve this issue, the present inventors have herein developed a new strategy that ensures that DNA payloads once delivered in target bacteria cannot replicate in the target bacteria but still express the gene(s) of interest at a level that is enough to exert the expected outcome on the bacteria or on the host, without the need of an antibiotic resistance selection marker on the DNA payload, and without the need of a selection step with an antibiotic.

Plasmids carrying conditional origins of replication have a long history of use by microbiologists as a tool to genetically modify bacterial strains of interest, therefore creating stable genetically modified organisms. They are typically used to select for recombination events between a plasmid carrying such origins and the genome of a bacteria of interest.

Such plasmids carry an antibiotic resistance selection marker and can be introduced into the bacteria by transformation, conjugation or any other method. Because they lack an autonomously replicating origin of replication, only the bacteria that have recombined the plasmid into their genome will stably maintain the selection marker and survive a selection step. The plasmid being stably integrated and maintained in progeny cells, the progeny cells will also be able to survive in presence of the selection marker.

The most commonly used conditional origin of replication is based on the wild-type plasmid R6K and derivatives which belong to the IncX group of replicon, a group commonly found in a variety of bacterial isolates. The replication of these plasmids is dependent on binding of the pir encoded Π initiator protein to the origin of replication. This protein can be expressed from a different replicon (in trans) than the plasmid carrying the R6K origin of replication. In this situation the replication of the R6K on plasmid is conditional on the expression of the pir gene in trans. When delivered to a bacteria of interest, the plasmid will not replicate unless the pir gene is present and expressed.

Similar conditional origins have also been built based on other systems including ColE1 origins (Panayotatos (1984) *Nucleic Acids Res.* 12:2641-2648) or IncPalpha oriV (Matsumoto-Mashimo et al. (2004) *Res. Microbiol.* 155:455-461). There are several drawbacks associated with these systems if one would try to build a system with minimal risk of genetically modified material spread in an in vivo setting (human, environment or animal for instance). Notably, such systems are inspired from origins that are almost ubiquitous in nature, such as ColE1 and R6K-type for instance that can be found in many Enterobacteria. Having such an origin on a recombinant plasmid delivered into a microbiome therefore significantly increases the chances not only of recombination with between the recombinant plasmid and wild-type elements within the microbiome, but also of having such plasmid being replicated within this microbiome since the wild-type elements would bring the missing factor necessary for the replication of the plasmid. Additionally, since inducible systems are usually leaky, conditional origins of replication relying on such system have a high chance of being replicated at a basal level—enough to spread in the population—or even at a full replication level if the inducer is present in the target population (for instance, LacI-based origins will be active if lactose is present, which is very often the case in vivo, given modern age diet).

The aim of the present invention is specifically to engineer and efficiently produce vehicles containing a DNA payload that can be transferred to a target bacterial population, not with the purpose of making and selecting recombination events between the DNA payload and the target bacterial genome to create stably genetically modified bacteria that can transfer the modification to progeny cells, but on the opposite with the purpose of limiting and/or preventing the creation of genetically modified progeny cells while still enabling a direct or indirect effect on the bacteria it is delivered into or its host via the efficient expression of genes of interest carried on the DNA payload.

Desired effects to be obtained in targeted bacteria or the host include therapeutic effect, cosmetic effect, bioremediation effect, effects on plant growth or physiology, effects on animal growth or physiology as non limiting examples.

Achieving therapeutic or other type of effect on a target bacteria or its environment with a non-replicative vector is not an obvious development for the simple reason that it can only be achieved if the DNA payload is efficiently delivered to the target bacteria and if it can be expressed to a high enough level and for a sufficient amount of time despite its non-replicative nature. While a replicative plasmid will produce copies of itself, increasing gene dosage, and will be passed down to daughter cells enabling a significant maintenance time in the bacterial population, none of these effects occur with a non-replicative plasmid.

The present inventors here demonstrate, for the first time, that it is possible to obtain an effect in vivo, such as a therapeutic effect, with the delivery of a non-replicative vector to a bacteria.

To this purpose, the present inventors developed a novel conditional origin of replication particularly efficient for this application, that is based on a rarely occurring two-system components to limit recombination events in the target population, the primase and origin of replication of phage-like inducible elements, namely phage-inducible chromosomal islands (PICIs), and they demonstrate for the first time that such type of conditional origin, even with the primase in trans, enables the efficient packaging of the DNA payload into the delivery vehicle, here a phage-derived particle or packaged phagemid.

PICIs, disclosed in Fillol-Salom et al. (2018) *The ISME Journal* 12:2114-2128 or in Fillol-Salom et al. (2019) *Mol. Cell* 75:1020-1030 are systems similar to P4-like elements that hijack Myoviridae, with the main difference that, according to current research, they do not modify the size of the capsid to accommodate their genomes. Since lambdoid PICIs are usually 10-13 kb long and the phages they hijack possess genomes close to 50 kb, this means that they are able to insert several copies of their small genome into a large capsid.

According to research, PICIs are able to completely abolish phage production and only lead to the packaging of their genomes. PICIs sense when the lambdoid phage to be hijacked is being induced, they excise from the genome where they reside as prophage-like islands and they replicate their genomes. Replication is based on a single protein, the primase, containing primase and helicase activity, and a short DNA fragment, usually right after the primase gene, that is recognized as an origin of replication by the primase. Additionally, many different PICIs have been described, each one containing different primase-ori pairs.

Fillol-Salom et al. (2018) *The ISME Journal* 12:2114-2128 specifically discloses PICIs originating in *E. coli* strain CFT073. In this document, the authors show that the genetic module containing the primase and the ori can function as an independent replication module when inserted in cis in thermosensitive-origin-containing plasmids: at the permissive temperature, the plasmid replicates through the plasmid origin, but when shifted to the non-permissive temperature, the primase and ori module acts as the main source of replication of the plasmid. However, from this observation it is not clear for the skilled person if, even at the non-permissive temperature, replication may have been due to the thermosensitive origin at some degree as it can happen; if the primase and ori can be physically separated (i.e., putting them apart from each other on the same plasmid or having a system in trans) and still enables the replication of the plasmid; and finally, if the ori, that is located right downstream of the primase, is the only element needed for replication or if there is a second element needed and if a specific orientation of the different elements is important, such as in P4, where two elements, the ori and the crr sequence, moreover in a specific orientation, are needed for replication (Flensberg et al. (1987) *J. Mol. Biol.* 195:439-445).

While other primase-based systems have been developed in which the primase protein is expressed in trans (Ziegelin et al. (2005) *J. Bacteriol.* 187:3445-3454), it is not known if this type of replication is compatible with phagemid packaging, and even in the case it could be, it would be even less obvious to predict that the packaging would be efficient.

It is indeed also very important that the DNA payload and its vehicle are produced very efficiently in order to be economically viable, which is not an obvious development either. Indeed, some studies have shown that the production titers of phage-derived particles packaging a DNA payload containing a conditional on were reduced by at least 3 logs compared to a DNA payload containing a non-conditional ori, and despite multiple engineering trials, this titer could not get increased.

SUMMARY OF THE INVENTION

The present invention arises from the unexpected finding that not only a DNA payload devoid of antibiotic resistance marker and autonomously replicative origin of replication can be packaged at high-titer in phage-derived particles but also that these DNA payloads can be efficiently delivered to the target bacteria and that these DNA payloads, while non replicative, can exert the intended effect. In particular, the present inventors also demonstrated for the first time that a non replicative DNA payload expressing a nuclease or an engineered nuclease, such as a base-editor, can result in similar killing or base-editing efficiency as its replicative counterpart.

The present invention thus concerns a method for in vivo modulating the microbiome of a host organism by delivering a nucleic acid of interest into a targeted receiver bacterial cell of said microbiome, said nucleic acid of interest producing a given effect on said targeted receiver bacterial cell,
 wherein said method comprises administering, in said host organism, a nucleic acid vector comprising said nucleic acid of interest,
  wherein said vector further comprises a conditional origin of replication which is inactive in the targeted receiver bacterial cell but is active in a donor bacterial cell, and said vector is devoid of antibiotic resistance marker,
 thereby delivering said nucleic acid of interest into the targeted receiver bacterial cell, and
 wherein, once delivered into said targeted receiver bacterial cell, said nucleic acid of interest produces said given effect on said targeted receiver bacterial cell while said vector is not replicated in said targeted receiver bacterial cell.

The present invention also concerns a method for in vivo modulating the microbiome of a host organism by delivering a nucleic acid of interest into a targeted receiver bacterial cell of said microbiome, said nucleic acid of interest being expressed in said targeted receiver bacterial cell, thereby producing a given effect on said targeted receiver bacterial cell, wherein said method comprises administering, in said host organism, a nucleic acid vector comprising said nucleic acid of interest, wherein said vector further comprises a conditional origin of replication which is inactive in the targeted receiver bacterial cell but is active in a donor bacterial cell, and said vector is devoid of antibiotic resistance marker, thereby delivering said nucleic acid of interest into the targeted receiver bacterial cell, and wherein, once delivered into said targeted receiver bacterial cell, said nucleic acid of interest produces said given effect on said targeted receiver bacterial cell while said vector is not replicated in said targeted receiver bacterial cell.

In a particular embodiment, said given effect on said targeted receiver bacterial cell generates, directly or indirectly, a reaction in said organism hosting said targeted receiver bacterial cell.

DETAILED DESCRIPTION

Definitions

As used herein, the term "nucleic acid" refers to a sequence of at least two nucleotides covalently linked together which can be single-stranded or double-stranded or contains portions of both single-stranded and double-stranded sequences. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphosphoroamidite linkage and/or deoxyribonucleotides and ribonucleotides nucleic acids. Any combination of the above features of a nucleic acid is also encompassed by the present invention.

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

Method of In Vivo Modulation

The present invention relates to methods for in vivo modulating the microbiome of a host organism.

By "microbiome" is meant herein the aggregate of all microbiota that reside on or within an organism tissues and biofluids along with the corresponding anatomical sites in which they reside, including, for mammalian organisms, the skin, mammary glands, placenta, seminal fluid, vagina, uterus, ovarian follicles, lung, saliva, oral mucosa, conjunctiva, biliary tract, and gastrointestinal tract, blood, tumors, brain. In a particular embodiment, the microbiome more specifically refers to the bacteria populations forming said microbiota.

By "modulating the microbiome" is meant herein exerting a modifying or controlling influence on the microbiome. In the context of the invention, modulating the microbiome encompasses modulating the microbiome function and/or modulating the microbiome composition.

By "modulating the microbiome composition" is meant herein changing the composition of said microbiome, including removing specific species or strains of said microbiome, changing the proportion between different species or strains of said microbiome or replacing specific species or strains of said microbiome by other species or strains. Said modulation of the microbiome composition can be achieved directly or indirectly, typically by modifying said targeted bacterial cell, which can then have an effect, such as a killing effect, on other bacteria of the microbiome, which were not initially targeted by said vector.

By "modulating the microbiome function" is meant herein changing the function of specific species or strains of said microbiome, for example by making specific species or strains express particular molecules, or by making specific species or strains stop expressing particular molecules.

By "host organism" is meant herein any multicellular organism, including any animal or any plant. In a particular embodiment, said host organism is a host subject.

By "host subject" is meant herein any animal (e.g., a primate, e.g., a human) hosting said microbiome. The subject according to the invention is preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

In the method of the present invention, a nucleic acid of interest is delivered into a targeted receiver bacterial cell of said microbiome or a group of targeted receiver bacterial cells of said microbiome, said nucleic acid of interest being comprised in a vector provided by a donor bacterial cell.

By "donor bacterial cell" is meant herein a bacterium that is capable of hosting a vector comprising a nucleic acid of interest, of producing a vector comprising said nucleic acid of interest and/or which is capable of transferring said vector comprising said nucleic acid to another bacterium. In a particular embodiment, said vector may be a phagemid, and said donor bacterial cell may then be a bacterial cell able to produce said phagemid, more particularly in the form of a packaged phagemid. In an alternative embodiment, said vector may be a plasmid, more particularly a conjugative plasmid, and said donor bacterial cell may then be a bacterium that is capable of transferring said conjugative plasmid to another bacterium, in particular by conjugation.

By "receiver bacterial cell" is meant herein any bacterium from the host microbiome which is specifically targeted to be delivered with said nucleic acid of interest.

The targeted receiver bacteria can be any bacteria, in particular present in an organism, more particularly in a mammal organism. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted receiver bacterial cells may depend on the type of bacteriophages being used for preparing the vector and/or bacterial delivery vehicles. For example, some bacteriophages exhibit tropism for, or preferentially target, specific host species of bacteria. Other bacteriophages do not exhibit such tropism and may be used to target a number of different genus and/or species of endogenous bacterial cells.

Examples of receiver bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Propionibacterium* spp., *Cutibacterium* spp., *Micrococcus* spp., *Bartonella* spp., *Borrelia* spp., *Brucelia* spp., *Campylobacter* spp., *Chlamydophilia* spp., *Cutibacterium* (formerly *Propionibacterium*) spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., and *Lactobacillus* spp, and a mixture thereof.

Thus, the targeted receiver bacterial cell may be any one or more of the foregoing genus of bacteria.

In an embodiment, the targeted receiver bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Propionibacterium* spp., *Cutibacterium* spp. and *Listeria* spp.

In some embodiments, targeted receiver bacterial cells of the present disclosure are anaerobic bacterial cells (e.g., cells that do not require oxygen for growth). Anaerobic bacterial cells include facultative anaerobic cells such as but not limited to *Escherichia coli*, *Shewanella oneidensis* and *Listeria*. Anaerobic bacterial cells also include obligate anaerobic cells such as, for example, *Bacteroides* and *Clostridium* species. In humans, anaerobic bacteria are most commonly found in the gastrointestinal tract. In some particular embodiments, the targeted receiver bacteria are thus bacteria most commonly found in the gastrointestinal tract.

In some embodiments, the targeted receiver bacterial cells are, without limitation, *Bacteroides thetaiotaomicron*, *Bacteroides fragilis*, *Bacteroides distasonis*, *Bacteroides vulgatus*, *Clostridium leptum*, *Clostridium coccoides*, *Staphylococcus aureus*, *Bacillus subtilis*, *Clostridium butyricum*, *Brevibacterium lactofermentum*, *Streptococcus agalactiae*, *Lactococcus lactis*, *Leuconostoc lactis*, *Actinobacillus actinomycetemcomitans*, cyanobacteria, *Escherichia coli*, *Helicobacter pylori*, *Selenomonas ruminatium*, *Shigella sonnei*, *Zymomonas mobilis*, *Mycoplasma mycoides*, *Treponema denticola*, *Bacillus thuringiensis*, *Staphylococcus lugdunensis*, *Leuconostoc oenos*, *Corynebacterium xerosis*, *Lactobacillus plantarum*, *Lactobacillus rhamnosus*, *Lactobacillus casei*, *Lactobacillus acidophilus*, *Enterococcus faecalis*, *Bacillus coagulans*, *Bacillus cereus*, *Bacillus popillae*, *Synechocystis* strain PCC6803, *Bacillus liquefaciens*, *Pyrococcus abyssi*, *Selenomonas ruminantium*, *Lactobacillus hilgardii*, *Streptococcus ferus*, *Lactobacillus pentosus*, *Bacteroides fragilis*, *Staphylococcus epidermidis*, *Streptomyces phaechromogenes*, *Streptomyces ghanaenis*, *Klebsiella pneumoniae*, *Enterobacter cloacae*, *Enterobacter aerogenes*, *Serratia marcescens*, *Morganella morganii*, *Citrobacter freundii*, *Pseudomonas aeruginosa*, *Parvimonas micra*, *Prevotella intermedia*, *Fusobacterium nucleatum*, *Prevotella nigrescens*, *Actinomyces israelii*, *Porphyromonas endodontalis*, *Porphyromonas gingivalis Micrococcus luteus*, *Bacillus megaterium*, *Aeromonas hydrophila*, *Aeromonas caviae*, *Bacillus anthracis*, *Bartonella henselae*, *Bartonella Quintana*, *Bordetella pertussis*, *Borrelia burgdorferi*, *Borrelia garinii*, *Borrelia afzelii*, *Borrelia recurrentis*, *Brucella abortus*, *Brucella canis*, *Brucella melitensis*, *Brucella suis*, *Campylobacter jejuni*, *Campylobacter coli*, *Campylobacter fetus*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtheria*, *Cutibacterium acnes* (formerly *Propionibacterium acnes*), *Ehrlichia canis*, *Ehrlichia chaffeensis*, *Enterococcus faecium*, *Francisella tularensis*, *Haemophilus influenza*, *Legionella pneumophila*, *Leptospira interrogans*, *Leptospira santarosai*, *Leptospira weilii*, *Leptospira noguchii*, *Listeria monocytogenes*, *Mycobacterium leprae*, *Mycobacterium tuberculosis*, *Mycobacterium ulcerans*, *Mycoplasma pneumonia*, *Neisseria gonorrhoeae*, *Neisseria meningitides*, *Nocardia asteroids*, *Rickettsia rickettsia*, *Salmonella enteritidis*, *Salmonella typhi*, *Salmonella paratyphi*, *Salmonella typhimurium*, *Shigella flexneri*, *Shigella dysenteriae*, *Staphylococcus saprophyticus*, *Streptococcus pneumoniae*, *Streptococcus pyogenes*, *Streptococcus viridans*, *Treponema pallidum*, *Ureaplasma urealyticum*, *Vibrio cholera*, *Vibrio parahaemolyticus*, *Yersinia pestis*, *Yersinia enterocolitica*, *Yersinia pseudotuberculosis*, *Actinobacter baumanii*, *Pseudomonas aeruginosa*, and a mixture thereof. In an embodiment the targeted bacteria of interest are selected from the group consisting of *Escherichia coli*, *Enterococcus faecium*, *Staphylococcus aureus*, *Klebsiella pneumoniae*, *Acinetobacter baumanii*, *Pseudomonas aeruginosa*, *Enterobacter cloacae*, and *Enterobacter aerogenes*, and a mixture thereof.

In some embodiments, the targeted bacterial cells are, without limitation, *Anaerotruncus*, *Acetanaerobacterium*, *Acetitomaculum*, *Acetivibrio*, *Anaerococcus*, *Anaerofilum*, *Anaerosinus*, *Anaerostipes*, *Anaerovorax*, *Butyrivibrio*, *Clostridium*, *Capracoccus*, *Dehalobacter*, *Dialister*, *Dorea*, *Enterococcus*, *Ethanoligenens*, *Faecalibacterium*, *Fusobacterium*, *Gracilibacter*, *Guggenheimella*, *Hespellia*, *Lachnobacterium*, *Lachnospira*, *Lactobacillus*, *Leuconostoc*, *Megamonas*, *Moryella*, *Mitsuokella*, *Oribacterium*, *Oxobacter*, *Papillibacter*, *Proprionispira*, *Pseudobutyrivibrio*, *Pseudoramibacter*, *Roseburia*, *Ruminococcus*, *Sarcina*, *Seinonella*, *Shuttleworthia*, *Sporobacter*, *Sporobacterium*, *Streptococcus*, *Subdoligranulum*, *Syntrophococcus*, *Thermobacillus*, *Turibacter*, *Weisella*, *Clostridium*, *Bacteroides*, *Ruminococcus*, *Faecalibacterium*, *Treponema*, *Phascolarc-* tobacterium, Megasphaera, Faecalibacterium, Bifidobacterium, Lactobacillus, Sutterella, and/or Prevotella.

In other embodiments, the targeted bacteria cells are, without limitation, Achromobacter xylosoxidans, Acidaminococcus fermentans, Acidaminococcus intestini, Acidaminococcus sp., Acinetobacter baumannii, Acinetobacter junii, Acinetobacter lwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes finegoldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogeniformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus licheniformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides sp., Bacteroides stercoris, Bacteroides thetaiotaomicron, Bacteroides uniformis, Bacteroides vulgatus, Bacteroides xylanisolvens, Bacteroides pectinophilus ATCC, Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii, Blautia hydrogenotrophica, Blautia luti, Blautia obeum, Blautia producta, Blautia wexlerae, Brachymonas chironomi, Brevibacterium senegalense, Bryantella formatexigens, butyrate-producing bacterium, Butyricicoccus pullicaecorum, Butyricimonas virosa, Butyrivibrio crossotus, Butyrivibrio fibrisolvens, Caldicoprobacter faecalis, Campylobacter concisus, Campylobacter jejuni, Campylobacter upsaliensis, Catenibacterium mitsuokai, Cedecea davisae, Cellulomonas massiliensis, Cetobacterium somerae, Citrobacter braakii, Citrobacter freundii, Citrobacter pasteurii, Citrobacter sp., Citrobacter youngae, Cloacibacillus evryensis, Clostridiales bacterium, Clostridioides difficile, Clostridium asparagiforme, Clostridium bartlettii, Clostridium boliviensis, Clostridium bolteae, Clostridium hathewayi, Clostridium hiranonis, Clostridium hylemonae, Clostridium leptum, Clostridium methylpentosum, Clostridium nexile, Clostridium orbiscindens, Clostridium ramosum, Clostridium scindens, Clostridium sp, Clostridium sp., Clostridium spiroforme, Clostridium sporogenes, Clostridium symbiosum, Collinsella aerofaciens, Collinsella intestinalis, Collinsella stercoris, Collinsella tanakaei, Coprobacillus cateniformis, Coprobacter fastidiosus, Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella tarda, Eggerthella lenta, Eisenbergiella tayi, Enorma massiliensis, Enterobacter aerogenes, Enterobacter asburiae, Enterobacter cancerogenus, Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus sp., Enterovibrio nigricans, Erysipelatoclostridium ramosum, Escherichia coli, Escherichia sp., Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium cf, Faecalibacterium prausnitzii, Faecalitalea cylindroides, Ferrimonas balearica, Finegoldia magna, Flavobacterium daejeonense, Flavonifractor plautii, Fusicatenibacter saccharivorans, Fusobacterium gonidiaformans, Fusobacterium mortiferum, Fusobacterium necrophorum, Fusobacterium nucleatum, Fusobacterium periodonticum, Fusobacterium sp., Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis, Herbaspirillum massiliense, Holdemanella biformis, Holdemania fdiformis, Holdemania filiformis, Holdemania massiliensis, Holdemania filiformis, Hungatella hathewayi, Intestinibacter bartlettii, Intestinimonas butyriciproducens, Klebsiella oxytoca, Klebsiella pneumoniae, Kurthia massiliensis, Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis, Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillus plantarum subsp., Leuconostoc mesenteroides, Leuconostoc pseudomesenteroides, Listeria grayi, Listeria innocua, Mannheimia granulomatis, Marvinbryantia formatexigens, Megamonas funiformis, Megamonas hypermegale, Methanobrevibacter smithii, Methanobrevibacter smithii, Micrococcus luteus, Microvirgula aerodenitrificans, Mitsuokella jalaludinii, Mitsuokella multacida, Mollicutes bacterium, Murimonas intestini, Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides merdae, Paraprevotella xylaniphila, Parasutterella excrementihominis, Parvimonas micra, Pediococcus acidilactici, Peptoclostridium difficile, Peptoniphilus harei, Peptoniphilus obesi,

*Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oralis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteus penneri ATCC, Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina, Romboutsia lituseburensis, Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus sp, Ruminococcus sp., Ruminococcus torques, Sarcina ventriculi, Sellimonas intestinalis, Senegalimassilia anaerobia, Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oralis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus, Subdoligranulum variabile, Succinatimonas hippei, Sutterella parvirubra, Sutterella wadsworthensis, Terrisporobacter glycolicus, Terrisporobacter mayombei, Thalassobacillus devorans, Timonella senegalensis, Turicibacter sanguinis, unknown sp, unknown sp., Varibaculum cambriense, Veillonella atypica, Veillonella dispar, Veillonella parvula, Vibrio cincinnatiensis, Virgibacillus salexigens,* and *Weissella paramesenteroides.*

In other embodiments, the targeted bacteria cells are those commonly found on the skin microbiota and are without limitation *Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans* subsp. *xylosoxidans, Acidovorax konjaci, Acidovorax radicis, Acinetobacter johnsonii, Actinomadura citrea, Actinomadura coerulea, Actinomadura fibrosa, Actinomadura fulvescens, Actinomadura jiaoheensis, Actinomadura luteofluorescens, Actinomadura mexicana, Actinomadura nitritigenes, Actinomadura verrucosispora, Actinomadura yumaensis, Actinomyces odontolyticus, Actinomycetospora atypica, Actinomycetospora corticicola, Actinomycetospora rhizophila, Actinomycetospora rishiriensis, Aeromonas australiensis, Aeromonas bestiarum, Aeromonas bivalvium, Aeromonas encheleia, Aeromonas eucrenophila, Aeromonas hydrophila* subsp. *hydrophila, Aeromonas piscicola, Aeromonas popoffii, Aeromonas rivuli, Aeromonas salmonicida* subsp. *pectinolytica, Aeromonas salmonicida* subsp. *smithia, Amaricoccus kaplicensis, Amaricoccus veronensis, Aminobacter aganoensis, Aminobacter ciceronei, Aminobacter lissarensis, Aminobacter niigataensis, Ancylobacter polymorphus, Anoxybacillus flavithermus* subsp. *yunnanensis, Aquamicrobium aerolatum, Archangium gephyra, Archangium gephyra, Archangium minus, Archangium violaceum, Arthrobacter viscosus, Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium afermentans* subsp. *lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens, Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacterhalotolerans, Flavobacterium araucananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense* subsp. *putei, Herbaspirillum lusitanum, Herminiimonas fonticola, Hydrogenophaga intermedia, Hydrogenophaga pseudoflava, Klebsiella oxytoca, Kosakonia sacchari, Lactobacillus delbrueckii* subsp. *bulgaricus, Lactobacillus modestisalitolerans, Lactobacillus plantarum* subsp. *argentoratensis, Lactobacillus xiangfangensis, Lechevalieria roselyniae, Lentzea albida, Lentzea californiensis, Leuconostoc carnosum, Leuconostoc citreum, Leuconostoc gelidum* subsp. *gasicomitatum, Leuconostoc mesenteroides* subsp. *suionicum, Luteimonas aestuarii, Lysobacter antibioticus, Lysobacter koreensis, Lysobacter oryzae, Magnetospirillum moscoviense, Marinomonas alcarazii, Marinomonas primoryensis, Massilia aurea, Massilia jejuensis, Massilia kyonggiensis, Massilia timonae, Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydan, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogene, Micromonospora rhizosphaerae, Micromonospora saelicesensis, Microvirga subterranea, Microvirga zambiensis, Mycobacterium alvei, Mycobacterium avium* subsp. *silvaticum, Mycobacterium colombiense, Mycobacterium conceptionense, Mycobacterium conceptionense, Mycobacterium farcinogenes, Mycobacterium fortuitum* subsp. *fortuitum, Mycobacterium goo-* dii, Mycobacterium insubricum, Mycobacterium llatzerense, Mycobacterium neoaurum, Mycobacterium neworleansense, Mycobacterium obuense, Mycobacterium peregrinum, Mycobacterium saopaulense, Mycobacterium septicum, Mycobacterium setense, Mycobacterium smegmatis, Neisseria subflava, Nocardia lijiangensis, Nocardia thailandica, Novosphingobium barchaimii, Novosphingobium lindaniclasticum, Novosphingobium lindaniclasticum, Novosphingobium mathurense, Ochrobactrum pseudogrignonense, Oxalicibacterium solurbis, Paraburkholderia glathei, Paraburkholderia humi, Paraburkholderia phenazinium, Paraburkholderia phytofirmans, Paraburkholderia sordidicola, Paraburkholderia terricola, Paraburkholderia xenovorans, Paracoccus laeviglucosivorans, Patulibacter ginsengiterrae, Polymorphospora rubra, Porphyrobacter colymbi, Prevotella jejuni, Prevotella melaninogenica, Propionibacterium acnes subsp. elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis, Pseudonocardia alaniniphila, Pseudonocardia ammonioxydans, Pseudonocardia autotrophica, Pseudonocardia kongjuensis, Pseudonocardia yunnanensis, Pseudorhodoferax soli, Pseudoxanthomonas daejeonensis, Pseudoxanthomonas indica, Pseudoxanthomonas kaohsiungensis, Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis, Ramlibacter ginsenosidimutans, Rheinheimera japonica, Rheinheimera muenzenbergensis, Rheinheimera soli, Rheinheimera tangshanensis, Rheinheimera texasensis, Rheinheimera tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium vallis, Rhizobium vignae, Rhizobium vignae, Rhizobium yanglingense, Rhodococcus baikonurensis, Rhodococcus enclensis, Rhodoferax saidenbachensis, Rickettsia canadensis, Rickettsia heilongjiangensis, Rickettsia honei, Rickettsia raoultii, Roseateles aquatilis, Roseateles aquatilis, Salmonella enterica subsp. salamae, Serratia ficaria, Serratia myotis, Serratia vespertilionis, Shewanella aestuarii, Shewanella decolorationis, Sphingobium amiense, Sphingobium baderi, Sphingobium barthaii, Sphingobium chlorophenolicum, Sphingobium cupriresistens, Sphingobium czechense, Sphingobium fuliginis, Sphingobium indicum, Sphingobium indicum, Sphingobium japonicum, Sphingobium lactosutens, Sphingomonas dokdonensis, Sphingomonas pseudosanguinis, Sphingopyxis chilensis, Sphingopyxis fribergensis, Sphingopyxis granuli, Sphingopyxis indica, Sphingopyxis witflariensis, Staphylococcus agnetis, Staphylococcus aureus subsp. aureus, Staphylococcus epidermidis, Staphylococcus hominis subsp. novobiosepticus, Staphylococcus nepalensis, Staphylococcus saprophyticus subsp. bovis, Staphylococcus sciuri subsp. carnaticus, Streptomyces caeruleatus, Streptomyces canarius, Streptomyces capoamus, Streptomyces ciscaucasicus, Streptomyces griseorubiginosus, Streptomyces olivaceoviridis, Streptomyces panaciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces neuii subsp. anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibactersegnis, Agrococcus baldri, Albibactermethylovorans, Alcaligenes faecalis subsp. faecalis, Algoriphagus ratkowskyi, Alkalibacterium olivapovliticus, Alkalibacterium pelagium, Alkalibacterium pelagium, Alloprevotella rava, Alsobacter metallidurans, Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter venerupis, Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans subsp. lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus subsp. caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas sulfidaeris, Herpetosiphon aurantiacus, Hydrocarboniphaga effusa, Idiomarina maris, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oralis, Klebsiella oxytoca, Knoellia aerolata, Knoellia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevaniformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agariphilus, Nocardioides dilutus, Nocardioides ganghwensis, Nocardioides hwasunensis, Nocardioides nanhaiensis, Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacterterrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multiflagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimanifer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacter uvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes subsp. acnes, Propionibacterium acnes subsp. acnes, Propionibacterium acnes subsp. elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida, Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis, Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides, Staphylococcus auricularis, Staphylococcus epidermidis, Staphylococcus epidermidis, Staphylococcus hominis subsp. novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oralis, Streptococcus sanguinis, Streptomyces iconiensis, Streptomyces yanglinensis, Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter sanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus arseniciresistens, Yimella lutea, Zimmermannella alba, Zimmermannella bifida and Zoogloea caeni.

In other embodiments, the targeted bacteria cells are those commonly found in the vaginal microbiota and are, without limitation, Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyonggiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis, Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum subsp. infantis, Bifidobacterium longum, Bifidobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fungorum, Burkholderia phenoliruptix, Caldicellulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudogenitalium, Corynebacterium pyruviciproducens, Corynebacterium singulare, Corynebacterium striatum, Corynebacterium tuberculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister micraerophilus, Dialister pneumosintes, Dialister propionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotolerans, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odoribacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylli, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstonia pickettii, Ralstonia solanacearum, Raoultella planticola, Rhizobacter dauci, Rhizobium etli, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Ter-

*rahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae* and *Zoogloea ramigera*.

In one embodiment, the targeted receiver bacteria are *Escherichia coli*.

In one embodiment, the targeted receiver bacteria are *Klebsiella pneumoniae*.

In one embodiment, the targeted receiver bacteria are *Bacteroides thetaiotaomicron* and/or *Bacteroides faecis*.

In one embodiment, the targeted receiver bacteria are *Roseburia intestinalis*.

In one embodiment, the targeted bacteria are *Cutibacterium acnes* more specifically the acne related *Cutibacterium acnes* from the phylogroup IA1 or RT4, RT5, RT8, RT9, RT10 or Clonal Complex(CC) CC1, CC3, CC4, more specifically the ST1, ST3, ST4.

In one embodiment, the targeted receiver bacteria are pathogenic bacteria. The targeted receiver bacteria can be virulent bacteria.

In a particular embodiment, the targeted receiver bacteria are involved in infections in the host. In a particular embodiment, the targeted receiver bacteria are associated with the triggering, progression, or aggravation of auto-immune diseases in the host. In a particular embodiment, the targeted receiver bacteria are associated with the triggering, progression or aggravation of tumors or metastasis in the host. In a particular embodiment, the targeted receiver bacteria are associated with the triggering, progression or aggravation of neurodegenerative disease in the host. In a particular embodiment, the targeted receiver bacteria are associated with the triggering, progression or aggravation of CNS related disease in the host. In a particular embodiment, the targeted receiver bacteria are associated with the resistance of the host towards treatments against infection, tumor, neurodegenerative disease, CNS related disease, autoimmune disease, and/or cancer.

The targeted receiver bacteria can be antibacterial resistant bacteria, including those selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. The targeted receiver bacteria can be selected from the group consisting of extended-spectrum beta-lactamase-producing (ESBL) *Escherichia coli* strains. In a particular embodiment, said targeted receiver bacteria are ESBL *Escherichia coli* and/or ESBL *Klebsiella pneumoniae*.

Alternatively, the targeted receiver bacterium can be a bacterium of the microbiome of a given species, in particular a bacterium of the human microbiota.

Given Effect and Corresponding Nucleic Acids of Interest

In the modulating method of the invention, said nucleic acid of interest produces a given effect on said targeted receiver bacterial cell, as defined above.

By "nucleic acid producing a given effect on said targeted receiver bacterial cell" is meant herein that the delivery of said nucleic acid into said targeted receiver bacterial cell induces, directly or indirectly, a reaction into said targeted receiver bacterial cell (such as the expression of a RNA, the expression of a protein or the activation or the inhibition of an activity), wherein said reaction in said targeted receiver bacterial cell, preferably further generates, directly or indirectly, a reaction in said organism hosting said targeted receiver bacterial cell.

In a particular embodiment, the nucleic acid of interest is expressed in said targeted receiver bacterial cell, thereby producing said given effect. Expression of said nucleic acid of interest includes expression into a coding or non-coding RNA, or expression into a protein. Alternatively, in a particular embodiment, the nucleic acid of interest is not expressed in said targeted receiver bacterial cell, and the presence of said nucleic acid of interest in said targeted receiver bacterial cell produces said given effect (for example by providing binding regions to molecules already present in said targeted receiver bacterial cell).

In the context of the invention, said given effect may be selected from the group consisting of killing the receiver bacterial cell, making the receiver bacterial cell stop producing a given molecule, making the receiver bacterial cells reducing its level of production of a given molecule, and making the receiver bacterial cell produce a molecule of interest.

Making the Receiver Bacterial Cell Produce a Molecule of Interest

In a particular embodiment, said given effect is making the receiver bacterial cell produce a molecule of interest, in particular a host modulatory molecule.

In another particular embodiment, said given effect is making the receiver bacterial cell produce, as molecule of interest, transcription factors and/or modified nucleases, in particular to activate specific pathways or genes in the bacteria that are naturally turned off.

In another particular embodiment, said given effect is making the receiver bacterial cell produce a molecule of interest which increases or decreases, preferably temporarily, the fitness of said receiver bacterial cell to its environment, in particular compared to other members of the microbiome which are not receiver bacterial cells.

In another particular embodiment, said given effect is making the receiver bacterial cell produce, as molecule of interest, a molecule of interest which acts on the microbiome environment, in particular without generating an effect at the level of the host organism cells.

By "host modulatory molecule" or "HMM" is meant herein any molecule, produced by said receiver bacterial cell, that acts, directly or indirectly, at the level of the host organism.

Said HMM may be of any nature. In particular, said HMM may be selected from the group consisting of non-coding nucleic acids, coding nucleic acids, proteins, lipids, sugars, LPS, metabolites and small molecules.

Examples of non-coding nucleic acids typically include non-coding DNAs or non-coding RNAs, such as siRNAs.

Examples of coding nucleic acids typically include coding DNAs or coding RNAs.

Examples of proteins typically include cytokines, such as chemokines, interferons, interleukins, lymphokines, tumour necrosis factors and anti-inflammatory cytokines; surface layer proteins, such as SIpB, in particular from *Propionibacterium freudenreichii*; microbial anti-Inflammatory molecule (MAM), such as MAM from *Faecalibacterium praus-*

*nitz*; antibodies such as monoclonal antibodies, multispecific antibodies, chimeric antibodies, antibody fragments and derivatives thereof; nanobodies; enzymes, in particular enzymes leading to the production of other HMMs; peptides such as Immune Selective Anti-Inflammatory Derivatives (FEG, Salivary gland derived peptides), and mimic proteins or peptides derived from the microbiome that mimic antigens from cells of the subject.

Mimic peptides of particular interest are bacterial mimic peptides that are associated with auto-immune diseases, for example those mentioned in Negi et al. (2017) *Plos One* 12:e0180518, which are hereby incorporated by reference. Of particular interest are the gene sequences encoding any of the mimic peptides in S1 Table of Negi et al.

Examples of lipids typically include SCFAs, such as butyrate.

Examples of small molecules typically include cyclosporin, nonsteroidal anti-inflammatory drugs (NSAIDs), steroidal anti-inflammatory drugs (SAIDs) and ROS.

Said HMM may further have any effect. In a particular embodiment, said HMM may be a molecule that will affect the immune system of the host, the host CNS and/or the host metabolism.

In particular, said HMM may be selected from the group consisting of anticancer molecules, antibiotic molecules, anti-viral molecules, anti-parasite molecules, anti-protozoal molecules, anesthetic molecules, anticoagulant molecules, inhibitors of an enzyme, steroidal molecules, anti-inflammatory molecules, antihistamine molecules, immunosuppressant molecules, anti-neoplastic molecules, antigens, vaccines, antibodies, decongestant molecules, sedative molecules, analgesic molecules, antipyretic molecules, hormones, anti-hormone molecules, anticholinergic agents, antidepressant molecules, antipsychotic molecules, neurotoxin molecules, hypnotic molecules, tranquilizer molecules, anticonvulsant molecules, muscle relaxant molecules, anti-aging molecules, anti-neurodegeneration molecules, neuromodulators, antispasmodic molecules, muscle contractant molecules, channel blocker molecules, miotic molecules, anti-secretory molecules, anti-thrombotic molecules, diuretic molecules, cardiovascular active molecules, vasoactive molecules, vasodilating molecules, antihypertensive molecules, angiogenic molecules, modulators of cell-extracellular matrix interactions (e.g. cell growth inhibitors and anti-adhesion molecules), growth factors, differentiation factors, antioxidant molecules, inhibitors of DNA, RNA, or protein synthesis, apoptosis factors, anti-apoptosis molecules, or anti-UV molecules.

Said HMM may further be of any origin. In particular, said HMM may be selected from the group consisting of host endogenous molecules, host exogenous molecules expressed naturally by other organisms, and synthetic compounds.

By "host endogenous molecule" is meant herein any molecule naturally produced by the host subject, in particular by a healthy host subject.

By "host exogenous molecule expressed naturally by other organisms" is meant herein any molecule which is not produced by the host subject (or by a subject of the same species as the host species) but which is naturally produced by another organism, in particular an organism from another species, from another gender, from another family, from another class or from another kingdom. Typically, said host exogenous molecule expressed naturally by other organisms may be a molecule produced by bacteria, in particular by microbiota.

In a particular embodiment, the nucleic acid of interest encodes a bacteriocin or a lysin, which can be a proteinaceous toxin produced by receiver bacteria to kill or inhibit growth of other bacteria. Bacteriocins are categorized in several ways, including producing strain, common resistance mechanisms, and mechanism of killing. Such bacteriocin had been described from gram negative bacteria (e.g. microcins, colicin-like bacteriocins and tailocins) and from gram positive bacteria (e.g. Class I, Class II, Class III or Class IV bacteriocins).

In one embodiment, the nucleic acid of interest encodes a toxin selected in the group consisting of microcins, colicin-like bacteriocins, tailocins, Class I, Class II, Class III and Class IV bacteriocins.

In a particular embodiment, the corresponding immunity polypeptide (i.e. anti-toxin) may be used to protect receiver bacterial cells (see review by Cotter et al., Nature Reviews Microbiology 11: 95, 2013).

By "synthetic compound" is meant herein any molecule which is neither naturally produced by the host subject (or by a subject of the same species as the host species) nor by another organism, in particular an organism from another species, from another gender, from another family, from another class or from another kingdom.

Said molecule of interest may further be produced by said targeted receiver bacterial cell in any form. In particular, said HMM may be selected from the group consisting of secreted molecules, intracellular molecules and membrane-displayed molecules.

The production of said molecule of interest by said targeted receiver bacterial cell may require the delivery of a nucleic acid of interest which includes one or more type(s) of gene(s) or group(s) of genes. In particular, said nucleic acid of interest may be selected from the group consisting of a gene encoding said molecule of interest, in particular said HMM, several genes encoding a protein complex that is the molecule of interest, in particular the HMM, a gene or group of genes encoding enzyme(s) of a metabolic pathway leading to the production of the molecule of interest, in particular of the HMM, a coding nucleic acid which is the molecule of interest, in particular the HMM, and a non-coding nucleic acid which is the molecule of interest, in particular the HMM.

Making the Receiver Bacterial Cell Stop Producing a Given Molecule

In a particular embodiment, said given effect is making the receiver bacterial cell stop producing a given molecule.

By "making the receiver bacterial cell stop producing a given molecule" is meant herein reducing or abolishing the production of said given molecule by said bacterial cell and/or making the receiver bacterial cell produce a variant of said given molecule.

Typically, said given molecule the production of which is to be stopped has a negative effect on said host organism.

In a particular embodiment, said given molecule the production of which is to be stopped affects the fitness of said receiver bacterial cell to its environment. In a particular embodiment, making the receiver bacterial cell stop producing said given molecule, increases or decreases, preferably temporarily, the fitness of said receiver bacterial cell to its environment, in particular compared to other members of the microbiome which are not receiver bacterial cell.

In a particular embodiment, said given molecule may be selected from the group consisting of a toxin, a toxic factor, a virulence protein, a virulence factor, a protein encoded by an antibiotic resistance gene, a protein encoded by a remodeling gene or by a modulatory gene. In a particular embodiment, said given effect is to selectively remove antibiotic resistance from antibiotic resistant bacterial strains.

In a particular embodiment, said nucleic acid of interest is a gene or group of genes encoding one or more exogenous enzyme(s) which result(s) in a genetic modification.

In a particular embodiment, said nucleic acid of interest is a gene encoding a base-editor or a prime-editor.

In some embodiments, the genetic modification is made with one or more of the following enzymes and systems.

Cytosine base editors (CBE) and Adenosine base editors (ABE), as described in Rees et al. (2018) Nat Rev Genet 19:770-788, which is hereby incorporated by reference.

So far there are seven types of DNA base editors described:

Cytosine Base Editor (CBE) that convert C:G into T:A (Komor et al. (2016) Nature 533:420-424)

Adenine Base Editor (ABE) that convert A:T into G:C (Gaudelli et al. (2017) Nature 551:464-471)

Cytosine Guanine Base Editor (CGBE) that convert C:G into G:C (Chen et al. (2020) Biorxiv "Precise and programmable C:G to G:C base editing in genomic DNA"; Kurt et al. (2020) Nat. Biotechnol. "CRISPR C-to-G base editors for inducing targeted DNA transversions in human cells")

Cytosine Adenine Base Editor (CABE) that convert C:G into A:T (Zhao et al. (2020) Nature Biotechnol. "New base editors change C to A in bacteria and C to G in mammalian cells")

Adenine Cytosine Base Editor (ACBE) that convert A:T into C:G (WO2020181180)

Adenine Thymine Base Editor (ATBE) that convert A:T into T:A (WO2020181202)

Thymine Adenine Base Editor (TABE) that convert T:A into A:T (WO2020181193, WO2020181178, WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an E. coli tRNA adenosine deaminase enzyme, able to convert adenosine into Inosine on ssDNA.TadA* include TadA-8a-e and TadA-7.10.

Except from base modification enzyme there has been also modifications implemented to base editor to increase editing efficacy, precision and modularity:

the addition of one or two uracil DNA glycosylase inhibitor domain (UGI) to prevent base excision repair mechanism to revert base edition the addition of Mu-GAM that decrease insertion-deletion rate by inhibiting Non-homologous end joining mechanism in the cell (NHEJ)

the use of nickase active Cas9 (nCas9 D10A) that, by creating nicks on the non-edited strand favor its repair and consequently the fixation of the edited base the use of diverse Cas proteins from for example different organisms, mutants with different PAM motifs or different fidelity or different family (e.g. Cas12a).

Non-limiting examples of DNA based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:

a. A cytosine deaminase (rAPOBEC) and base excision repair proteins (e.g. rXRCC1) (Chen et al. (2020) Biorxiv "Precise and programmable C:G to G:C base editing in genomic DNA").

b. A rat APOBEC1 variant (R33A) protein and an E. coli-derived uracil DNA N-glycosylase (eUNG) (Kurt et al. (2020) Nat. Biotechnol. "CRISPR C-to-G base editors for inducing targeted DNA transversions in human cells").

Cytosine Adenine Base Editors (CABE) consist of a Cas9 nickase, a cytidine deaminase (e.g. AID), and a uracil-DNA glycosylase (Ung) (Zhao et al. (2020) Nature Biotechnol. "New base editors change C to A in bacteria and C to G in mammalian cells").

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193, WO2020181178, WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald et al. (2020) Nature Biotechnol. "A dual-deaminase CRISPR base editor enables concurrent adenine and cytosine editing"; Li et al. (2020) Nature Biotechnol. "Targeted, random mutagenesis of plant genes with dual cytosine and adenine base editors").

Prime editors (PE), as described in Anzalone et al. (2019) Nature 576:149-157, which is hereby incorporated by reference, consist of nCas9 fused to a reverse transcriptase used in combination with a prime editing RNA (pegRNA, a guide RNA that includes a template region for reverse transcription).

Prime Editing allows introduction of insertions, deletions (indels) and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:

a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)

a prime editing guide RNA (pegRNA)

To favor editing the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b.

Cas9 Retron precIse Parallel Editing via homologY ('CRISPEY'), a retron RNA fused to the sgRNA and expressed together with Cas9 and the retron proteins including at least the reverse transcriptase (Sharon et al. (2018) *Cell* 175:544-557.e16).

The SCRIBE strategy: a retron system expressed in combination with a recombinase promoting the recombination of single stranded DNA, also known as single stranded annealing proteins (SSAPs) (Farzadfard & Lu (2014) *Science* 346:1256272). Such recombinases include but are not limited to phage recombinases such as lambda red, recET, Sak, Sak4, and newly described SSAPs described in Wannier et al. (2020) *Proc Natl Acad Sci USA* 117(24):13689-13698 which is hereby incorporated by reference.

The targetron system based on group II introns described in Karberg et al. (2001) *Nat Biotechnol* 19:1162-7, which is hereby incorporated by reference, and which has been adapted to many bacterial species.

Other retron based gene targeting approaches are described in Simon et al. (2019) *Nucleic Acids Res* 47:11007-11019, which is hereby incorporated by reference.

In a particular embodiment, the CRISPR system is included in the nucleic acid of interest. The CRISPR system contains two distinct elements, i.e. i) an endonuclease, in this case the CRISPR associated nuclease (Cas or "CRISPR associated protein") and ii) a guide RNA. The guide RNA may be in the form of a chimeric RNA which consists of the combination of a CRISPR (RNAcr) bacterial RNA and a RNAtracr (trans-activating RNA CRISPR) (Jinek et al. (2012) Science 337(6096):816-21). The guide RNA combines the targeting specificity of the RNAcr corresponding to the "spacing sequences" that serve as guides to the Cas proteins, and the conformational properties of the RNAtracr in a single transcript. When the guide RNA and the Cas protein are expressed simultaneously in the cell, the target genomic sequence can be permanently modified or interrupted. The modification is advantageously guided by a repair matrix. In general, the CRISPR system includes two main classes depending on the nuclease mechanism of action. Class 1 is made of multi-subunit effector complexes and includes type I, III and IV. Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D)

The nucleic acid of interest according to the present disclosure may comprise a nucleic acid sequence encoding Cas protein. A variety of CRISPR enzymes are available for use as a sequence of interest on the plasmid. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. Preferably, the CRISPR enzyme does not make a double strand break. In some embodiments, the CRISPR enzyme makes a single strand break or nicks. In some embodiments, the CRISPR enzyme does not make any break in the DNA or RNA. In one embodiment, a Cas13-deaminase fusion is used to base edit an RNA.

In one embodiment, the CRISPR enzymes may be coupled to a sgRNA. In certain embodiments, the sgRNA targets a gene encoding a given molecule as defined above.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site.

In various embodiments, the invention encompasses fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980, which is hereby incorporated by reference. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163, which is hereby incorporated by reference. In some embodiments, the fusion proteins further comprise an inhibitor of base repair, such as, a nuclease dead inosine specific nuclease (dISN), for example as disclosed in U.S. Pat. No. 10,113,163. In various embodiments, the invention encompasses fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al. (2019) Nature 576:149-157, which is hereby incorporated by reference.

In a particular embodiment, the CRISPR enzyme is any Cas protein, in particular any Cas9 protein, for instance any naturally occurring bacterial Cas9 as well as any variants, chimeras, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA(s).

The sequence encoding Cas9 (the entire protein or a fragment thereof) as used in the context of the disclosure can be obtained from any known Cas9 protein (Fonfara et al. (2014) *Nucleic Acids Res* 42(4):2577-90; Shmakov et al. (2017) *Nat Rev Microbiol* 15(3):169-182). Examples of Cas9 proteins useful in the present disclosure include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SpCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the disclosure can be obtained from any known Cpf1 (Cas12a) protein (Koonin et al. (2017) Current Opinion in Microbiology 37:67-78). Examples of Cpf1(Cas12a) proteins useful in the present disclosure include, but are not limited to, Cpf1 (Cas12a) proteins of *Acidaminococcus* sp, Lachnospiraceae bacteriu and *Francisella novicida.*

The sequence encoding Cas13a (the entire protein or a fragment thereof) can be obtained from any known Cas13a (C2c2) protein (Abudayyeh et al. (2017) Nature 550:280). Examples of Cas13a (C2c2) proteins useful in the present disclosure include, but are not limited to, Cas13a (C2c2) proteins of Leptotrichia *wadei* (LwaCas13a).

The sequence encoding Cas13d (the entire protein or a fragment thereof) can be obtained from any known Cas13d protein (Yan et al. (2018) *Mol Cell* 70(2):327-339). Examples of Cas13d proteins useful in the present disclosure include, but are not limited to, Cas13d proteins of *Eubacterium siraeum* and *Ruminococcus* sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a gene of interest such as, for example, a toxin gene, a virulence factor gene, an antibiotic resistance gene, a remodeling gene or a modulatory gene (cf. WO2014124226 and US2015/0064138).

In some embodiments, the genetic modification is made at the RNA level. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain (ADARDD) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain (ADAR2DD-E488Q for REPAIRv1 and ADAR2DD-E488Q-T375G for REPAIRv2) Cox et al improved specificity and efficiency compare to previous RNA editing strategies. Non-limiting examples of RNA based editor proteins include REPAIRv1, REPAIRv2

In a particular embodiment, the modification is made in a gene selected in the group consisting of an antibiotic resistance gene, virulence factor or protein gene, toxin factor or protein gene, a gene expressing a bacterial receptor, a membrane protein, a structural protein, a secreted protein, and a gene expressing resistance to a drug in general.

In one embodiment, the modification is made to target and inactivate a virulence factor. A virulence factor can be any substance produced by a pathogen that alters host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft.

In another embodiment, the modification is made in an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA p-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, LsaA, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-TolC, MsbA, MsrA,VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In preferred embodiments, the antibiotic is selected from the group consisting of penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; fluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomicin, nalidixice acide, rifampin, derivatives and combination thereof.

When the antibiotic resistance gene is located in the bacterium on a plasmid without addiction systems, it is possible to eliminate the antibiotic resistance by cleavage either in the antibiotic resistance gene or anywhere else in the plasmid.

In another embodiment, the modification is made in a bacterial toxin gene. Bacterial toxins can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococus toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29). In a particular embodiment, said toxin is Shiga toxin.

In some embodiments, the modification is made in a mimic peptide gene sequence so that the homology with the human peptide sequence is reduced, and therefore results in the mimic peptide being not recognized anymore by the host immune system. Mimic peptides of particular interest are bacterial mimic peptides that are associated with autoimmune diseases, for example those mentioned in Negi et al. (2017) *Plos One* 12:e0180518, which are hereby incorporated by reference. Of particular interest are the gene sequences encoding any of the mimic peptides in S1 Table of Negi et al.

In preferred embodiments, the mimic peptide is from Proteobacteria or Firmicutes. Of particular interest are the gene sequences encoding 24 gut bacterial peptides identified by Negi et al. with homology to four human peptides from Low molecular weight phosphotyrosine protein phosphatase, Aldehyde dehydrogenase family 3 member B1, Maleylacetoacetate isomerase and Uracil-DNA glycosylase. These gene sequences can be modified to reduce the homology with the human sequences and prevent cross-reactivity of those recognized by the host immune system with the human counterpart.

In a preferred embodiment, the genetic modification is in the *Bacteroides faecis* or *Bacteroides thetaiotaomicron* beta-galactosidase gene. Preferably, the *Bacteroides faecis* or *Bacteroides thetaiotaomicron* beta-galactosidase protein with the genetic modification shows lower homology with human MYH6 cardiac peptide as compared to the *Bacteroides faecis* or *Bacteroides thetaiotaomicron* beta-galactosidase protein without the genetic modification. Preferably the genetic modification is performed in the peptides fragment recognized as epitope by the human immune system leading to a weaker or absence of epitope recognition by the human immune system.

In a preferred embodiment, the genetic modification is in human commensal bacteria encoding a Ro60 ortholog gene. Preferably, the Ro60 protein resulting from the genetic modification shows lower homology with human Ro60 peptide as compared to the original protein. Preferably the genetic modification is performed in the DNA sequence corresponding to peptides fragment recognized as epitope by the human immune system leading to a weaker or absence of epitope recognition by the human immune system. Preferably the human bacterial commensal targeted for genetic modification are: *Propionibacterium propionicum, Corynebacterium amycolatum, Actinomyces massiliensis, Bacteroides thetaiotaomicron*. Even more preferably the human bacterial commensal targeted for genetic modification is *Propionibacterium propionicum.*

In a preferred embodiment, the genetic modification is in human commensal bacterial DNA sequence encoding a peptide that mimic insulin B 9-25, a self-epitope involved in type 1 diabetes. The genetic mutation reduces homology to the insulin B9-25 epitope SHLVEALYLVCGERGFF (SEQ ID NO: 1). In a preferred embodiment, the target bacteria belong to the Firmicutes phylum. In a preferred embodiment, the target gene in the target bacteria is part of the transketolase N superfamily.

In a preferred embodiment, the genetic modification is in *Roseburia intestinalis* encoding a peptide that mimic the epitope of the autoantigen β2-glycoprotein I (β2GPI), a self-epitope involved in antiphospholipid syndrome (APS). The genetic mutation is reducing homology to the T cell (β2GP1) epitope KVSFFCKNKEKKCSY (SEQ ID NO: 2) and/or B cell epitope VSRGGMRKFIC (SEQ ID NO: 3).

The genetic modification can be in the translated or untranslated regions of a gene. The genetic modification can be in the promoter region of a gene or within any other region involved in gene regulation. In some embodiments, the genetic modification results in the change in at least 1, 2, 3, 4, 5, 6, 7, 8, 9, 10, 11, 12, 13, 14, 15, 20, 25, 30, 35, 40, 45, 50, 100, 200, 500, etc. amino acids to a different amino acid. In some embodiments, the genetic modification introduces a stop codon. In some embodiments, the genetic modification is outside protein coding sequences, within RNA, or within regulatory sequences.

Preferably, the genetic modification does not integrate a phage genome or exogenous DNA into the host bacterial chromosome or endogenous plasmid(s). Preferably, the genetic modification does not result in expression of an exogenous protein from an integrated exogenous DNA in the host bacterial chromosome or endogenous plasmid(s). Most preferably, the genetic modification does not involve either NHEJ or HR endogenous repair mechanism of the host bacteria.

Killing the Receiver Bacterial Cell

In a particular embodiment, said given effect is killing the receiver bacterial cell.

In a particular embodiment, said nucleic acid of interest is a gene encoding a nuclease.

In one embodiment, the nucleic acid of interest is a programmable nuclease circuit to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of different CRISPR-Cas systems classes and types, such as the Type II CRISPR-Cas (Clustered Regularly Interspaced Short Palindromic Repeats-CRISPR-associated) system of *Streptococcus pyogenes*, as disclosed above. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases, as disclosed above. Thus, the programmable nuclease circuit provided herein may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

In a particular embodiment, said nuclease is the Cpf1 nuclease.

In a particular embodiment, said nuclease is the Cas9 nuclease

In a particular embodiment, said nuclease is the Mad4 nuclease, as defined above.

In a particular embodiment, said nuclease is the Mad7 nuclease, as defined above.

In a particular embodiment, said nuclease is the Cms1 nuclease, as defined above.

In a particular embodiment, antibiotic resistant strains are targetly killed by programming the nuclease to perform a DNA cleavage, e.g. a double strand DNA break in an antibiotic resistance gene located on the chromosome of the target bacteria or on a plasmid with addictive systems (toxin/antitoxin).

Other sequences of interest, preferably programmable, can be delivered to targeted bacteria to kill it. For example, the nucleic acid of interest may encode holins or toxins.

In a particular embodiment, said nucleic acid of interest further makes the receiver bacterial cell produce a molecule of interest, as disclosed above, in particular a host modulatory molecule, as disclosed above, before being killed or just after being killed as a bacterial host for instance.

Nucleic Acid of Interest

In the context of the invention, the nucleic acid of interest may be under the control of a promoter.

As known by the person skilled in the art, a promoter may be classified as strong or weak according to its affinity for RNA polymerase. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

It will be appreciated by those of ordinary skill in the art that a promoter sequence may be selected from a large number of known bacterial genes expressed by various bacterial species. Also, methods of prokaryotic promoter prediction exist, and can be based on DNA stability analysis as described in Kanhere and Bansal (BMC Bioinformatics 2005, 6:1). The choice of promoter on the vector according to the present invention can thus be made based on the bacteria to target.

In some embodiments, the nucleic acid of interest may be positioned under the control of a recombinant or heterologous promoter, which refers to a promoter that is not normally associated with the nucleic acid of interest in its natural environment.

Examples of bacterial promoters for use in accordance with the present invention include, without limitation, positively regulated E. coli promoters such as positively regulated a 70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) CIO, P(Rhl), Pu, FecA, pRE, cadC, hns, pLas, pLux), a "s" promoter (e.g., Pdps), σ 32 promoters (e.g., heat shock) and σ 54 promoters (e.g., glnAp2); negatively regulated E. coli promoters such as negatively regulated σ 70 promoters (e.g., Promoter (PRM+), modified lambda Prm promoter, TetR-TetR-4C P(Las) TetO, P(Las) CIO, P(Lac) IQ, RecA_DlexO_D-Lac01, dapAp, FecA, Pspac-hy, pel, plux-cl, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cl, pLux/cl, LacI, LacIQ, pLacIQI, pLas/cl, pLas/Lux, pLux/Las, pRecA with LexA binding site, reverse BBa_R0011, pLacI/ara-1, pLacIq, rrnB PI, cadC, hns, PfhuA, pBad/araC, nhaA, OmpF, RcnR), σ S promoters (e.g., Lutz-Bujard LacO with alternative sigma factor σ 38), σ 32 promoters (e.g., Lutz-Bujard LacO with alternative sigma factor σ 32), a 54 promoters (e.g., glnAp2); negatively regulated B. subtilis promoters such as repressible B. subtilis σ A promoters (e.g., Gram-positive IPTG-inducible, Xyl, hyper-spank), a promoters, and the BioFAB promoters disclosed in Mutalik V K et al (Nature Methods, 2013, 10: 354-360, see in particular the supplementary data) as well as on the BioFAB website (http://biofab.synberc.org/data). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by α70 such as the promoters of the Anderson collection (http://parts.igem.org/Promoters/Catalog/Anderson): BBa_J23100, BBa_J23101, BBa_J23102, BBa_J23103, BBa_J23104, BBa_J23105, BBa_J23106, BBa_J23107, BBa_J23108, BBa_J23109, BBa_J23110, BBa_J23111, BBa_J23112, BBa_J23113, BBa_J23114, BBa_J23115, BBa_J23116, BBa_J23117, BBa_J23118, and BBa_J23119.

Other preferred bacterial promoters are the promoters disclosed in Stanton et al. (2014) Nat. Chem. Biol. 10:99-105, incorporated herein by reference, including in particular TetR, IcaR(A), AmtR, BetI, SrpR, Orf2, BM3R1, ButR, PhlF, PsrA, HlyIIR, AmeR, LmrA, QacR, ScbR, McbR, LitR, HapR, SmcR, TarA and variants thereof. In a particular embodiment, said promoter is SrpR and/or PhlF, or a variant thereof.

In some embodiments of the present invention, a promoter may or may not be used in conjunction with an "enhancer," which refers to a ds-acting regulatory sequence involved in the transcriptional activation of a nucleic acid sequence downstream of the promoter. The enhancer may be located at any functional location before or after the promoter.

In some embodiments, the vector may comprise a terminator sequence, or terminator. A "terminator," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid of interest that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, lambda TI and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

Vector

As used herein, the term "vector" refers to a nucleic acid molecule, typically DNA or RNA that serves to transfer a passenger nucleic acid sequence, i.e. DNA or RNA, into a receiver or target cell. A vector may comprise an origin of replication, a selectable marker, and optionally a suitable site for the insertion of a gene such as the multiple cloning site. There are several common types of vectors including plasmids, bacteriophage genomes, phagemids, phage-plasmids, virus genomes, cosmids, and artificial chromosomes.

In the context of the invention, a vector may be referred to as a payload.

The vector used in the context of the invention may be a plasmid (e.g, a conjugative plasmid capable of transfer into a host cell), phage, phagemid or prophage.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiments, the payload is the delivery vehicle as bacteria are naturally competent to take up a payload from the environment on their own.

As used herein, the terms "phagemid" and "phasmid" are equivalent and refer to a vector that derives from both a plasmid and a bacteriophage genome. A phagemid of the disclosure comprises a phage packaging site and an origin of replication (ori), as disclosed below.

As used herein, the term "packaged phagemid" refers to a phagemid which is encapsidated in a bacteriophage scaffold, bacterial virus particle or capsid. Particularly, it refers to a bacteriophage scaffold, bacterial virus particle or capsid devoid of a bacteriophage genome. The packaged phagemid may be produced with a helper phage strategy, well known from the man skilled in the art. The helper phage comprises all the genes coding for the structural and functional proteins that are indispensable for the phagemid according to the invention to be encapsidated. The packaged phagemid may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

In a particular embodiment, when said vector is a packaged phagemid, said vector does not comprise any element derived from the organism from which the conditional origin of replication is derived. In particular, the packaging site of said vector is not derived from the organism from which the conditional origin of replication is derived.

Vectors can include, without limitation, plasmid vectors and recombinant phage vectors. The skilled artisan is well aware of the genetic elements that must be present on the vector in order to successfully transform and select host cells comprising any of the isolated nucleotides or nucleic acid sequences of the invention.

As used herein, the term "conjugative plasmid" refers to a plasmid that is transferred from one bacterial cell to another during conjugation and a "donor bacterium", as used herein, is then a bacterium that is capable of transferring a conjugative plasmid to another bacterium.

The vector used in the context of the invention is devoid of antibiotic resistance marker.

Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

In a particular embodiment, the vector used in the context of the invention comprises an auxotrophic marker. Auxotrophic markers in bacteria have previously been described, for example, in U.S. Pat. Nos. 4,920,048, 5,691,185, 6,291,245, 6,413,768, and 6,752,994; U.S. Patent Publication No. 20050186666; Struhl et al. (1976) PNAS USA 73; 1471-1475; MacCormick et al., (1995) FEMS Microbiol. Lett. 127:105-109; Dickely et al. (1995) Mol. Microbiol. 15:839-847; Sorensen et al. (2000) Appl. Environ. Microbiol 66:1253-1258; and Fiedler & Skerra (2001) Gene 274: 111 118, all incorporated herein by reference, and typically include DapA and ThyA. In a particular embodiment, said auxotrophic marker is ThyA.

In a particular embodiment, said vector does not comprise any restriction site recognized by restriction enzymes which are frequently encoded by said targeted receiver bacterial cell. In another particular embodiment, said vector comprises no more than 40, 30, 20, 10, 9, 8, 7, 6, 5, 4, 3, 2 or 1 restriction site(s) recognized by restriction enzymes which are frequently encoded by said targeted bacterial cell or a population or a group of targeted bacterial cell(s).

As used herein, the terms "restriction site" and "restriction enzyme site" are equivalent and refer to locations on a nucleic acid containing specific sequences of nucleotides, which are recognized by restriction enzymes. In particular, the nucleic acid comprises specific sequences which are bound and cleaved by restriction enzymes. Restriction sites are generally palindromic sequences of 4-8 base pairs in length. More precisely, the restriction site refers to a particular sequence and a modification state, so as to be bound and cleaved by restriction enzymes. In particular, it refers to a particular unmodified sequence, so as to be bound and cleaved by restriction enzymes. Especially the sequence is not methylated, hydroxymethylated and glucosyl-hydroxymethylated. In this context, the restriction enzyme is of type I, II or III. Alternatively, it may refer to a particular modified sequence, so as to be bound and cleaved by restriction enzymes, for instance a methylated, hydroxymethylated and glucosyl-hydroxymethylated DNA. In this context, the restriction enzyme is of type IV.

As used herein, "recognized by" with respect to a restriction site and a restriction enzyme means that the restriction site is cleaved by the restriction enzyme.

In a restriction site sequence N means that the nucleotide can be A, C, G or T; B means that the nucleotide can be C, G or T; Y means that the nucleotide can be C or T; W means that the nucleotide can be A or T; R means that the nucleotide can be A or G; and D means A, G or T.

As used herein, the terms "restriction enzyme" and "restriction endonuclease" are equivalent and refer to an enzyme that cuts nucleic acids at or near restriction sites. Restriction enzymes are commonly classified into four types (types I to type IV). The REBASE database allow to list the restriction sites that a given bacterium can recognize according to the restriction enzymes that it expresses.

By "frequent" or "frequently" in a group of bacteria of interest is meant that at least 10, 20, 30, 40, 50, 60, 70, 75, 80, 85, 90, 95 or 99% of the bacteria of the group encode the restriction enzyme.

The vector according to the invention, preferably included into a delivery vehicle, preferably a bacteriophage capsid, preferably comprises no more than 100 restriction sites. In a preferred embodiment, the vector according to the invention, preferably included in a delivery vehicle, comprises no more than 10 restriction sites. In a most preferred embodiment, the vector according to the invention, preferably included in a delivery vehicle, does not comprise any restriction site.

The present invention also concerns a nucleic acid vector, as defined above, for use in in vivo delivery of a nucleic acid of interest, as defined above, into a targeted receiver bacterial cell, said nucleic acid of interest producing a given effect on said targeted receiver bacterial cell, wherein said vector comprises:
said nucleic acid of interest, as defined above, and
a conditional origin of replication which is inactive in the targeted receiver bacterial cell but is active in a donor bacterial cell, and
wherein said vector is devoid of antibiotic resistance marker.

Conditional Origin of Replication

The vector of the invention comprises a conditional origin of replication which is inactive in the targeted receiver bacterial cell but is active in a donor bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication of said origin of replication may further depend on a process, such as transcription, to activate said replication.

In the context of the invention, said conditional origin of replication is inactive in the targeted receiver bacterial cell because of the absence of said given protein, peptid, RNA, nucleic acid, molecule or any combination thereof in said receiver bacterial cell.

In a particular embodiment, said conditional origin of replication is active in said donor bacterial cell because said donor bacterial cell expresses said given protein, peptid, RNA, nucleic acid, molecule or any combination thereof. In a particular embodiment, said protein, peptid, RNA nucleic acid, molecule or any combination thereof is expressed in trans in said donor bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a plasmid. In a particular embodiment, said plasmid comprises an antibiotic resistance marker. In an alternative embodiment, said plasmid is devoid of antibiotic resistance marker.

Since said conditional origin of replication is inactive in the targeted receiver bacterial cell because of the absence of said given protein, peptid, RNA, nucleic acid, molecule or any combination thereof in said receiver bacterial cell, said conditional origin of replication may be selected depending on the specific receiver bacterial cell to be targeted.

The conditional origin of replication used according to the present invention may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, P4, lambda, phi82, phi80.

In a particular embodiment, said conditional origin of replication is selected from the group consisting of the R6Kλ DNA replication origin and derivatives thereof, the IncPa oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host microbiome, in particular of the bacteria representing more than 50%, more particularly more than 60%, more than 70%, more than 80%, more than 90% or more than 95% of the host microbiome.

In the context of the invention, the term "phage-inducible chromosomal islands" or "PICIs" are mobile genetic elements having a conserved gene organization, and encode a pair of divergent regulatory genes, including a PICI master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

The present inventors indeed designed herein a particular conditional origin of replication derived from PICIs.

The present inventors showed that it is possible to derive novel conditionally replicative plasmids, in particular based on the primase-helicase and origin of replication from PICIs. These origins may be relatively rare in target strains, and more advantageously the primase-ori pair may be unique for each PICI, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) The ISME Journal 12:2114-2128.

In a particular embodiment, said conditional origin of replication is the primase ori from the PICI of the *Escherichia coli* strain CFT073, typically of sequence SEQ ID NO: 4.

In another particular embodiment, said conditional origin of replication is the primase ori from he PICI of the

*Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNNTGG (SEQ ID NO: 5), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase ori from the PICI of the *Escherichia coli* strain CFT073, devoid of the restriction site GAAABCC. Preferably, said conditional origin of replication is of sequence SEQ ID NO: 6.

In another particular embodiment, said conditional origin of replication is the primase ori from he PICI of the *Escherichia coli* strain CFT073 devoid of the restriction sites selected from the group consisting of GAAABCC, GCCGGC, RCCGGY, GCNGC, TWCANNNNNNTGG (SEQ ID NO: 5), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 7.

In a particular embodiment, wherein said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 8, typically encoded by a nucleic acid comprising or consisting of the sequence SEQ ID NO: 9.

The inventors demonstrated that these specific conditional origins of replication were particularly compatible with lambda-based packaging, leading to sufficiently high titers ($>10^{10}$/mL) required for microbiota-related applications.

In a particular embodiment, the vector of the invention comprises or consists of the sequence SEQ ID NO: 10. In another particular embodiment, the vector of the invention comprises or consists of the sequence SEQ ID NO: 11.

In a particular embodiment, when said vector is a phagemid, said origin of replication may be derived from a microorganism which is different from the one that is used to encode the structural elements of the capsid packaging said phagemid.

Bacterial Delivery Vehicle

In a particular embodiment, said vector is located inside a bacterial delivery vehicle. Preferably, the vector located inside a delivery vehicle is a phagemid and the delivery vehicle is a bacterial virus particle or a capsid.

As used herein, the term «delivery vehicle» refers to any vehicle that allows the transfer of a vector or payload into a bacterium.

There are several types of delivery vehicle encompassed by the present invention including, without limitation, bacteriophage scaffold, virus scaffold, bacterial virus particle, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiments, the delivery vehicle is the vector or payload as bacteria are naturally competent to take up a payload from the environment on their own.

The present disclosure is directed to a bacterial delivery vehicle containing the vector or payload as described herein. The bacterial delivery vehicles are typically prepared from bacterial virus. The bacterial delivery vehicles are typically chosen in order to be able to introduce the vector into the targeted bacteria.

Bacterial viruses, from which the bacterial delivery vehicles disclosed herein may be derived, include bacteriophages. Optionally, the bacteriophage is selected from the Order Caudovirales consisting of, based on the taxonomy of Krupovic et al, Arch Virol, 2015, the family Myoviridae, the family Podoviridae, the family Siphoviridae, and the family Ackermannviridae.

Bacteriophages may be selected from the family Myoviridae (such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus).

Bacteriophages may be selected from the family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, T12011virus, Bcep22virus, Bpp1virus, Cba41virus, Dfl12virus, Ea92virus, Epsilon15virus, F116virus, G7cvirus, Jwalphavirus, Kf1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus).

Bacteriophages may be selected from the family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, Tlsvirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjw1virus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dt1virus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus).

Bacteriophages may be selected from the family Ackermannviridae (such as, without limitation, genus Ag3virus, Limestonevirus, Cba120virus and Vi1virus).

Optionally, the bacteriophage is not part of the order Caudovirales but from families with unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

Optionally, the bacteriophage is targeting Archea not part of the Order Caudovirales but from families with unassigned order such as, without limitation, Ampullaviridae, Fuselloviridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-1, Av-2, Av-3, BF307, CT1, CT2, CT3, CT4, CT6, CT7, CT8 and 1281.

Bacteria of the genus *Aeromonas* can be infected by the following phages: AA-, Aeh2, N, PMI, TP446, 3, 4, 11, 13, 29, 31, 32, 37, 43, 43-10T, 51, 54, 55R.1, 56, 56RR2, 57, 58, 59.1, 60, 63, AehI, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizI, AI-K-I, B, BCJAI, BCI, BC2, BLLI, BLI, BP142, BSLI, BSL2, BSI, BS3, BS8, BS15, BS18, BS22, BS26, BS28, BS31, BS104, BS105, BS106, BTB, B1715V1, C, CK-1, ColI, CorI, CP-53, CS-1, CSi, D, D, D, D5, entI, FP8, FP9, FSi, FS2, FS3, FS5, FS8, FS9, G, GH8, GT8, GV-1, GV-2, GT-4, g3, g12, g13, g14, g16, g17, g21, g23, g24, g29, H2, kenI, KK-88, KumI, KyuI, J7W-1, LP52, (syn=LP-52), L7, MexI, MJ-I, mor2, MP-7, MPIO, MP12, MP14, MP15, NeoI, N°2, N5, N6P, PBCI, PBLA, PBPI, P2, S-a, SF2, SF6, ShaI, SilI, SP02, (syn=ΦSPP1), SPβ, STI, STi, SU-II, t, TbI, Tb2, Tb5, TblO, Tb26, Tb51, Tb53, Tb55, Tb77, Tb97, Tb99, Tb560, Tb595, Td8, Td6, Tdl5, TgI, Tg4, Tg6, Tg7, Tg9, TglO, TglI, Tgl3, Tgl5, Tg21, TinI, Tin7, Tin8, Tin13, Tm3, TocI, TogI, toII, TP-1, TP-10vir, TP-15c, TP-16c, TP-17c, TP-19, TP35, TP51, TP-84, Tt4, Tt6, type A, type B, type C, type D, type E, TP3, VA-9, W, wx23, wx26, YunI, α, γ, pl I, φmed-2, φT, pp-4, φ3T, φ75, φIO5, (syn=φIO5), IA, IB, 1-97A, 1-97B, 2, 2, 3, 3, 3, 5, 12, 14, 20, 30, 35, 36, 37, 38, 41C, 51, 63, 64, 138D, 1, 11, IV, NN-*Bacillus* (13), aleI, ARI, AR2, AR3, AR7, AR9, Bace-11, (syn=11), Bastille, BLI, BL2, BL3, BL4, BL5, BL6, BL8, BL9, BP124, BS28, BS80, Ch, CP-51, CP-54, D-5, darI, denI, DP-7, entI, FoSi, FoS2, FS4, FS6, FS7, G, gall, gamma, GEI, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No.I, N17, N19, PBSI, PKI, PMBI, PMB12, PMJI, S, SPOI, SP3, SP5, SP6, SP7, SP8, SP9, SPIO, SP-15, SP50, (syn=SP-50), SP82, SST, subI, SW, Tg8, Tg12, Tgl3, Tg14, thuI, thuA, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, 111, 4 (*B. megateriwn*), 4 (*B. sphaericus*), AR13, BPP-IO, BS32, BS107, BI, B2, GA-1, GP-IO, GV-3, GV-5, g8, MP20, MP27, MP49, Nf, PP5, PP6, SF5, TgI8, TP-I, Versailles, φI5, φ29, 1-97, 837/IV, mï-*Bacillus* (1), BatIO, BSLIO, BSLI 1, BS6, BSI 1, BS16, BS23, BSIOI, BS102, gI8, morI, PBLI, SN45, thu2, thu3, Tml, Tm2, TP-20, TP21, TP52, type F, type G, type IV, HN-BacMus (3), BLE, (syn=θc), BS2, BS4, BS5, BS7, BIO, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: ad I2, Baf-44, Baf-48B, Baf-64, Bf-1, Bf-52, B40-8, FI, βI, φAI, φBrOI, φBrO2, 11, 67.1, 67.3, 68.1, mt-*Bacteroides* (3), Bf42, Bf71, HN-*Bdellovibrio* (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FOI), (syn=FQI), D, FP2, (syn=FP2), (syn=FD2), Fz, (syn=Fz75/13), (syn=Firenze 75/13), (syn=Fi), Fi, (syn=FI), Fim, (syn=Flm), (syn=Fim), FiU, (syn=FIU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=FIO), 371/XXIX, (syn=371), (syn=Fn), (syn=FI I) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phages: ChpI.

Bacteria of the genus *Clostridium* can be infected by the following phages: CAKI, CA5, Ca7, CEβ, (syn=1C), CEγ, CldI, c-n71, c-203 Tox-, DEβ, (syn=ID), (syn=IDt0X+), HM3, KMI, KT, Ms, NAI, (syn=Naltox+), PA135Oe, Pfó, PL73, PL78, PL81, PI, P50, P5771, P19402, ICt0X+, 2Ct0X\ 2D3 (syn=2Dt0X+), 3C, (syn=3Ctox+), 4C, (syn=4Ct0X+), 56, III-I, NN-*Clostridium* (61), NBltOX+, αI, CAI, HMT, HM2, PFI5 P-23, P-46, Q-05, Q-oe, Q-16, Q-21, Q-26, Q-40, Q-46, S111, SA02, WA01, WA03, Wm, W523, 80, C, CA2, CA3, CPTI, CPT4, cl, c4, c5, HM7, H11/A1, H18/Ax, FWS23, Hi58ZA1, K2ZA1, K21ZS23, ML, NA2tOX; Pf2, Pf3, Pf4, S9ZS3, S41ZA1, S44ZS23, α2, 41, 112ZS23, 214/S23, 233/Ai, 234/S23, 235/S23, II-I, II-2, II-3, NN-*Clostridium* (12), CAI, FI, K, S2, 1, 5 and NN-*Clostridium* (8).

Bacteria of the genus *Corynebacterium* can be infected by the following phages: CGKI (defective), A, A2, A3, AIOI, A128, A133, A137, A139, A155, A182, B, BF, B17, B18, B51, B271, B275, B276, B277, B279, B282, C, capi, CCI, CGI, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γI9, δ, (syn=δ'ox+), p, (syn=ptoχ-), D9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* can be infected by the following phages: DF78, FI, F2, 1, 2, 4, 14, 41, 867, DI, SB24, 2BV, 182, 225, C2, C2F, E3, E62, DS96, H24, M35, P3, P9, SBIOI, S2, 2BII, 5, 182a, 705, 873, 881, 940, 1051, 1057, 21096C, NN-*Enterococcus* (1), PEI, FI, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, EI, E24, E41, FI-2, FI-4, FI-5, HI8A, Ffl8B, i, MM, Mu, (syn=mu), (syn=MuI), (syn=Mu-I), (syn=MU-I), (syn=MuI), (syn=p), 025, Phl-5, Pk, PSP3, PI, PID, P2, P4 (defective), SI, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, FI3, H, HI, H3, H8, K3, M, N, ND-2, ND-3, ND4, ND-5, ND6, ND-7, Ox-I (syn=OXI), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, Phl-I, RB42, RB43, RB49, RB69, S, Sal-I, Sal-2, Sal-3, Sal-4, Sal-5, Sal-6, TC23, TC45, TulI*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, αI, 1, IA, 3, (syn=Ac3), 3A, 3T+, (syn=3), (syn=MI), 5φ, (syn=φ5), 9266Q, CFO103, HK620, J, K, KIF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φI, φI.2, φ20, φ95, φ263, φIO92, φI, φII, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, FI, F26S, F27S, Hi, HK022, HK97, (syn=ΦHK97), HK139, HK253, HK256, K7, ND-I, no.D, PA-2, q, S2, TI, (syn=a), (syn=P28), (syn=T-I), (syn=Tx), T3C, T5, (syn=T-5), (syn=T5), UC-I, w, β4, γ2, λ (syn=lambda), (syn=Φλ), ΦD326, φγ, Φ06, 0Φ7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, H K243, KIO, ZG/3A, 5, 5A, 21EL, H19-J and 933H.

Bacteria of the genus *Fusobacterium* can be infected by the following phages: NN-*Fusobacterium* (2), fv83-554/3, fv88-531/2, 227, fv2377, fv2527 and fv8501.

Bacteria of the genus *Haemophilus* can be infected by the following phages: HPI, S2 and N3.

Bacteria of the genus *Helicobacter* can be infected by the following phages: HPI and ˆˆ-*Helicobacter* (1).

Bacteria of the genus *Klebsiella* can be infected by the following phages: AIO-2, KI4B, KI6B, KI9, (syn=K19), KI14, KI15, KI21, KI28, KI29, KI32, KI33, KI35, KI106B, KI171B, KI181B, KI832B, AIO-I, AO-I, AO-2, AO-3, FC3-10, K, KI1, (syn=KII), KI2, (syn=K12), KI3, (syn=K13), (syn=KI 70/11), KI4, (syn=K14), KI5, (syn=K15), KI6, (syn=K16), KI7, (syn=K17), KI8, (syn=KI8), KI19, (syn=K19), KI27, (syn=K127), KI31, (syn=K131), KI35, KI171B, II, VI, IX, CI-I, KI4B, KI8, KI11, KI12, KI13, KI16, KI17, KI18, KI20, KI22, KI23, KI24, KI26, KI30, KI34, KI106B, KIi65B, KI328B, KLXI, K328, P5046, 11, 380, III, IV, VII, VIII, FC3-11, KI2B, (syn=K12B), K125, (syn=K125), K142B, (syn=K142), (syn=K142B), K1181B, (syn=KII 81), (syn=K1181B), K1765/!, (syn=K1765/1), KI842B, (syn=K1832B), KI937B, (syn=K1937B), LI, φ28, 7, 231, 483, 490, 632 and 864/100.

Bacteria of the genus *Lepitospira* can be infected by the following phages: LEI, LE3, LE4 and ~NN-*Leptospira* (1).

Bacteria of the genus *Listeria* can be infected by the following phages: A511, 01761, 4211, 4286, (syn=BO54), A005, A006, A020, A500, A502, A511, AI 18, A620, A640, B012, B021, B024, B025, B035, B051, B053, B054, B055, B056, BIOI, BI IO, B545, B604, B653, C707, D441, HSO47, HIOG, H8/73, H19, H21, H43, H46, H107, H108, HI IO, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* can be infected by the following phage: 47.

Bacteria of the genus *Mycobacterium* can be infected by the following phages: 13, AGI, ALi, ATCC 11759, A2, B.C3, BG2, BKI, BK5, *butyricum*, B-I, B5, B7, B30, B35, Clark, CI, C2, DNAIII, DSP1, D4, D29, GS4E, (syn=GS4E), GS7, (syn=GS-7), (syn=GS7), Pa, lacticola, Legendre, Leo, L5, (syn=ΦL-5), MC-I, MC-3, MC-4, minetti, MTPHI I, Mx4, MyF3P/59a, phlei, (syn=phlei 1), phlei 4, Polonus II, rabinovitschi, *smegmatis*, TM4, TM9, TMIO, TM20, Y7, YIO, φ630, IB, IF, IH, 1/1, 67, 106, 1430, BI, (syn=Bol), B24, D, D29, F-K, F-S, HP, Polonus I, Roy, RI, (syn=RI-Myb), (syn=Ri), 11, 31, 40, 50, 103a, 103b, 128, 3111-D, 3215-D and NN-*Mycobacterium* (1).

Bacteria of the genus *Neisseria* can be infected by the following phages: Group I, group II and NPI.

Bacteria of the genus *Nocardia* can be infected by the following phages: MNP8, NJ-L, NS-8, N5 and TtiN-*Nocardia*.

Bacteria of the genus *Proteus* can be infected by the following phages: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI I, Pv2, πI, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* can be infected by the following phages: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* can be infected by the following phages: Pfl, (syn=Pf-I), Pf2, Pf3, PP7, PRRI, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PBI), pfl6, PMN17, PPI, PP8, PsaI, PsPI, PsP2, PsP3, PsP4, PsP5, PS3, PS17, PTB80, PX4, PX7, PYOI, PYO2, PYO5, PYO6, PYO9, PYOIO, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, PIK, SLPI, SL2, S2, UNL-I, wy, Yai, Ya4, Yan, φBE, φCTX, φC17, φKZ, (syn=ΦKZ), T-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, FI 16, HF, H90, K5, K6, KI 04, K109, K166, K267, N4, N5, 06N-25P, PE69, Pf, PPN25, PPN35, PPN89, PPN91, PP2, PP3, PP4, PP6, PP7, PP8, PP56, PP87, PPI 14, PP206, PP207, PP306, PP651, Psp231a, Pssy401, Pssy9220, psi, PTB2, PTB20, PTB42, PXI, PX3, PXIO, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-1, C22, D3, D37, D40, D62, D3112, F7, FIO, g, gd, ge, gξ Hwl2, Jb 19, KFI, L°, OXN-32P, O6N-52P, PCH-1, PC13-1, PC35-1, PH2, PH51, PH93, PH132, PMW, PM13, PM57, PM61, PM62, PM63, PM69, PM105, PMI 13, PM681, PM682, P04, PPI, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-10, Pz, SDI, SLI, SL3, SL5, SM, φC5, φCI I, φCI I-1, φC13, φC15, φMO, φX, φO4, φI I, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), GIOI, M6, M6a, LI, PB2, Pssyl5, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* can be infected by the following phage: NN-*Rickettsia*.

Bacteria of the genus *Salmonella* can be infected by the following phages: b, Beccles, CT, d, Dundee, f, Fels 2, GI, GUI, GVI, GVIII, k, K, i, j, L, 01, (syn=0-1), (syn=O1), (syn=O-I), (syn=7), 02, 03, P3, P9a, PIO, Sab3, Sab5, SanIS, SanI7, SI, Taunton, Vil, (syn=Vil), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22aI, P22-4, P22-7, P22-11, SNT-I, SNT-2, SP6, Villi, ViIV, ViV, ViVI, ViVII, Worksop, Sj5, ε34, 1,37, 1(40), (syn=φI[40]), 1,422, 2, 2.5, 3b, 4, 5, 6,14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, P22-1, P22-3, P22-12, SabI, Sab2, Sab2, Sab4, SanI, San2, San3, San4, San6, San7, San8, San9, SanI3, SanI4, SanI6, SanI8, SanI9, San20, San21, San22, San23, San24, San25, San26, SasLI, SasL2, SasL3, SasL4, SasL5, SIBL, SII, ViII, φI, 1, 2, 3a, 3al, 1010, Ym-*Salmonella* (1), N-4, SasL6 and 27.

Bacteria of the genus *Serratia* can be infected by the following phages: A2P, PS20, SMB3, SMP, SMP5, SM2, V40, V56, ic, ΦCP-3, ΦCP-6, 3M, 10/Ia, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, ΦCWI, ΦCP6-1, ΦCP6-2, ΦCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/1Oa, L.359 and SMBI.

Bacteria of the genus *Shigella* can be infected by the following phages: Fsa, (syn=a), FSD2d, (syn=D2d), (syn=W2d), FSD2E, (syn=W2e), fv, F6, f7.8, H-Sh, PE5, P90, SflI, Sh, SHm, SHrv, (syn=HIV), SHvi, (syn=HVI), SHVvm, (syn=HVIII), SKy66, (syn=gamma 66), (syn=yββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVfl-A, (syn=SvmA), (syn=VIIIA), STvi, STK, STx1, STxn, S66, W2, (syn=D2c), (syn=D20), φI, φIVb 3-SO-R, 8368-SO-R, F7, (syn=FS7), (syn=K29), FIO, (syn=FSIO), (syn=K31), 11, (syn=alfa), (syn=FSa), (syn=KI 8), (syn=a), 12, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO-S-R), W1, (syn=D8), (syn=FSD8), W2a, (syn=D2A), (syn=FS2a), DD-2, Sf6, FSi, (syn=FI), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), P2, BII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI I, P2-SO-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=Ssl), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STffl, STrv, STVi, STvπ, S70, S206, U2-SO-S, 3210-SO-S, 3859-SO-S, 4020-SO-S, φ3, φ5, φ7, φ8, φ9, φIO, φI I, φI3, φI4, φI8, SHm, (syn=Hπi), SHχi, (syn=HXt) and SKxI, (syn=KXI), (syn=Sχi), (syn=SsXI), (syn=XI).

Bacteria of the genus *Staphylococcus* can be infected by the following phages: A, EW, K, Ph5, Ph9, PhIO, PhI3, PI, P2, P3, P4, P8, P9, PIO, RG, SB-i, (syn=Sb-I), S3K, Twort, ΦSK311, φ812, 06, 40, 58, 119, 130, 131, 200, 1623, STCI, (syn=stcl), STC2, (syn=stc2), 44AHJD, 68, ACI, AC2, A6"C", A9"C", b581, CA-I, CA-2, CA-3, CA-4, CA-5, DI I, L39x35, L54a, M42, NI, N2, N3, N4, N5, N7, N8, NIO, Ni I, N12, N13, N14, N16, Ph6, PhI2, PhI4, UC-18, U4, U15, SI, S2, S3, S4, S5, X2, Z1, φB5-2, φD, ω, 11, (syn=φI I), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AIO, A13, b594n, D, HK2, N9, N15, P52, P87, SI, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* can be infected by the following phages: EJ-1, NN-Streptococais (1), a, CI, FL0Ths, H39, Cp-I, Cp-5, Cp-7, Cp-9, Cp-IO, AT298, A5, aIO/JI, aIO/J2, aIO/J5, aIO/J9, A25, BTI I, b6, CAI, c20-1, c20-2, DP-I, Dp-4, DTI, ET42, eIO, FA101, FEThs, $F_K$, FKKIOI, FKLIO, FKP74, FKH, FLOThs, FyIOI, fl, F10, F20140/76, g, GT-234, HB3, (syn=HB-3), HB-623, HB-746, M102, O1205, φO1205, PST, PO, PI, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfiI 1, (syn=SFil I), (syn=φSFilI), (syn=CDSfil I), (syn=φSfil I), sfiI9, (syn=SFiI9), (syn=φSFiI9), (syn=pSfiI9), Sfi21, (syn=SFi21), (syn=φSFi21), (syn=φSfi21), ST0, STX, st2, ST2, ST4, S3, (syn=φS3), s265, Φ17, φ42, φ57, φ80, φ81, φ82, φ83, φ84, φ85, φ86, φ87, φ88, φ89, φ90, φ91, φ92, φ93, φ94, φ95, φ96, φ97, φ98, φ99, φIOO, φIOI, φIO2, φ227, Φ7201, ω1, ω2, ω3, ω4, ω5, ω6, ω8, ωIO, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and m*Streptococcus* (34).

Bacteria of the genus *Treponema* can be infected by the following phage: NN-*Treponema* (1).

Bacteria of the genus *Vibrio* can be infected by the following phages: CTXΦ, fs, (syn=si), fs2, Ivpf5, Vfl2, Vf33, VPIΦ, VSK, v6, 493, CP-TI, ET25, kappa, K139, Labol, )XN-69P, OXN-86, O6N-21P, PB-I, P147, rp-1, SE3, VA-1, (syn=VcA-1), VcA-2, VPI, VP2, VP4, VP7, VP8, VP9, VPIO, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHCl-1, ΦHCl-2, ΦHCl-3, ΦHC1-4, ΦHC2-1, >HC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φI38, 1-II, 5, 13, 14, 16, 24, 32, 493, 6214, 7050, 7227, II, (syn=group II), (syn==p2), V, VIII, ~m-*Vibrio* (13), KVP20, KVP40, nt-1, 06N-22P, P68, el, e2, e3, e4, e5, FK, G, I, K, nt-6, NI, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, 1 (syn=group 1), III (syn=group III), VI, (syn=A-Saratov), VII, IX, X, HN-*Vibrio* (6), pAI, 7, 7-8, 70A-2, 71A-6, 72A-5, 72A-8, 108A-10, 109A-6, 109A-8, IIOA-1, 110A-5, 110A-7, hv-1, OXN-52P, P13, P38, P53, P65, P108, PiII, TP13 VP3, VP6, VP12, VP13, 70A-3, 70A-4, 70A-10, 72A-1, 108A-3, 109-B1, 110A-2, 149, (syn=p149), IV, (syn=group IV), NN-*Vibrio* (22), VP5, VPII, VP15, VP16, αI, α2, α3a, α3b, 353B and HN-*Vibrio* (7).

Bacteria of the genus *Yersinia* can be infected by the following phages: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

In an embodiment, the bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus PhaxI, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus Vil, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPtl0, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus Felix01, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus JS09, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, *Cronobacter* virus CR3, *Cronobacter* virus CR8, *Cronobacter* virus CR9, *Cronobacter* virus PBES02, *Pectobacterium* virus phiTE, *Cronobacter* virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Eral03, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus gh1, *Prochlorococcus* virus PSSP7, *Synechococcus* virus P60, *Synechococcus* virus Syn5, *Streptococcus* virus Cp1, *Streptococcus* virus Cp7, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepil02, *Burkholderia* virus Bcepmigl, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961 P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VP5, *Streptomyces* virus Amela, *Streptomyces* virus phi-CAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wksl3, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, *Cronobacter* virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus blL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSL-SPO30, *Salmonella* virus FSLSPO88, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus SO1, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littleе, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151 N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PB11, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus blL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sal2, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phil7, *Xanthomonas* virus Xop411, *Xanthomonas* virus Xp10, *Streptomyces* virus TP1604, *Streptomyces* virus YDN12, Alphaproteobacteria virus phiJI001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, *Acholeplasma* virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, *Spiroplasma* virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, *Spiroplasma* virus C74, *Spiroplasma* virus R8A2B, *Spiroplasma* virus SkV1CR23x, *Escherichia* virus F1, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus ID52, *Escherichia* virus Talmos, *Escherichia* virus phiX174, *Bdellovibrio* virus MAC1, *Bdellovibrio* virus MH2K, *Chlamydia* virus Chp1, *Chlamydia* virus Chp2, *Chlamydia* virus CPAR39, *Chlamydia* virus CPG1, *Spiroplasma* virus SpV4, *Acholeplasma* virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stx1phi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus EC026_P06, *Escherichia* virus ECO103_P15, *Escherichia* virus ECO103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Sp5.

In one embodiment, the bacterial virus particles typically target *E. coli* and include the capsid of a bacteriophage selected in the group consisting of BW73, B278, D6, D108, E, EI, E24, E41, FI-2, FI-4, FI-5, HI8A, Ff18B, i, MM, Mu, 025, Phl-5, Pk, PSP3, PI, PID, P2, P4, SI, Wφ, φK13, φI, φ2, φ7, φ92, 7 A, 8φ, 9φ, 18, 28-1, 186, 299, HH-*Escherichia* (2), AB48, CM, C4, C16, DD-VI, E4, E7, E28, FII, F13, H, HI, H3, H8, K3, M, N, ND-2, ND-3, ND4, ND-5, ND6, ND-7, Ox-I, Ox-2, Ox-3, Ox-4, Ox-5, Ox-6, Phl-I, RB42, RB43, RB49, RB69, S, Sal-I, Sal-2, Sal-3, Sal-4, Sal-5, Sal-6, TC23, TC45, TulI*-6, TulP-24, TulI*46, TulP-60, T2, T4, T6, T35, al, 1, IA, 3, 3A, 3T+, 5φ, 9266Q, CFO103, HK620, J, K, KIF, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φI, φI.2, φ20, φ95, φ263, φIO92, φI, φII, Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, F1, F26S, F27S, Hi, HK022, HK97, HK139, HK253, HK256, K7, ND-I, PA-2, q, S2, TI, ), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J and 933H.

The present invention thus also concerns a bacterial delivery vehicle, as defined above, for use in in vivo delivery of a nucleic acid of interest into a targeted receiver bacterial cell, as defined above, wherein said bacterial delivery vehicle comprises the vector of the invention.

Donor Bacterial Cell

In the context of the application, the term "donor bacterial cell" refers to a bacterial cell hosting a vector or a plasmid, to a production cell line or to a bacterium that is capable of transferring a conjugative plasmid to another bacterium.

The present invention also concerns a donor bacterial cell comprising the vector of the invention or producing the bacterial delivery vehicle of the invention, wherein said donor bacterial cell stably comprises the vector of the invention and is able to replicate said vector.

In a particular embodiment, when the conditional origin of replication of said vector is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof. Preferably, said protein, peptid, nucleic acid, RNA, molecule or any combination thereof is expressed in trans, as defined in the section "Conditional origin of replication" above.

In a particular embodiment, said donor bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 8.

In a particular embodiment, said donor bacterial cell stably comprises a nucleic acid encoding said rep protein, in particular said primase-helicase, said nucleic acid typically comprising or consisting of the sequence SEQ ID NO: 9.

In a particular embodiment, said donor bacterial cell is a production cell line, in particular a cell line producing packaged phagemids including the vector of the invention.

Generation of packaged phagemids and bacteriophage particles by production cell lines are routine techniques well-known to one skilled in the art. In an embodiment, a satellite phage and/or helper phage may be used to promote the packaging of the vector in the delivery vehicles disclosed herein. Helper phages provide functions in trans and are well known to the man skilled in the art. The helper phage comprises all the genes coding for the structural and functional proteins that are indispensable for the phagemid to be packaged, (i.e. the helper phage provides all the necessary gene products for the assembly of the delivery vehicle). The helper phage may contain a defective origin of replication or packaging signal, or completely lack the latter, and hence it is incapable of self-packaging, thus only bacterial delivery particles carrying the vector or plasmid will be produced. Helper phages may be chosen so that they cannot induce lysis of the bacterial cells used for the delivery particle production. One skilled in the art would understand that some bacteriophages are defective and need a helper phage for payload packaging. Thus, depending on the bacteriophage chosen to prepare the bacterial delivery particles, the person skilled in the art would know if a helper phage is required. Sequences coding for one or more proteins or regulatory processes necessary for the assembly or production of packaged payloads may be supplied in trans. For example, STF, gpJ and gpH proteins may be provided in a plasmid under the control of an inducible promoter or expressed constitutively. In this case, the phage wild-type sequence may or not contain a deletion of the gene or sequence supplied in trans. Additionally, chimeric or modified phage sequences encoding a new function, like an engineered STF, gpJ or gpH protein, may be directly inserted into the desired position in the genome of the helper phage, hence bypassing the necessity of providing the modified sequence in trans. Methods for both supplying a sequence or protein in trans in the form of a plasmid, as well as methods to generate direct genomic insertions, modifications and mutations are well known to those skilled in the art.

In a particular embodiment, said helper phage comprises a nucleic acid sequence encoding a chimeric STF comprising or consisting of the sequence SEQ ID NO: 12, said nucleic acid sequence typically comprising or consisting of the sequence SEQ ID NO: 13, and said helper phage optionally further comprises a nucleic acid sequence encoding a chimeric gpJ variant comprising or consisting of the sequence SEQ ID NO: 14, said nucleic acid sequence typically comprising or consisting of the sequence SEQ ID NO: 15.

In a particular embodiment, said helper phage is a lambda prophage wherein (i) the nucleic acid encoding a wild-type STF protein has been replaced by a nucleic acid sequence encoding a chimeric STF comprising or consisting of the sequence SEQ ID NO: 12, said nucleic acid sequence typically comprising or consisting of the sequence SEQ ID NO: 13, (ii) the nucleic acid encoding a wild-type gpJ protein has been replaced by a nucleic acid sequence encoding a chimeric gpJ variant comprising or consisting of the sequence SEQ ID NO: 14, said nucleic acid sequence typically comprising or consisting of the sequence SEQ ID NO: 15, and (iii) the Cos site has been removed, and wherein optionally (iv) the helper prophage contains a mutation which prevents spontaneous cell lysis, such as the Sam7 mutation and (v) the helper prophage contains a thermosensitive version of the master cl repressor, such as the c1857 version.

In a particular embodiment, the donor bacterial cell of the invention comprises the above-defined helper phage.

Treatment of Disease—Cosmetic Treatment

The vector used in the method of modulation of the invention may be administered as such, in a bacterial delivery vehicle or through a donor bacterial cell delivering said vector to the receiver bacterial cell. Said vector, bacterial delivery vehicle or donor bacterial cell may be more particularly administered in the form of a pharmaceutical or cosmetic composition comprising said vector, bacterial delivery vehicle or donor bacterial cell and a pharmaceutically acceptable carrier.

Generally, for pharmaceutical or cosmetic use, the vector, bacterial delivery vehicle or donor bacterial cell may be formulated as a pharmaceutical or cosmetic preparation or compositions comprising at least one vector, bacterial delivery vehicle or donor bacterial cell, and at least one pharmaceutically or cosmetically acceptable carrier, diluent or excipient, and optionally one or more further pharmaceutically or cosmetically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. In a particular embodiment, said composition is for oral administration. Such administration forms may be solid, semi-solid or liquid, depending on the manner and route of administration. For example, formulations for oral administration may be provided with an enteric coating that will allow the vector, bacterial delivery vehicle or donor bacterial cell, in the formulation to resist the gastric environment and pass into the intestines. More generally, vector formulations, bacterial delivery vehicle formulations or donor bacterial cell formulations for oral administration may be suitably formulated for delivery into any desired part of the gastrointestinal tract. In addition, suitable suppositories may be used for delivery into the gastrointestinal tract. Various pharmaceutically or cosmetically acceptable carriers, diluents and excipients useful in pharmaceutical or veterinary or cosmetic compositions are known to the skilled person The pharmaceutical or veterinary composition according to the invention may further comprise a pharmaceutically acceptable vehicle. The cosmetic composition of the invention may further comprise a cosmetically acceptable vehicle. A solid pharmaceutically or cosmetically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidone, low melting waxes and ion exchange resins.

The pharmaceutical or veterinary or cosmetic composition may be prepared as a sterile solid composition that may be suspended at the time of administration using sterile water, saline, or other appropriate sterile injectable medium. The pharmaceutical or veterinary or cosmetic compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The particles according to the disclosure can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The vectors, bacterial delivery vehicles or donor bacterial cells disclosed herein may be dissolved or suspended in a pharmaceutically or cosmetically acceptable liquid vehicle such as water, an organic solvent, a mixture of both or pharmaceutically acceptable oils or fats. The liquid vehicle can contain other suitable pharmaceutical or cosmetic additives such as solubilisers, emulsifiers, buffers, preservatives, sweeteners, flavouring agents, suspending agents, thickening agents, colours, viscosity regulators, stabilizers or osmoregulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically or cosmetically acceptable propellant.

In some embodiments, the invention encompasses pharmaceutical or veterinary or cosmetic composition formulated for delayed or gradual enteric release. In preferred embodiments, formulations or pharmaceutical or cosmetic preparations of the invention are formulated for delivery of the vector into the distal small bowel and/or the colon. The formulation can allow the vector to pass through stomach acid and pancreatic enzymes and bile, and reach undamaged to be viable in the distal small bowel and colon.

In some embodiments, the pharmaceutical or veterinary or cosmetic composition is micro-encapsulated, formed into tablets and/or placed into capsules, preferably enteric-coated capsules.

In some embodiments, the pharmaceutical or veterinary or cosmetic compositions are formulated for delayed or gradual enteric release, using cellulose acetate (CA) and polyethylene glycol (PEG). In some embodiments, the pharmaceutical or veterinary or cosmetic compositions are formulated for delayed or gradual enteric release using a hydroxypropylmethylcellulose (HPMC), a microcrystalline cellulose (MCC) and magnesium stearate. the pharmaceutical or veterinary compositions are formulated for delayed or gradual enteric release using e.g., a poly(meth)acrylate, e.g. a methacrylic acid copolymer B, a methyl methacrylate and/or a methacrylic acid ester, or a polyvinylpyrrolidone (PVP).

In some embodiments, the pharmaceutical or veterinary or cosmetic compositions are formulated for delayed or gradual enteric release using a release-retarding matrix material such as: an acrylic polymer, a cellulose, a wax, a fatty acid, shellac, zein, hydrogenated vegetable oil, hydrogenated castor oil, polyvinylpyrrolidone, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinyl acetates, polyvinylacetate copolymers or any combination thereof.

In some embodiments, the pharmaceutical or veterinary compositions are formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In some embodiments, the pharmaceutical or veterinary or cosmetic compositions are a powder that can be included into a tablet or a suppository. In alternative embodiments, a formulation or pharmaceutical or cosmetic preparation of the invention can be a 'powder for reconstitution' as a liquid to be drunk or otherwise administered.

In some embodiments, the pharmaceutical or veterinary or cosmetic compositions can be administered in a cream, gel, lotion, liquid, feed, or aerosol spray. In some embodiments, a bacteriophage is immobilized to a solid surface using any substance known in the art and any technology known in the art, for example, but not limited to immobilization of bacteriophages onto polymeric beads using technology as outlined in U.S. Pat. No. 7,482,115, which is incorporated herein by reference. Phages may be immobilized onto appropriately sized polymeric beads so that the coated beads may be added to aerosols, creams, gels or liquids. The size of the polymeric beads may be from about 0.1 μm to 500 μm, for example 50 μm to 100 μm. The coated polymeric beads may be incorporated into animal feed, including pelleted feed and feed in any other format, incorporated into any other edible devise used to present phage to the animals, added to water offered to animals in a bowl, presented to animals through water feeding systems. In some embodiments, the compositions are used for treatment of surface wounds and other surface infections using creams, gels, aerosol sprays and the like.

In some embodiments, the pharmaceutical or veterinary or cosmetic compositions can be administered by inhalation, in the form of a suppository or pessary, topically (e.g., in the form of a lotion, solution, cream, ointment or dusting powder), epi- or transdermally (e.g., by use of a skin patch), orally (e.g., as a tablet, which may contain excipients such as starch or lactose), as a capsule, ovule, elixirs, solutions, or suspensions (each optionally containing flavoring, coloring agents and/or excipients), or they can be injected parenterally (e.g., intravenously, intramuscularly or subcutaneously). For parenteral administration, the compositions may be used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. In a preferred embodiment, a bacteriophage and/or polypeptide of the present invention is administered topically, either as a single agent, or in combination with other antibiotic treatments, as described herein or known in the art.

In some embodiments, the pharmaceutical or veterinary or cosmetic compositions can also be dermally or transdermally administered. For topical application to the skin, the pharmaceutical or veterinary or cosmetic composition can be combined with one or a combination of carriers, which can include but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, and combinations thereof. A topical mode of delivery may include a smear, a spray, a bandage, a time-release patch, a liquid-absorbed wipe, and combinations thereof. The pharmaceutical or veterinary or cosmetic composition can be applied to a patch, wipe, bandage, etc., either directly or in a carrier(s). The patches, wipes, bandages, etc., may be damp or dry, wherein the phage and/or polypeptide (e.g., a lysin) is in a lyophilized form on the patch. The carriers of topical compositions may comprise semi-solid and gel-like vehicles that include a polymer thickener, water, preservatives, active surfactants, or emulsifiers, antioxidants, sun screens, and a solvent or mixed solvent system. U.S. Pat. No. 5,863,560 discloses a number of different carrier combinations that can aid in the exposure of skin to a medicament, and its contents are incorporated herein.

For intranasal or administration by inhalation, the pharmaceutical or veterinary or cosmetic composition is conveniently delivered in the form of a dry powder inhaler or an aerosol spray presentation from a pressurized container, pump, spray, or nebuliser with the use of a suitable propellant, e.g., dichlorodifluoromethane, trichlorofluoromethane, dichlorotetrafluoroethane, a hydrofluoroalkane such as 1,1,1,2-tetrafluoroethane or 1,1,1,2,3,3,3-heptafluoropropane, carbon dioxide, or other suitable gas. In the case of a pressurized aerosol, the dosage unit may be determined by providing a valve to deliver a metered amount. The pressurized container, pump, spray, or nebuliser may contain a solution or suspension of the active compound, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the bacteriophage and/or polypeptide of the invention and a suitable powder base such as lactose or starch.

For administration in the form of a suppository or pessary, the pharmaceutical or veterinary composition can be applied topically in the form of a gel, hydrogel, lotion, solution, cream, ointment, or dusting powder. Compositions of the invention may also be administered by the ocular route. For ophthalmic use, the compositions of the invention can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

Dosages and desired drug concentrations of the pharmaceutical and veterinary composition compositions of the present invention may vary depending on the particular use. The determination of the appropriate dosage or route of administration is within the skill of an ordinary physician. Animal experiments can provide reliable guidance for the determination of effective doses in human therapy.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

In a particular embodiment, the composition of the invention may further comprise at least one additional active ingredient, for instance a prebiotic and/or a probiotic and/or an antibiotic, and/or another antibacterial or antibiofilm agent, and/or any agent enhancing the targeting of the vector to a bacteria and/or the delivery of the vector into a bacteria.

As used herein, a "prebiotic" refers to an ingredient that allows specific changes, both in the composition and/or activity in the gastrointestinal microbiota that may confer benefits upon the host. A prebiotic can be a comestible food or beverage or ingredient thereof. A prebiotic may be a selectively fermented ingredient. Prebiotics may include complex carbohydrates, amino acids, peptides, minerals, or other essential nutritional components for the survival of the bacterial composition. Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-1), dietary fibers (e.g., soy fiber, sugarbeet fiber, pea fiber, corn bran, and oat fiber) and xylooligosaccharides.

As used herein, a "probiotic" refers to a dietary supplement based on living microbes which, when taken in adequate quantities, has a beneficial effect on the host organism by strengthening the intestinal ecosystem. Probiotic can comprise a non-pathogenic bacterial or fungal population, e.g., an immunomodulatory bacterial population, such as an anti-inflammatory bacterial population, with or without one or more prebiotics. They contain a sufficiently high number of living and active probiotic microorganisms that can exert a balancing action on gut flora by direct colonisation. It must be noted that, for the purposes of the present description, the term "probiotic" is taken to mean any biologically active form of probiotic, preferably including but not limited to lactobacilli, bifidobacteria, streptococci, enterococci, propionibacteria or saccharomycetes but even other microorganisms making up the normal gut flora, or also fragments of the bacterial wall or of the DNA of these microorganisms. These compositions are advantageous in being suitable for safe administration to humans and other mammalian subjects and are efficacious for the treatment, prevention, of a disease or disorder caused by bacteria such as bacterial infection. Probiotics include, but are not limited to lactobacilli, bifidobacteria, streptococci, enterococci, propionibacteria, saccharomycetes, lactobacilli, bifidobacteria, or proteobacteria.

In a particular embodiment, said probiotic is not affected by the vector of the invention. In a particular embodiment, when said vector is comprised in a bacterial delivery vehicle, said vehicle may bind to said probiotic but said probiotic is not affected by said vector. In an alternative embodiment, when said vector is comprised in a bacterial delivery vehicle, said vehicle does not bind to said probiotic and said probiotic is not affected by said vector.

In a particular embodiment, the effect of said vector induces or increases a synergy with the effect of the additional active ingredient. In a more particular embodiment, said vector enables said probiotic to engraft into said host organism.

The antibiotic can be selected from the group consisting of penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cephaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; fluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomicin, nalidixic acid, rifampin, derivatives and combination thereof.

In a particular embodiment, the modulating method of the invention is for treating and/or preventing a disease in said host subject.

In a particular embodiment, said disease is caused or mediated by bacteria.

The diseases or disorders caused or mediated by bacteria may be selected from the group consisting of skin chronic inflammation such as acne (acne vulgaris), progressive macular hypomelanosis, abdominal cramps, acute epiglottitis, arthritis, bacteraemia, bloody diarrhea, botulism, Brucellosis, brain abscess, cardiomyopathy, chancroid venereal disease, *Chlamydia*, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Windermere syndrome, Legionaire's disease, meningitis, mucopurulent conjunctivitis, multi-drug resistant bacterial infections, multi-drug resistant bacterial carriage, myocarditis, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough, Nonalcoholic Fatty Liver Disease (NAFLD), Nonalcoholic steatohepatitis (NASH).

The infection caused by bacteria may be selected from the group consisting of infections, preferably intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, postpartum infection, hospital acquired gastroenteritis, hospital acquired urinary tract infections, or a combination thereof. Preferably, the infection according to the invention is caused by a bacterium presenting an antibiotic resistance. In a particular embodiment, the infection is caused by a bacterium as listed above in the targeted bacteria.

The disclosure also concerns a pharmaceutical or veterinary composition of the invention for the treatment of a metabolic disorder including, for example, obesity, type 2 diabetes and nonalcoholic fatty liver disease. Indeed, emerging evidence indicates that these disorders are characterized by alterations in the intestinal microbiota composition and its metabolites (Tilg et al., Nature Reviews Immunology, volume 20, pages 40-54, 2020). The pharmaceutical or veterinary composition may thus be used to deliver in some intestinal bacteria a nucleic acid of interest which can alter the intestinal microbiota composition or its metabolites (e.g. by inducing expression, overexpression or secretion of some molecules by said bacteria, for example molecules having a beneficial role on metabolic inflammation). The disclosure also concerns the use of a pharmaceutical or veterinary composition of the invention for the manufacture of a medicament for the treatment of a metabolic disorder including, for example, obesity, type 2 diabetes and nonalcoholic fatty liver disease. It also relates to a method for treating a metabolic disorder including, for example, obesity, type 2 diabetes and nonalcoholic fatty liver disease, comprising administering to a subject having a metabolic disorder in need of treatment the provided pharmaceutical or veterinary composition, in particular a therapeutically effective amount of the provided pharmaceutical or veterinary composition.

In a particular embodiment, the invention concerns a pharmaceutical or veterinary composition for use in the treatment of pathologies involving bacteria of the human microbiome, such as inflammatory and auto-immune diseases, cancers, infections or brain disorders. Indeed, some bacteria of the microbiome, without triggering any infection, can secrete molecules that will induce and/or enhance inflammatory or auto-immune diseases or cancer development. More specifically, the present invention relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

In an alternative embodiment, said disease is not caused by bacteria.

In certain embodiments, the disease to be treated is cancer or a proliferative disorder, including but not limited to, breast cancer (e.g., triple negative breast cancer, ER+ breast cancer, or ER− breast cancer), basal cell carcinoma, skin cancer, lung cancer, small cell lung cancer, non-small cell lung cancer, brain cancer, medulloblastoma, glioma (including glioblastoma, oligodendroglioma, astrocytoma, ependymoma), neuroblastoma, colorectal cancer, ovarian cancer, liver cancer, pancreatic cancer (e.g., carcinoma, angiosarcoma, adenosarcoma), gastric cancer, gastroesophageal junction cancer, prostate cancer, cervical cancer, bladder cancer, head and neck cancer, lymphoma (e.g., mantle cell lymphoma, diffuse large B-cell lymphoma), solid tumors that cannot be removed by surgery, locally advanced solid tumors, metastatic solid tumors, leukemia (e.g., acute myeloid leukemia (AML), acute lymphoblastic leukemia (ALL), or chronic myeloid leukemia (CML)), or recurrent or refractory tumors.

In one embodiment, the diseases to be treated include, but are not limited to, inflammatory or allergic diseases, including systemic anaphylaxis and hypersensitivity disorders, atopic dermatitis, urticaria, drug allergies, insect sting allergies, food allergies (including celiac disease and the like), and mastocytosis; inflammatory bowel diseases, including Crohn's disease, ulcerative colitis, ileitis, and enteritis; vasculitis, and Behcet's syndrome; psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; asthma and respiratory allergic diseases, including allergic asthma, exercise induced asthma, allergic rhinitis, otitis media, allergic conjunctivitis, hypersensitivity lung diseases, and chronic obstructive pulmonary disease; autoimmune diseases, including arthritis (including rheumatoid and psoriatic), systemic lupus erythematosus, type I diabetes, myasthenia gravis, multiple sclerosis, Graves' disease, and glomerulonephritis; graft rejection (including allograft rejection and graft-v-host disease), e.g., skin graft rejection, solid organ transplant rejection, bone marrow transplant rejection; fever; cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; cerebrovascular disorders, including traumatic brain injury, stroke, ischemic reperfusion injury and aneurysm; fibrosis, connective tissue disease, and sarcoidosis, genital and reproductive conditions, including erectile dysfunction; gastrointestinal disorders, including gastritis, ulcers, nausea, pancreatitis, and vomiting; neurologic disorders, including Alzheimer's disease; sleep disorders, including insomnia, narcolepsy, sleep apnea syndrome, and Pickwick Syndrome; pain; renal disorders; ocular disorders, including glaucoma; and non-bacterial infectious diseases, including HIV.

In some aspects, the disease to be treated may be an autoimmune disease such as autoimmune hemolytic anemia, autoimmune neonatal thrombocytopenia, autoimmune neutropenia, autoimmunocytopenia, antiphospholipid syndrome, dermatitis, gluten-sensitive enteropathy, allergic encephalomyelitis, myocarditis, relapsing polychondritis, rheumatic heart disease, glomerulonephritis, Multiple Sclerosis, Neuritis, Uveitis Ophthalmia, Polyendo-crinopathies, Purpura, Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitis, autoimmune inflammatory eye, autoimmune thyroiditis, hypothyroidism, systemic lupus erythematosus, discoid lupus, Goodpasture's syndrome, Pemphigus, Graves' Disease, Myasthenia Gravis, and insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis, bullous pemphigoid, Sjogren's syndrome, diabetes mellitus, adrenergic drug resistance with asthma or cystic fibrosis, chronic active hepatitis, primary biliary cirrhosis, endocrine gland failure, vitiligo, vasculitis, post-MI, cardiotomy syndrome, urticaria, atopic dermatitis, asthma, inflammatory myopathies, an inflammatory disorder, a granulomatous disorder, an atrophic disorder, or an alloimmune disease.

The subject to be treated may have been diagnosed with, or may be at risk of developing an infection, a disorder and/or a disease preferably due to a bacterium. Diagnostic method of such infection, disorder and/or disease are well known by the man skilled in the art.

In a particular embodiment, the infection, disorder and/or disease presents a resistance to treatment, preferably the infection, disorder or disease presents an antibiotic resistance.

In a particular embodiment, the subject has never received any treatment prior to the administration of the vectors according to the invention, particularly a vector packaged into a delivery vehicle according to the invention, preferably a packaged plasmid or phagemid into a bacterial virus particle according to the invention, or of a pharmaceutical or veterinary composition according to the invention.

In a particular embodiment, the subject has already received at least one line of treatment, preferably several lines of treatment, prior to the administration of the vectors according to the invention, particularly a vector packaged into a delivery vehicle according to the invention, preferably a packaged plasmid or phagemid into a bacterial virus particle according to the invention, or of a pharmaceutical or veterinary composition according to the invention.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with vectors according to the invention, particularly a vector packaged into a delivery vehicle according to the invention, preferably a packaged plasmid or phagemid into a bacterial virus particle according to the invention, or with a pharmaceutical or veterinary composition according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of vectors according to the invention, particularly of a vector packaged into a delivery vehicle according to the invention, preferably of a packaged plasmid or phagemid into a bacterial virus particle according to the invention, or of a pharmaceutical or veterinary composition according to the invention can be adjusted by the man skilled in the art according to the type and severity of the infection (e.g. depending on the bacteria species involved in the disease, disorder and/or infection and its localization in the patient's or subject's body), and to the patient or subject, in particular its age, weight, sex, and general physical condition.

Particularly, the amount of vectors according to the invention, particularly a vector packaged into a delivery vehicle according to the invention, preferably a packaged plasmid or phagemid into a bacterial virus particle according to the invention, or of a pharmaceutical or veterinary composition according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of vectors, particularly a vector packaged into a delivery vehicle according to the invention, preferably a plasmid or phagemid packaged into a bacterial virus particle according to the invention, for each administration is comprised between $10^4$ and $10^{15}$ delivery vehicles.

In another particular embodiment, the modulating method of the invention is for the cosmetic treatment of said host subject.

Plant Treatment and Other Applications

In another particular embodiment, the host organism is a plant, and the modulating method of the invention is for the agronomical, prophylactic or phytotherapeutic treatment of said host plant.

In a particular embodiment, said modulating method is for improving the growth of said host plants, for preventing a disease or for treating diseases affecting said host plants.

The present invention also concerns a method for ex vivo modulating a microbiome from an environment by collecting targeted receiver bacterial cell from said environment and by delivering a nucleic acid of interest into said targeted receiver bacterial cell of said microbiome, said nucleic acid of interest producing a given effect, as disclosed above, on said targeted receiver bacterial cell, wherein said method comprises contacting a nucleic acid vector comprising said nucleic acid of interest with said microbiome, wherein said vector further comprises a conditional origin of replication which is inactive in the targeted receiver bacterial cell but is active in a donor bacterial cell, and said vector is devoid of antibiotic resistance marker, thereby delivering said nucleic acid of interest into the targeted receiver bacterial cell, and wherein, once delivered into said targeted receiver bacterial cell, said nucleic acid of interest produces said given effect on said targeted receiver bacterial cell while said vector is not replicated in said targeted receiver bacterial cell.

By "environment" is meant herein all the elements which surround a species and among which some directly or indirectly contribute to the subsistence of said species. In a particular embodiment, said environment is not an animal. In an alternative embodiment, said environment is an animal, in particular a human.

In a particular embodiment, said environment can be any medium wherein said microbiome lives, such as a solid or semi-solid surface or a liquid medium, such as water, in particular waste water.

In a particular embodiment, said ex vivo method is for protecting a surface against biofouling. In another particular embodiment, said ex vivo method is for decontaminating water.

The present invention further concerns the following embodiments.

1. A method for in vivo modulating the microbiome of a host organism by delivering a nucleic acid of interest into a targeted receiver bacterial cell of said microbiome, said nucleic acid of interest producing a given effect on said targeted receiver bacterial cell,
    wherein said method comprises administering, in said organism, a nucleic acid vector comprising said nucleic acid of interest,
        wherein said vector further comprises a conditional origin of replication which is inactive in the targeted receiver bacterial cell but is active in a donor bacterial cell, and said vector is devoid of antibiotic resistance marker,
    thereby delivering said nucleic acid of interest into the targeted receiver bacterial cell, and
    wherein, once delivered into said targeted receiver bacterial cell, said nucleic acid of interest produces said given effect on said targeted receiver bacterial cell while said vector is not replicated in said targeted receiver bacterial cell.
2. The method according to embodiment 1, wherein said nucleic acid of interest is expressed in said targeted receiver bacterial, thereby producing said given effect.
3. The method according to embodiment 1 or 2, wherein said modulation of the microbiome is a modulation of the microbiome function or of the microbiome composition.
4. The method according to any one of embodiments 1 to 3, wherein said given effect is selected from the group consisting of killing the receiver bacterial cell, making the receiver bacterial cell stop producing a given molecule and making the receiver bacterial cell produce a molecule of interest.
5. The method according to any one of embodiments 1 to 4, wherein said given effect is making the receiver bacterial cell produce a molecule of interest and said molecule of interest is a host modulatory molecule.
6. The method according to embodiment 5, wherein said host modulatory molecule is selected from the group consisting of non-coding nucleic acids, coding nucleic acids, proteins, lipids, sugars, LPS, metabolites and small molecules.
7. The method according to any one of embodiments 5 to 6, wherein said host modulatory molecule is selected from the group consisting of host endogenous molecules, host exogenous molecules expressed naturally by other organisms, and synthetic compounds.
8. The method according to any one of embodiments 5 to 7, wherein said host modulatory molecule is selected from the group consisting of secreted molecules, intracellular molecules and membrane-displayed molecules.
9. The method according to any one of embodiments 5 to 8, wherein said molecule of interest is encoded by a nucleic acid selected from the group consisting of a gene encoding said host modulatory molecule, several genes encoding a protein complex that is the host modulatory molecule, a gene or group of genes encoding enzyme(s) of a metabolic pathway leading to the production of the host modulatory molecule, a coding nucleic acid which is the host modulatory molecule, and a non-coding nucleic acid which is the host modulatory molecule.
10. The method according to any one of embodiments 1 to 4, wherein said given effect is making the receiver bacterial cell stop producing a given molecule and wherein said given molecule is selected from the group consisting of a toxin, a toxic factor, a virulence protein, a virulence factor, a protein encoded by an antibiotic resistance gene, a protein encoded by a remodeling gene or by a modulatory gene.
11. The method according to embodiment 10, wherein said nucleic acid of interest is a gene or group of genes encoding one or more exogenous enzyme(s) which result(s) in a genetic modification.
12. The method according to embodiment 11, wherein said nucleic acid of interest is gene encoding a base-editor or a prime-editor.
13. The method according to any one of embodiments 1 to 4, wherein said given effect is killing the receiver bacterial cell and wherein said nucleic acid of interest is a gene encoding a nuclease.
14. The method according to any one of embodiments 1 to 13, wherein the conditional origin of replication is an origin of replication, the replication of which depends upon the presence of a given protein, peptid, nucleic acid, RNA, molecule or any combination thereof.
15. The method according to embodiment 14, wherein said conditional origin of replication is active in said donor bacterial cell because said donor bacterial cell expresses said given protein, peptid, nucleic acid, RNA, molecule or any combination thereof.
16. The method according to embodiment 15, wherein said protein, peptid, RNA, molecule or any combination thereof is expressed in trans in said donor bacterial cell.
17. The method according to embodiment 14 or 15, wherein said conditional origin of replication is an origin of replication derived from phage-inducible chromosomal islands (PICIs).
18. The method according to embodiment 17, wherein said conditional origin of replication is active in said donor bacterial cell because said donor bacterial cell expresses a rep protein, in particular a primase-helicase.
19. The method according to embodiment 17 or 18, wherein said conditional origin of replication is derived from the origin of replication from the PICI of the *Escherichia coli* strain CFT073.
20. The method according to any one of embodiments 1 to 19, wherein said vector does not comprise any restriction site of restriction enzymes which are frequently encoded in said targeted receiver bacterial cell.

21. The method according to any one of embodiments 1 to 20, for treating a disease in said host subject.

22. The method according to any one of embodiments 1 to 20, for a cosmetic treatment of said host subject.

23. A nucleic acid vector for use in in vivo delivery of a nucleic acid of interest into a targeted receiver bacterial cell, said nucleic acid of interest producing a given effect on said targeted receiver bacterial cell,
wherein said vector comprises:
said nucleic acid of interest, and
a conditional origin of replication which is inactive in the targeted receiver bacterial cell but is active in a donor bacterial cell, and
wherein said vector is devoid of antibiotic resistance marker.

24. The nucleic acid vector according to embodiment 23, wherein said conditional origin of replication is the primase on from the PICI of the *Escherichia coli* strain CFT073 or a derivative thereof.

25. The nucleic acid vector according to embodiment 23, wherein said conditional origin of replication comprises or consists of the sequence SEQ ID NO: 6 or SEQ ID NO: 7.

26. A bacterial delivery vehicle for use in in vivo delivery of a nucleic acid of interest into a targeted receiver bacterial cell, wherein said bacterial delivery vehicle comprises the vector according to any one of embodiments 23 to 25.

27. A donor cell line comprising the vector according to any one of embodiments 23 to 25 or producing the bacterial delivery vehicle according to embodiment 26, wherein said donor cell line stably comprises the vector according to any one of embodiments 23 to 25 and is able to replicate said vector.

28. The donor cell line according to embodiment 27, wherein the conditional origin of replication of said vector is an origin of replication, the replication of which depends upon the presence of a given protein, peptid, nucleic acid, RNA, molecule or any combination thereof, and said donor cell line expresses said protein, peptid, nucleic acid, RNA, molecule or any combination thereof.

29. The donor cell line according to embodiment 26, wherein said protein, peptid, nucleic acid, RNA, molecule or any combination thereof is expressed in trans.

30. A method for ex vivo modulating a microbiome from an environment by collecting targeted receiver bacterial cell from said environment and by delivering a nucleic acid of interest into a targeted receiver bacterial cell of said microbiome, said nucleic acid of interest producing a given effect on said targeted receiver bacterial cell,
wherein said method comprises contacting a nucleic acid vector comprising said nucleic acid of interest with said microbiome,
wherein said vector further comprises a conditional origin of replication which is inactive in the targeted receiver bacterial cell but is active in a donor bacterial cell, and said vector is devoid of antibiotic resistance marker,
thereby delivering said nucleic acid of interest into the targeted receiver bacterial cell, and
wherein, once delivered into said targeted receiver bacterial cell, said nucleic acid of interest produces said given effect on said targeted receiver bacterial cell while said vector is not replicated in said targeted receiver bacterial cell.

Unless defined otherwise, all technical and scientific terms used herein have the same meaning as commonly understood by one of ordinary skill in the art to which this invention belongs.

All publications mentioned herein are incorporated herein by reference. It is understood that the present disclosure supersedes any disclosure of an incorporated publication to the extent there is a contradiction.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

The present invention will be further illustrated by the figures and examples below.

BRIEF DESCRIPTION OF THE FIGURES

FIG. 1A-1B: BLAST analysis of the PICI-CFT073 origin in *Escherichia coli*.

FIG. 2A-2B: BLAST analysis of modified p15a origin of replication of sequence SEQ ID NO: 4 in *Escherichia coli*.

FIG. 3A-3B: BLAST analysis of the PICI-CFT073 origin in the domain Bacteria.

FIG. 4A-4B: BLAST analysis of the modified p15a origin in the domain Bacteria.

Figure 5:
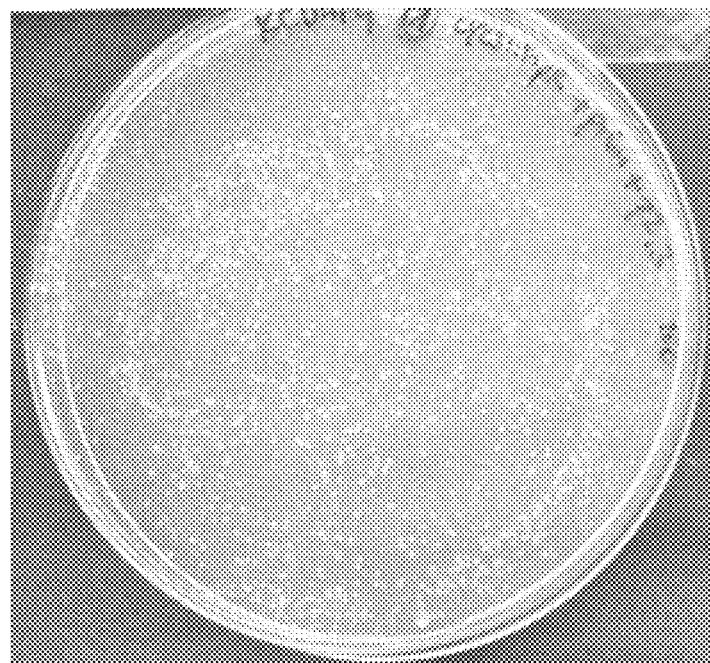
FIG. 5: Transformation of a 2.3 kb payload containing the primase-origin of replication (p1319) in a production strain harboring an inducible primase RBS library in trans.

| BRIEF DESCRIPTION OF THE SEQUENCES | | |
|---|---|---|
| SEQ ID NO: | Description | Type |
| 1 | insulin B9-25 epitope | Protein |
| 2 | T cell (β2GPI) epitope | Protein |
| 3 | B cell epitope | Protein |
| 4 | primase ori from the PICI of the *E. coli* strain CFT073 | DNA |
| 5 | Restriction site | DNA |
| 6 | Primase ori deltaGAAABCC | DNA |
| 7 | Primase ori devoid of restriction sites | DNA |
| 8 | PICI primase-helicase | Protein |
| 9 | PICI primase-helicase | DNA |
| 10 | payload p1392 plasmid | DNA |
| 11 | payload p1900 plasmid | DNA |
| 12 | chimeric STF (STF-V10-[Helix]) | Protein |
| 13 | chimeric STF (STF-V10-[Helix]) | DNA |
| 14 | chimeric gpJ (1A2) | Protein |
| 15 | chimeric gpJ (1A2) | DNA |
| 16 | p2.3 pri-ori p1319 | DNA |
| 17 | p2.8 p15a, p1220 | DNA |
| 18 | primase RBS 1 | DNA |
| 19 | primase RBS 2 | DNA |
| 20 | primase RBS 3 | DNA |
| 21 | primase RBS 4 | DNA |
| 22 | primase RBS 5 | DNA |
| 23 | primase RBS 6 | DNA |
| 24 | primase RBS 7 | DNA |
| 25 | plasmid lacz6 pri-ori, p1322 | DNA |
| 26 | primase RBS 11 | DNA |
| 27 | plasmid LacZ6 p15a, p780 | DNA |
| 28 | plasmid LacZ6 pri-ori deltaGAAABCC, p1326 | DNA |
| 29 | plasmid 4stx pri-ori deltagaaabcc, p1327 | DNA |
| 30 | β-lactamase gene | DNA |

EXAMPLES

Packaged phagemids are being used to deliver a DNA payload to target bacteria with high efficiency. Features required for phagemid packaging are the presence of a packaging site and an origin of replication that is functional in the producer cell line.

The use of a constitutive origin of replication to produce packaged phagemids has several advantages, notably:
It can be stably maintained in production strains, simplifying the engineering, production and manufacturing processes,
Some constitutive ORIs compatible with lambda-based packaging, lead to sufficiently high titers (>$10^{10}$/mL) required for microbiota-related applications (killing, delivery of therapeutic payloads, etc),
Since the payload will replicate in the target strain once injected, the effect of the expression of the gene of interest may be sustained long enough to have the desired outcome, for instance the killing efficiency may be higher when delivering a CRISPR-cas system targeted towards a chromosomal sequence, since it will be more difficult for the target strains to get rid of the payload by division: the residence time is increased.
Since phages have a precise tropism towards the same or closely related species in which they are produced, the packaged phagemids derived from this phage, once their payloads delivered in the target bacteria, will keep replicating, unless the phage has been engineered to infect/inject in a new group of bacteria.

However, having a phagemid harbouring a constitutive origin of replication may pose some risks when used in a clinical, industrial, or non-contained setup:
Since the payload is replicative, some events of injection will cause the plasmid to spread.
Moreover, when the payload is based on a common origin of replication present in many Enterobacteria (for example, a ColE-type origin), the risk of recombination with already-existing plasmids in target bacterial strains may be high. For regulatory purposes, this poses a problem since the transduced cells are considered as GMOs and are then replicative GMOs, which poses a containment risk that has to be evaluated accordingly.
For all these reasons, the inventors aimed to develop a conditional system of replication that encompasses all the advantages mentioned above while reducing the spread and recombination risks. Such a system needs to have the following features:
Replication of the payload must occur only in the production strain, the payload must be easy to maintain and be stable,
The system must allow for sufficiently high titers to be obtained (>$10^{10}$/mL) to be relevant in an industrial setting,
The system must be amenable to sequence changes in case restriction sites need to be removed,
The system needs to be sufficiently rare in potential target strains as to reduce the risks of spread and recombination,
Finally, the system must allow for the gene of interest to be expressed and create the desired outcome (for instance killing of target strains at similar MOIs as when using replicative payloads).
In the following examples, the present inventors developed PICI-based conditional origins of replication.
First, they verified how common the origin region is in bacterial genomes, to assess the possibility of undesired recombination or payload spread events.
Second, they developed a system with the primase and ori in trans (ori on the phagemid
primase gene in the chromosome or on another plasmid carried by the bacteria) to assess if replication is truly conditional and dependant on the presence of the primase and to verify the titers obtained when such a system is used to package DNA payload.
Third, they tested in vitro killing of *E. coli* and compared it to the current generation of replicative payloads.
Finally, they assessed if the primase-origin was amenable to removal of undesired restriction sites.
In the following examples,
The inventors show for the first time that phagemids can be packaged at high titers with a conditional ORI,
The inventors show for the first time that phagemids can be packaged at high titers with a conditional ORI with ori and protein required for replication in trans,
The inventors show the additional advantage of using a ORI system that can be found in PICI genomes as opposed to other systems based on plasmid derived ORI (from a bacterial origin), which significantly limits the risk of spread. Furthermore, even if the ORI system is actually present in the transduced bacteria, meaning that a natural PICI harboring the same ORI system is found in the bacteria, it has to be active (in a lytic cycle) for the introduced phagemid to be replicated, since the primase gene in a PICI is inactive unless found in the induced (lytic) state. This is totally different for a bacterial ORI, since it would mean that it would be active naturally and constitutively.

Example 1

Blasting the Ori Region to Assess Frequency in *E. coli* and Other Bacteria

The 282 bp region right after the stop codon of the PICI-CFT073 primase (SEQ ID NO: 4) was used to BLAST against all sequenced *Escherichia coli* genomes, filtering to give up to 20,000 hits.

Figure 1A:
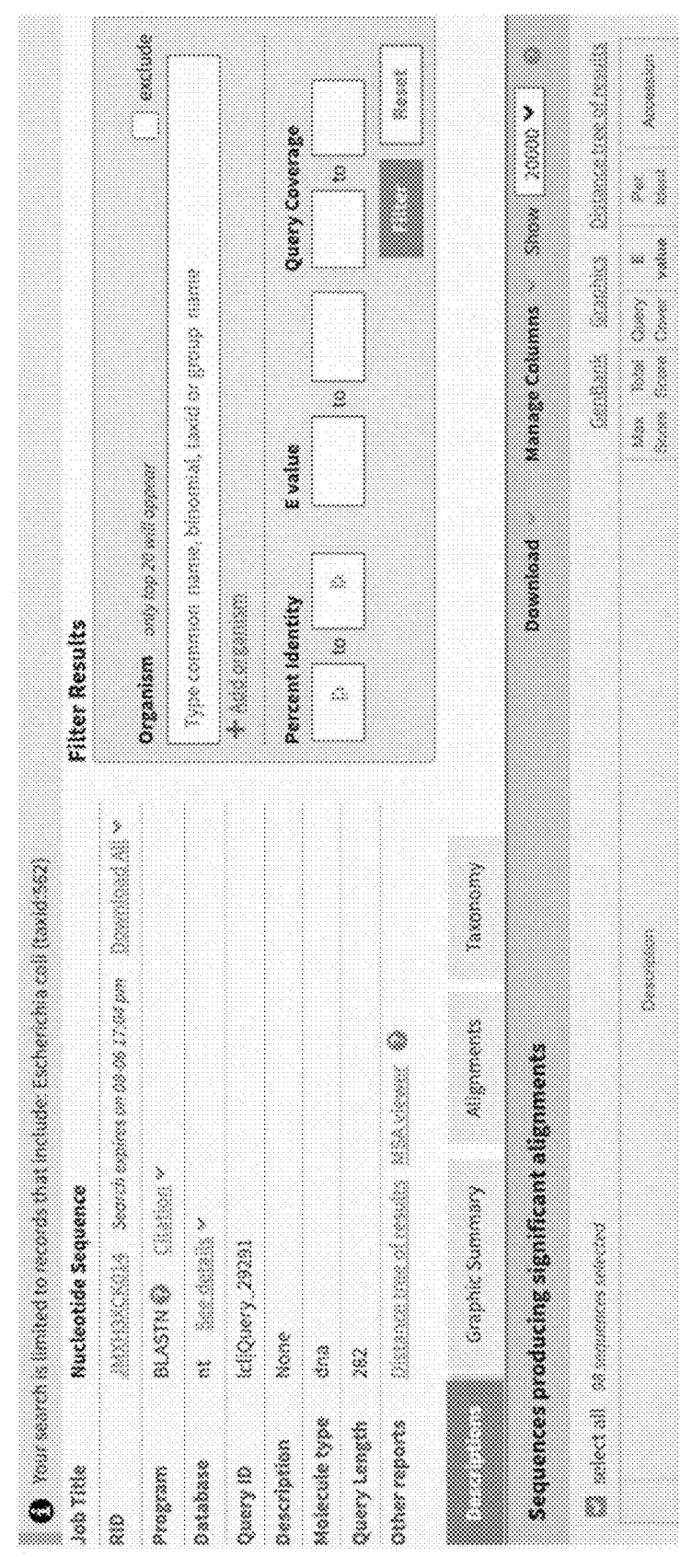
Figure 1B:
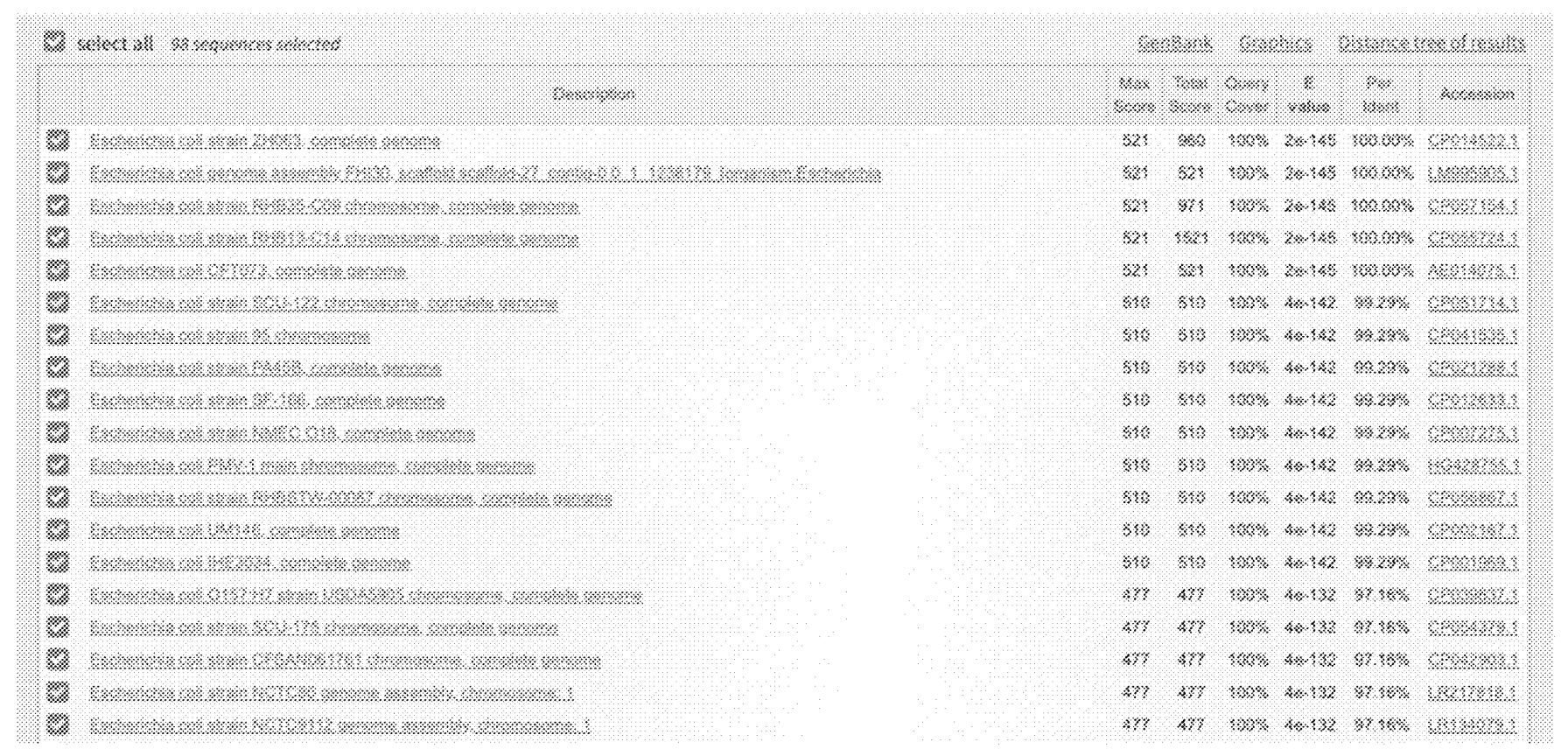

As shown in FIG. 1, out of all sequenced *E. coli* genomes, there are only 98 hits, which means that this specific primase-ori is very rare and hence, will drastically reduce the risk of recombination and replication in target and non-target strains.

It also needs to be noted that, under normal circumstances, the primase of the PICI is inactive, meaning that even if injection occurs in a strain containing this specific PICI, it will not replicate unless the cell is under a phage-induction state, which further reduces the chances of the introduced payload replicating when not desired.

Figure 2A:
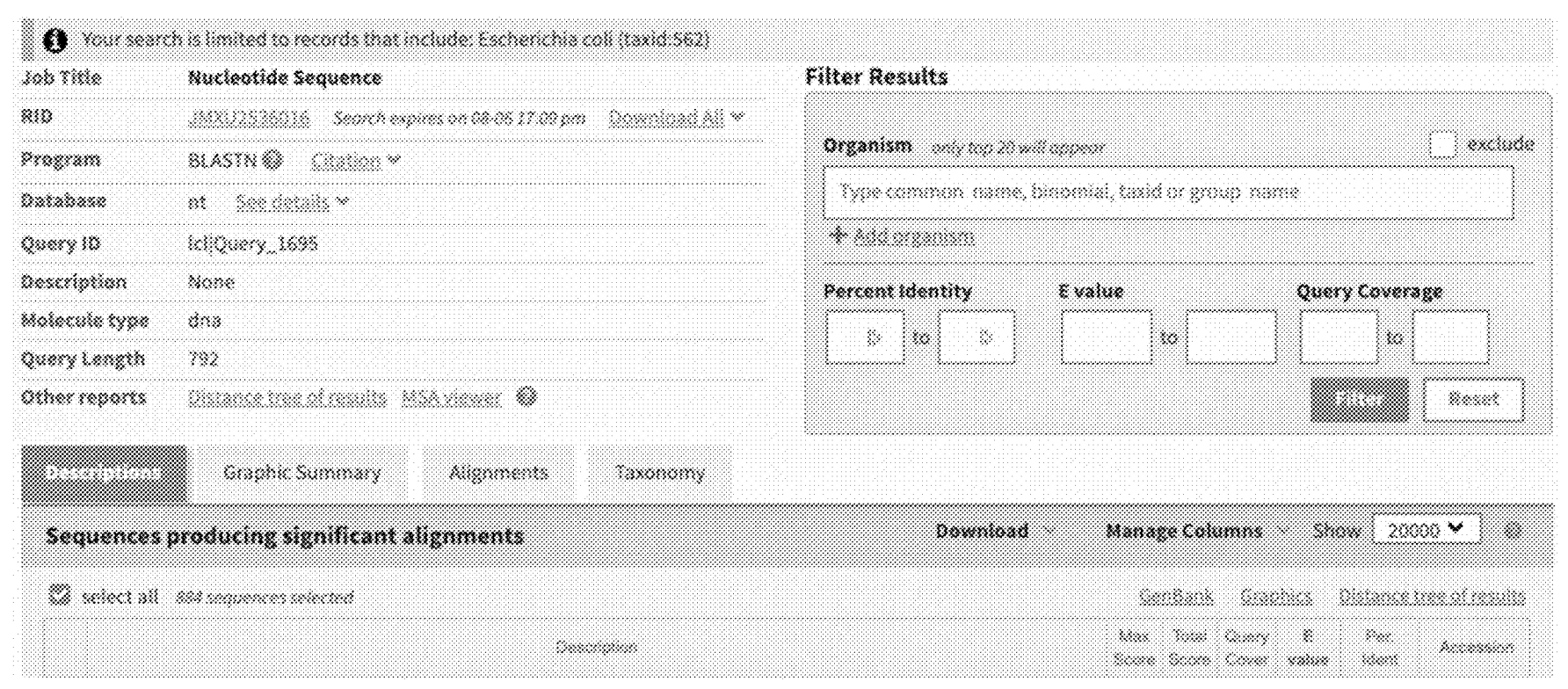

As a comparison, performing a BLAST analysis with a non-conditional modified p15a-based origin of replication returns the hits shown in FIG. 2.

884 sequences were found. It also needs to be noted that when sequencing strains, plasmids may be left out of the assembly if they are small (for example, the pOSAK found in STEC O157 strains), so the number of hits may be higher.

Figure 3A:
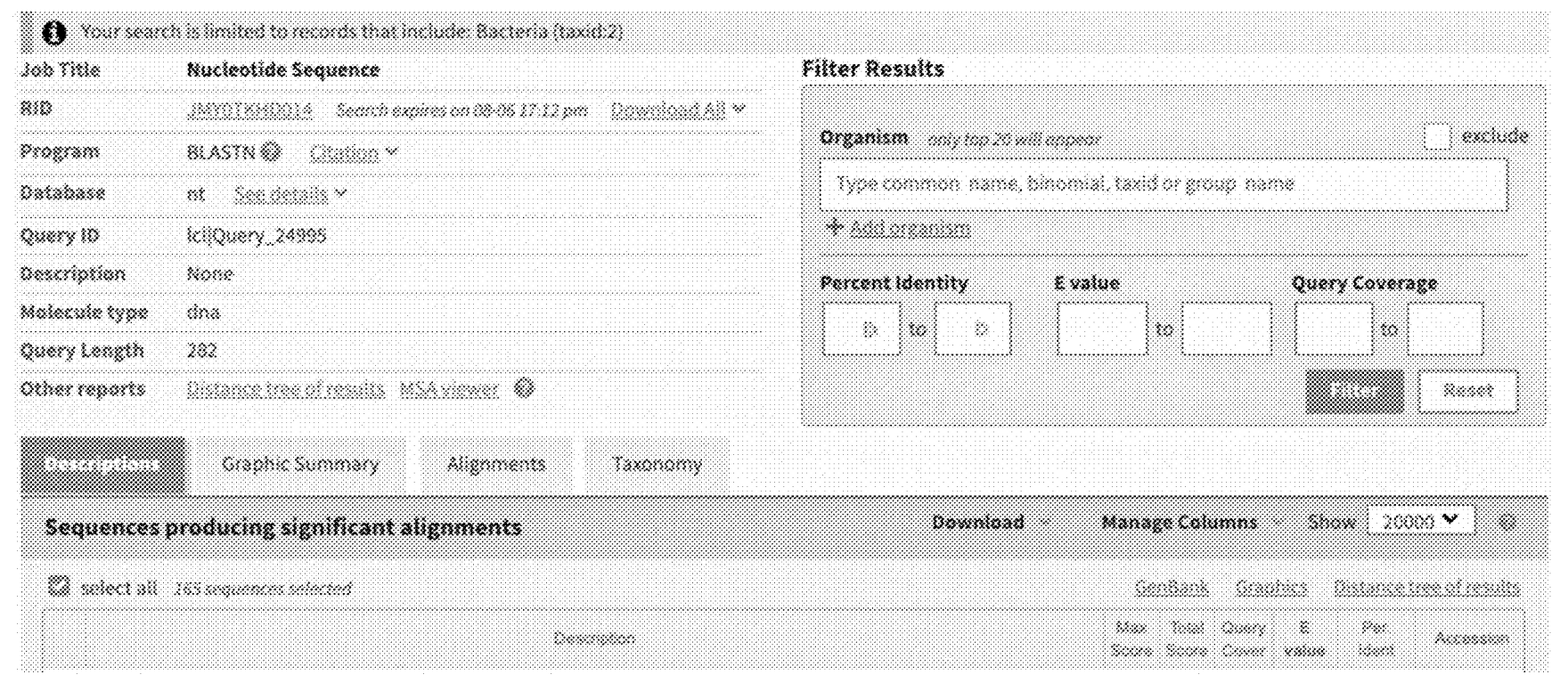
Figure 4A:
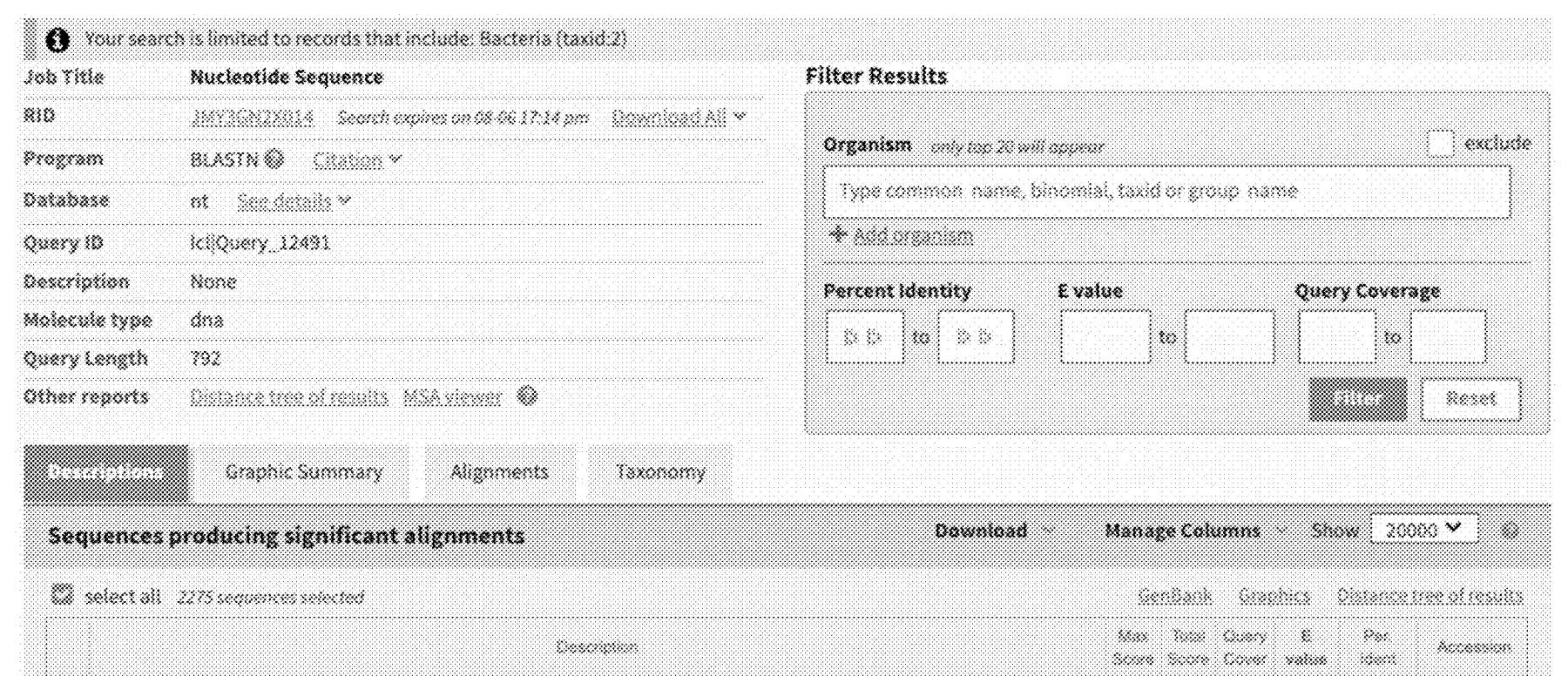
Figure 4B:
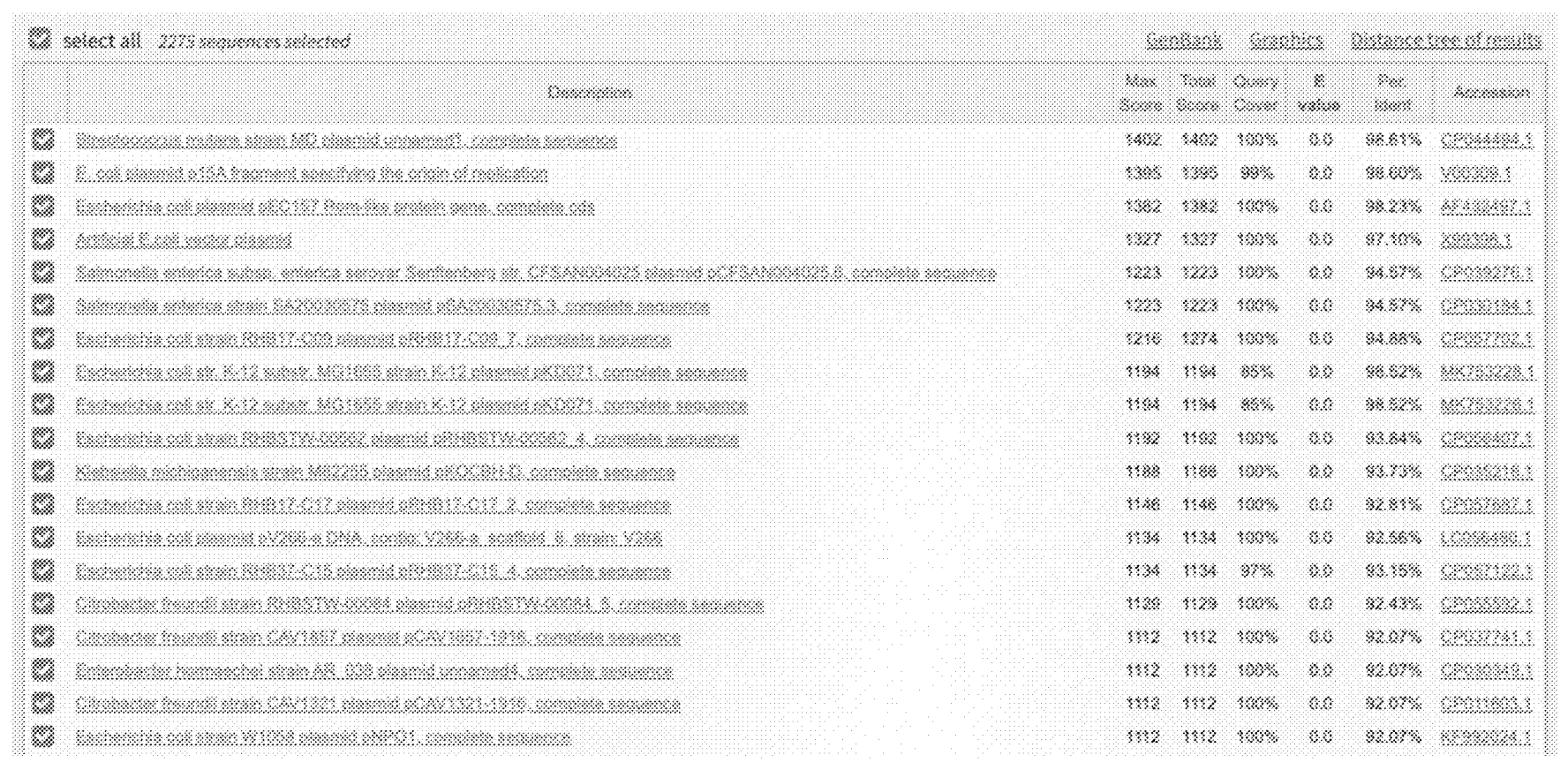

Next, the inventors performed the same search but this time using the Domain Bacteria to assess the presence of the PICI-ori in other non-*E. coli* species: 165 hits were found for the PICI origin while more than 2000 hits were found for the p15a-based origin (see FIGS. 3 and 4).

In conclusion the inventors showed that the primase-ori was a good candidate to reduce the risk of recombination and undesired replication in target and non-target bacteria since its occurrence, based on BLAST analyses, is 10 to 20 fold lower than a p15a-based origin; and for effective replication, the cell where the payload is injected will need to be undergoing active phage production for the PICI primase to be present.

Example 2

Developing a System with Primase-Ori in Trans Compatible with Phagemids Packaging Next, the inventors sought to develop a system in which the payload contains the 282-bp primase origin and the primase protein is supplied in trans (SEQ ID NO: 8 and SEQ ID NO: 9). To simplify the engineering process, the PICI primase gene was extracted from the genome of *E. coli* CFT073, cloned into a plasmid under the control of an inducible system and an RBS (ribosome-binding site) library generated. This series of plasmids were cloned in the lambda production strain s1965. Next, the inventors constructed a small payload harboring the primase-ori instead of the p15a-based origin of replication to yield the 2.3 kb payload p1319 (SEQ ID NO: 16). Since this plasmid is, in principle, non-replicative, competent cells of s1965 harboring the RBS library of inducible primase constructs were made, the p1319 plasmid transformed in them and plated in LB agar+kanamycin and chloramphenicol in the presence of the inducer DAPG (to induce the expression of the primase in trans). Next day, the inventors observed that the plates contained hundreds of colonies, suggesting that the primase-origin system in trans works (FIG. 5).

Several clones were sequenced to verify that the p1319 plasmid contained no p15a-based origin and that they also contained an intact primase gene with an RBS coming from the library.

After that, 7 of these clones were grown overnight and lambda productions were carried out in the presence of kanamycin, chloramphenicol and DAPG. As a control, the inventors included the original 2.8 kb plasmid containing a derivative of the p15a origin of replication to compare titers (p1220, SEQ ID NO: 17)

To verify the sequence of the RBS variants obtained, the plasmid encoding the inducible primase in the 7 clones tested was miniprepped and sequenced (SEQ ID NO: 18 to 24). They were also transformed into MG1655 cells (s003): these strains were used to verify the titers obtained, since the payloads should not be replicative in the absence of the primase protein supplied in trans.

Figure 6:
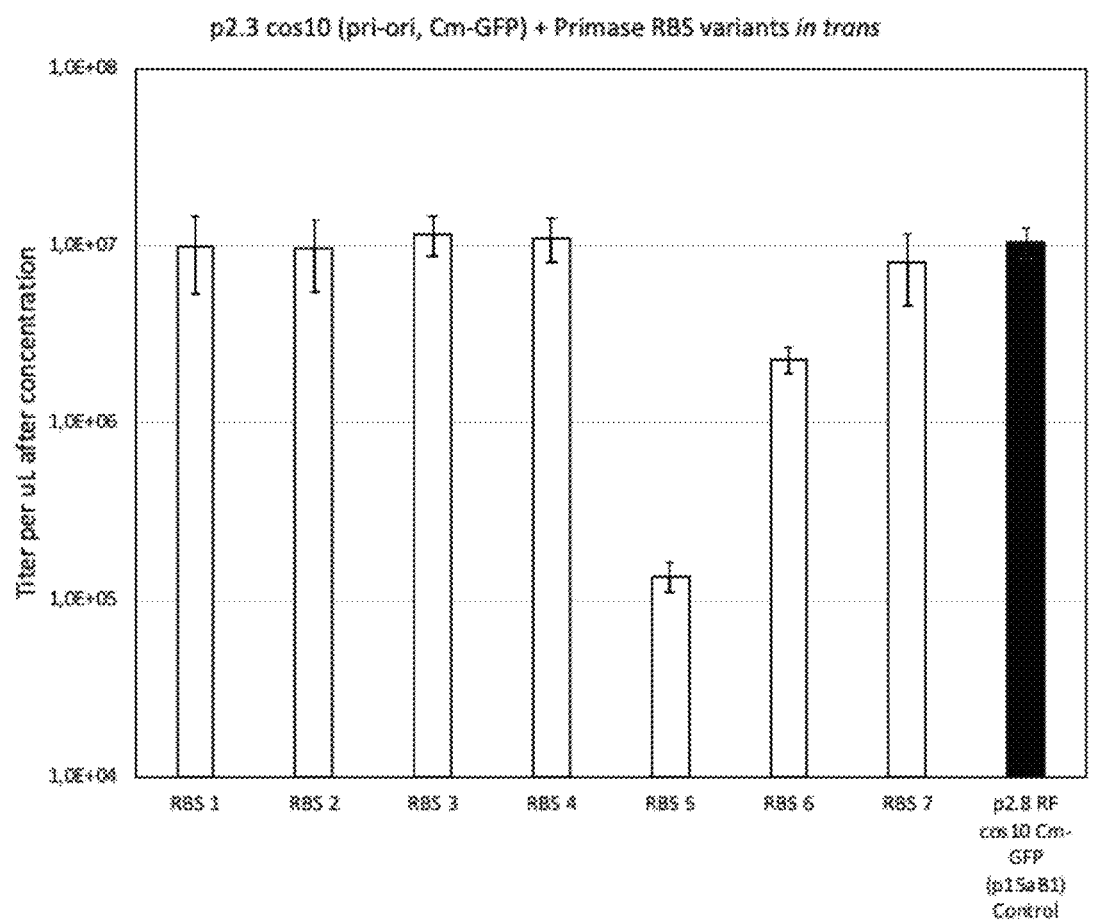
FIG. 6: Comparison of packaged phagemids titers obtained with a plasmid containing the primase-ori in production strains (p1319) tested against 7 different primase RBS. Right column, in black, control plasmid with a p15a-derived origin of replication (p1220). Titers shown are after a 10× concentration.

As can be seen on FIG. 6, the titers of 5 out of 7 primase-containing samples, as measured in MG1655 containing the primase plasmid in trans, were the same as those of a packaged phagemid carrying the original modified p15a origin.

Figure 7:
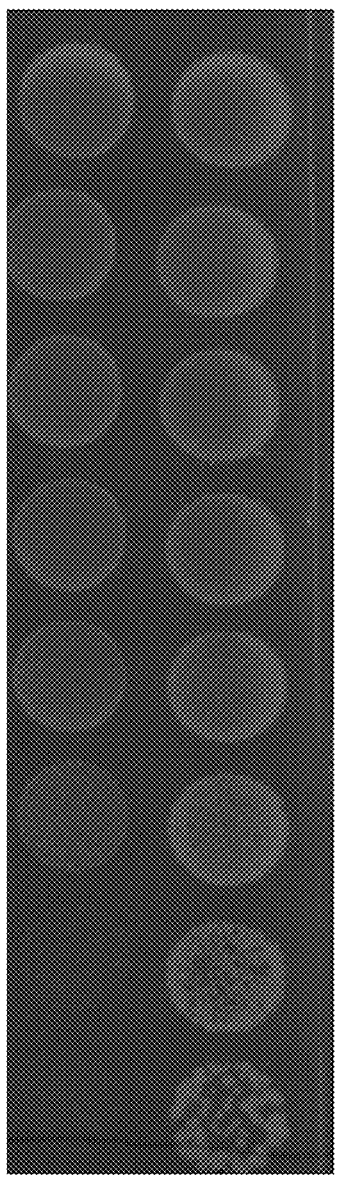
FIG. 7: Comparison of cells transduced with a primase-ori plasmid (top row, p1319) and a p15a-based packaged phagemids (p1220) on LB agar plus 25 µg/mL chloramphenicol. RBS 3 is SEQ ID NO: 20.

Finally, the inventors tested if the primase-ori containing payloads could replicate in MG1655 strains without the primase plasmid in trans. To do this, serial 5X dilutions of the primase-ori containing plasmids coming from the production strains with different primase RBS, plus a p15a-origin control, were transduced into a dense culture (OD600~0.8) of MG1655 and plated on LB agar plates containing chloramphenicol. As can be seen on FIG. 7, while the p15a-origin control shows healthy colonies up to the last dilution, indicative of active plasmid replication, the samples containing the primase-containing payload show colonies only at high MOIs: since the strain will lose the payload by division, those drops that contained a high number of transduced bacteria will appear as dense spots since division will be halted at high cell densities; as the MOIs are reduced, the spots become more transparent and single colonies are hard to distinguish, indicative of cells that are dying due to plasmid loss and exposure to antibiotics. This is also indicative of a burst of expression of the chloramphenicol acetyltransferase gene upon transduction, which, in the absence of active replication, will get diluted over time; this may cause the receiver cells to survive for a certain amount of time until the intracellular concentration of chloramphenicol acetyltransferase drops below a critical level to support growth in antibiotic-supplemented media.

In conclusion, PICI primase and origin can be stably maintained in production strains, are compatible with lambda-based phagemids packaging judging by the titers obtained and the payloads are dependent on the presence of its cognate primase for active replication and maintenance in target strains.

Example 3

In Vitro Killing of *E. coli* Using a Conditional Origin of Replication

Next, the inventors tested if sequence-specific killing mediated by the Cpf1 nuclease would still occur in cells transduced by packaged phagemids. Since the cells will lose the plasmid by division, it was ignored if the initial burst of expression of the nuclease circuit would still be sufficient to achieve killing at a similar MOI as the one observed with a constitutive origin of replication.

To do this, the inventors constructed a large plasmid (~12 kb) exchanging the p15a-based origin of replication by the primase origin. This plasmid targets the lacZ gene (p1322, SEQ ID NO: 25) and also contains a chloramphenicol marker. Since it was ignored if the RBS strength would need to be modified to replicate a large plasmid, the inventors transformed this plasmid into the production strain s1965 harboring an inducible primase RBS library in trans, as done for the initial, smaller payload. Next day, the inventors observed that the plates contained hundreds of colonies. One of these colonies was picked, sequenced to verify that the payload contained the primase-ori, the RBS of the primase in trans sequenced (SEQ ID NO: 26) and packaged phagemids were produced. As a control, the inventors produced the same phagemid containing a p15a-based origin of replication (p780, SEQ ID NO: 27) from the same production strain.

In this case, since the payload targets the MG1655 strain, the inventors verified the titers of the production in a derivative of MG1655 lacking the lacZ gene (s248) and containing the primase RBS 3 plasmid in trans (p1321).

Titers of both packaged phagemids whose payloads comprise constitutive and conditional origins of replication were undistinguishable, of about $1.5 \times 10^8/\mu L$ after 10× concentration, suggesting that this approach is also valid for larger payloads.

Next, the inventors tested if killing of a target strain with packaged phagemids would be possible in the absence of selection and active replication of the payload, as the inventors already demonstrated with p15a-based origins. To do this, a culture of E. coli MG1655 was grown in LB+CaCl$_2$ to an OD600 of about 0.8 and diluted in LB+CaCl$_2$ to an OD=0.025. The packaged phagemids targeting lacZ and containing the p15a-based origin (control) or the primase origin were serially diluted 3×; this approach allowed for testing different MOIs. 90 µL of cells were added to each well containing a packaged phagemid dilution. After 30 min-incubation at 37° C., 10× dilutions of each reaction were performed, 10 µL plated on LB agar plates and incubated overnight at 37° C.

Figure 8:
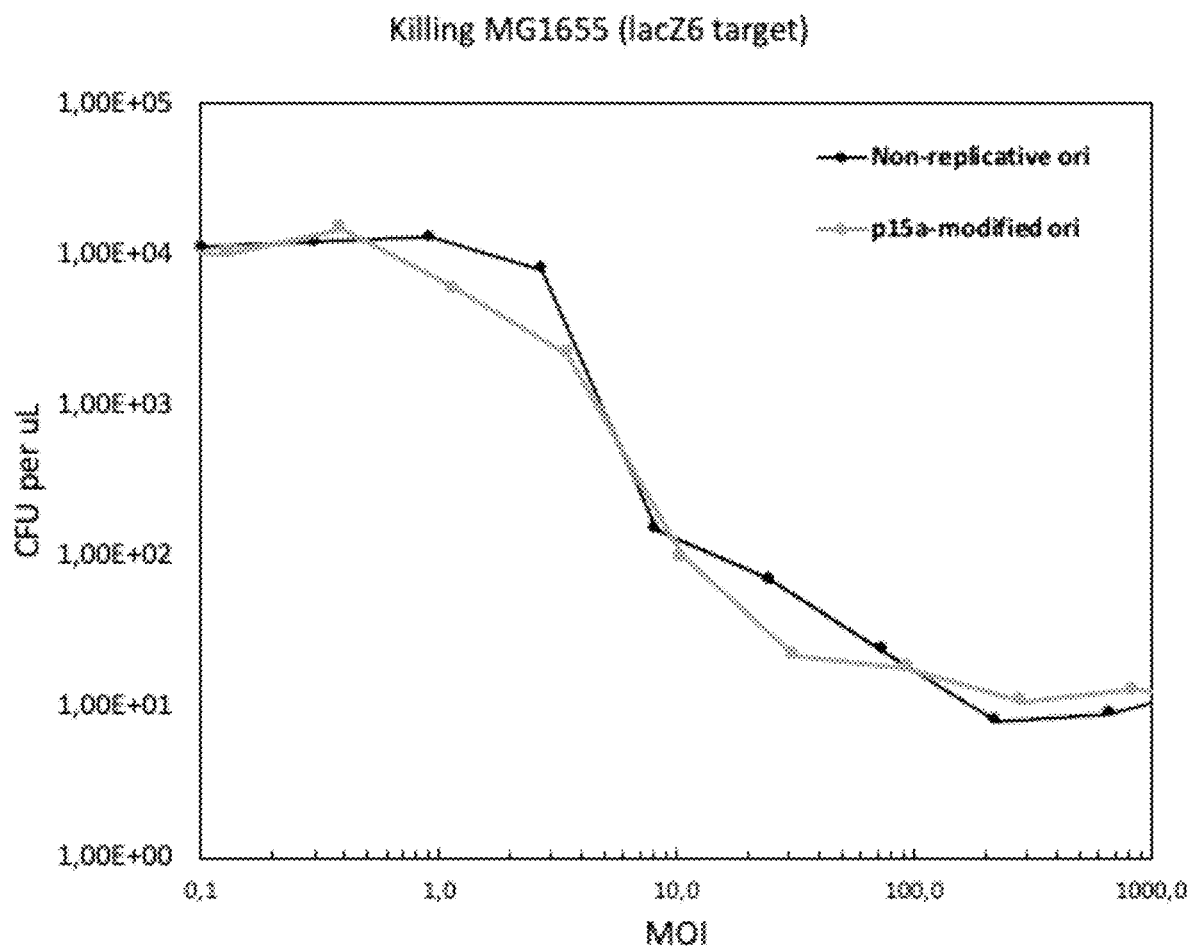
FIG. 8: Comparison of killing activity in the absence of antibiotic selection of *E. coli* MG1655 transduced with a nuclease circuit targeting the lacZ gene. Black line, primase-ori (conditional replication, p1322); grey line, modified p15a-ori, replicative (p780).

As can be seen in FIG. 8, the behavior of the p15a-containing nuclease payload was indistinguishable from the payload containing the primase conditional origin: about 2-log killing at an MOI 10.

In conclusion, conditional origins of replication based on PICIs allow for production at high titers of large payloads (~12 kb) and nuclease-mediated killing of a target strain in the absence of selection and primase protein.

Example 4

Removal of Restriction Sites from Pici-Derived Origins of Replication

Finally, the inventors tested if the PICI origins of replication were amenable to removal of restriction sites present in certain target strains: the presence of such sites may completely abolish nuclease-specific killing since the payload will be degraded in the target strain before the nuclease gene is expressed.

To do this, the inventors analyzed the 282-bp PICI origin and found that it contains the O157 restriction site GAAABCC (GAAAGCC). The inventors modified this site within the origin and obtained the sequence GAAAGCa (small cap represents the mutation introduced) which should not be recognized by O157 strains. The modified PICI origin (SEQ ID NO: 6) was then cloned into ~12 kb payloads containing a Cpf1 nuclease circuit targeting the lacZ gene as mentioned in Example 3 (p1326, SEQ ID NO: 28) and also a quadruplex crRNA guide targeting stx1 and stx2 genes (p1327, SEQ ID NO: 29).

The inventors previously designed a bacterial cell line producing an engineered lambda-based capsid, comprising a chimeric 1A2 gpJ protein and a chimeric STF-V10[Helix], able to inject efficiently in O157 strains (s15816), so these two plasmids were transformed in this production strain containing the primase RBS 3 in trans.

Colonies were readily obtained, which suggested that the mutation introduced in the origin does not affect the ability of the PICI primase to recognize and replicate it. Sequencing results verified the presence of a modified, deltaGAAABCC primase origin of replication.

Packaged phagemids were produced from these two strains and titrated on a variant of MG1655 recognized by this specific packaged phagemid, supplemented with a plasmid encoding the primase RBS variant 3 (s18241).

Figure 9:
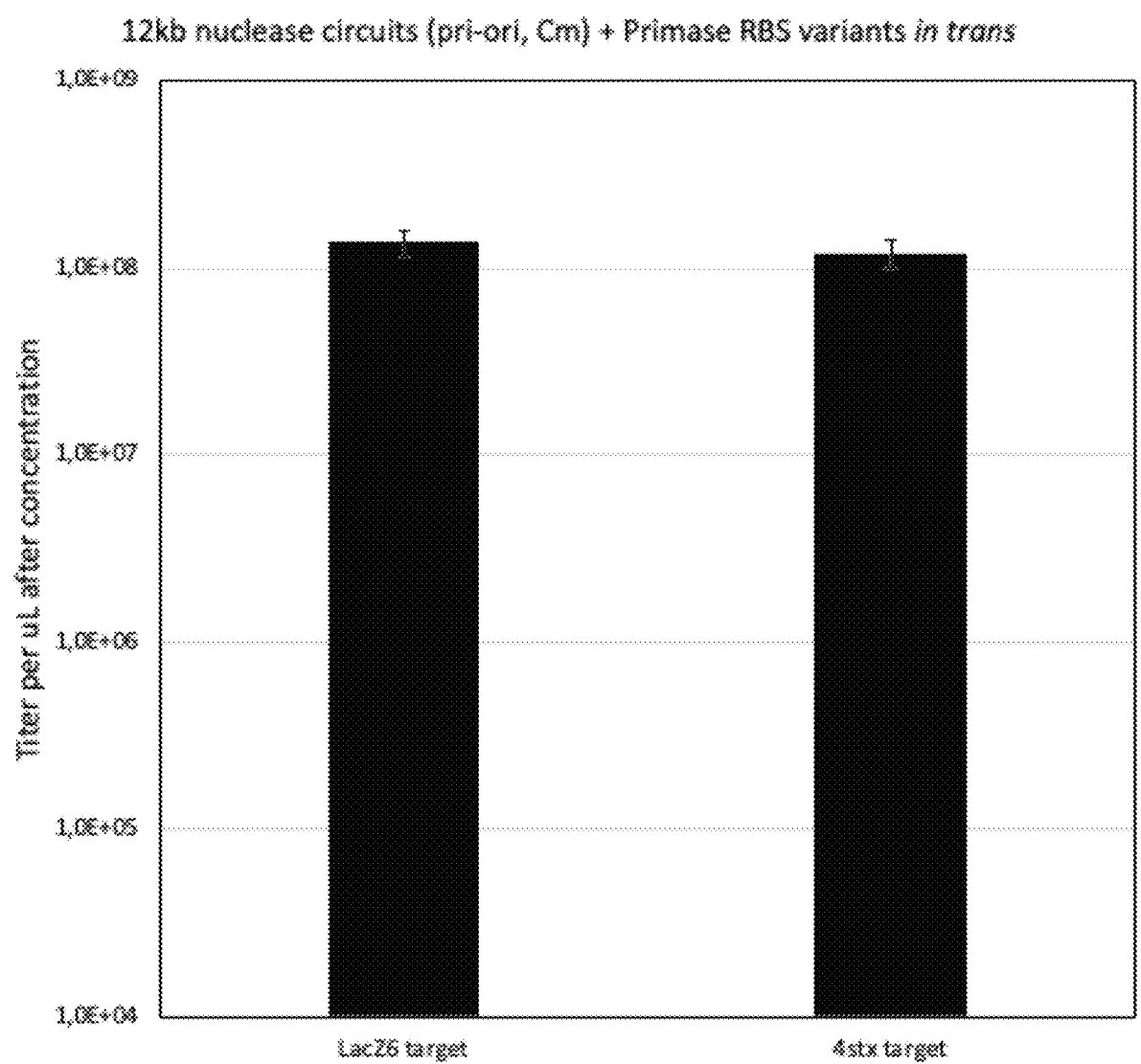
FIG. 9: Packaged phagemids titers obtained with ~12 kb plasmids harboring the mutated primase-ori in production strains containing primase RBS 3. Titers shown are after a 10× concentration. Left bar, lacZ target (p1326); right bar, 4stx target (p1327).

As can be seen on FIG. 9, titers are equivalent with both p15a-containing origins or non-mutated PICI origins (>1× $10^8/\mu L$ after 10× concentration).

Finally, two killing experiments were performed in O157 strains as described above for MG1655:

Killing using the lacZ target in two O157-delta-stx strains (s2185 and s17465). As a control for unspecific killing, packaged phagemids were also transduced into the strain s11983, which is a derivative of the O157 H10dstx strain lacking the lacZ gene.

Killing using the quadruplex crRNA guides targeting stx targets in four wild-type O157 strains (s13861, s13862, s13863, s13864).

Briefly, cell cultures were brought to an OD600=0.025 and packaged phagemids serially diluted 1:3. 90 µL of cell cultures were added to the packaged phagemid dilutions, incubated for 30 min at 37° C., and serial 10× dilutions to allow for cell count were performed. 10 µL of each dilution were then plated on LB agar.

Figure 10:
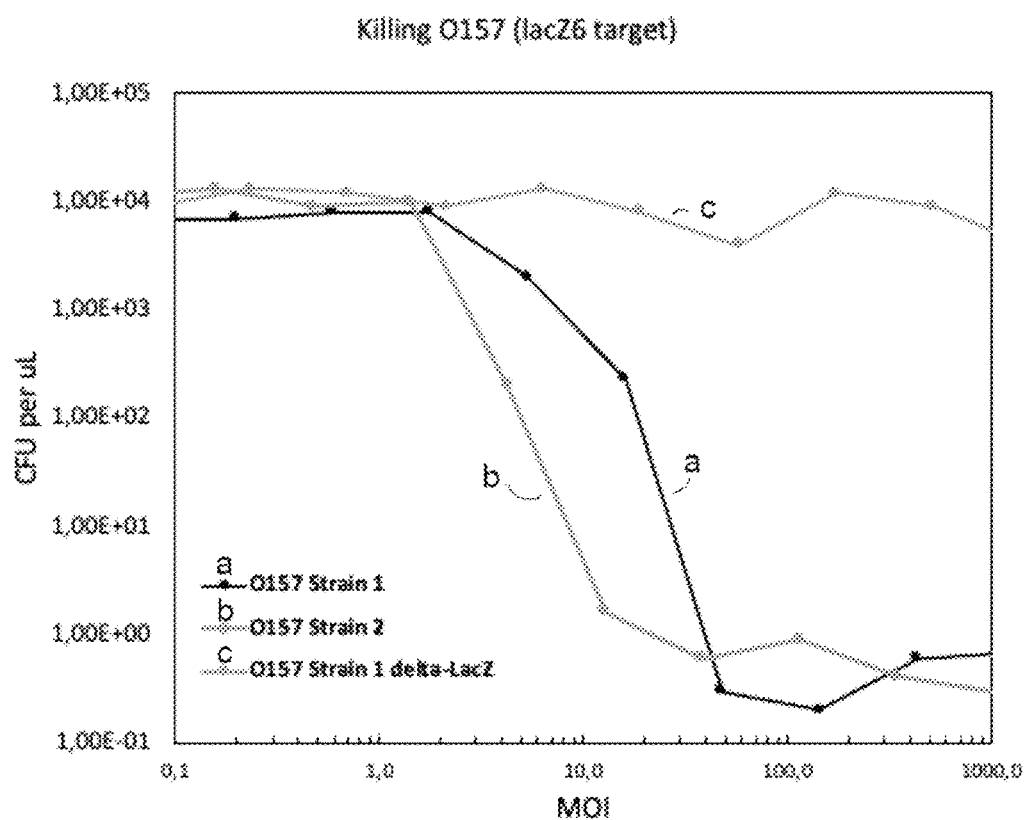
FIG. 10: Nuclease-mediated killing of different O157 strains mediated by targeting lacZ by transduction of packaged phagemids harboring a conditional origin of replication, payload p1326 (grey line c, an O157 strain lacking the lacZ gene serves as a non-killing control).
Figure 11:
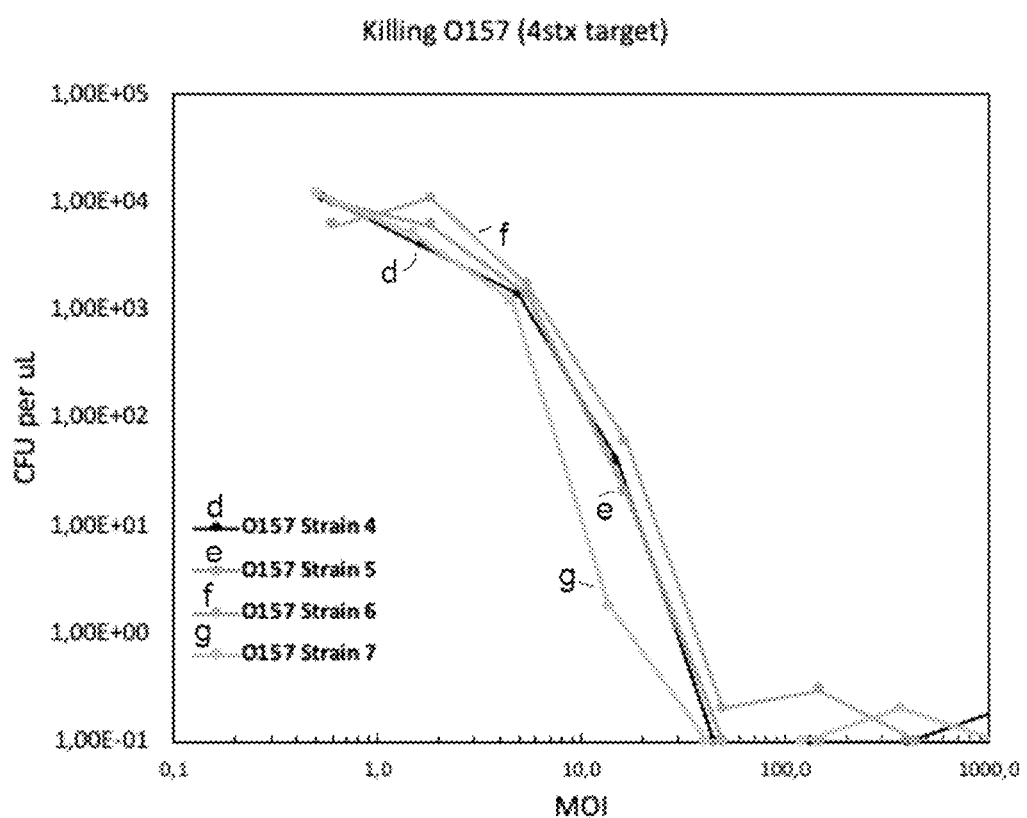
FIG. 11: Nuclease-mediated killing of four O157 strains mediated by stx targeting after transduction of packaged phagemids harboring a conditional origin of replication (payload p1327).

As can be seen on FIGS. 10 and 11, both packaged phagemids targeting lacZ or stx genes are effective and the MOIs needed for killing are equivalent to those obtained with packaged phagemids containing constitutive origins of replication in the absence of antibiotic selection. Strains not containing the target (s11983) are not killed at all, as expected, which suggests there is little to no nonspecific-killing. Additionally, when plated on selection media (LB agar containing chloramphenicol), the non-targeted strain shows a similar profile as that seen for MG1655: dense spots at high MOIs and low dilutions (the cells cannot actively divide due to cell density and cannot lose the plasmid) and weaker density spots, translucid, at lower MOIs and higher dilutions, indicative of cell death due to exposure to the antibiotics.

Example 5

In Vivo Decolonization with a Payload Bearing a Conditional Origin of Replication The present example demonstrates efficient decolonization in vivo by specifically killing bacteria bearing six genes using a packaged phagemid with a conditional origin of replication.

Materials and Methods

Streptomycin-treated mice were orally administered with either a target bacterial strain (hereafter referred to as 'Target strain') or a mutant of the same bacterial strain deleted for a specific gene of interest, namely a stx gene (hereafter referred to as 'Non-Target strain') to establish a durable intestinal colonization with these bacterial strains.

A plasmid of sequence SEQ ID NO: 10, carrying a conditional origin of replication of sequence SEQ ID NO: 7, and coding for a nuclease and its guide targeting the stx gene mentioned above, was packaged into an engineered lambda-based capsid, comprising a chimeric 1A2 gpJ protein and a chimeric STF-V10[Helix] (1A2-V10 packaged phagemid).

Mice colonized with either strain were given 100 μl of packaged phagemids (approximately $10^{12}$ particles) along with 100 μl of a buffer (sucrose and bicarbonate in water) aimed at temporarily neutralizing the gastric pH. A separate group of mice colonized with the Target strain received only the buffer, to account for natural changes in colonization levels over the time of the experiment.

The bacterial colonization levels were measured non-invasively by plating dilutions of stool recovered from each animal individually onto agar plates.

Figure 12:
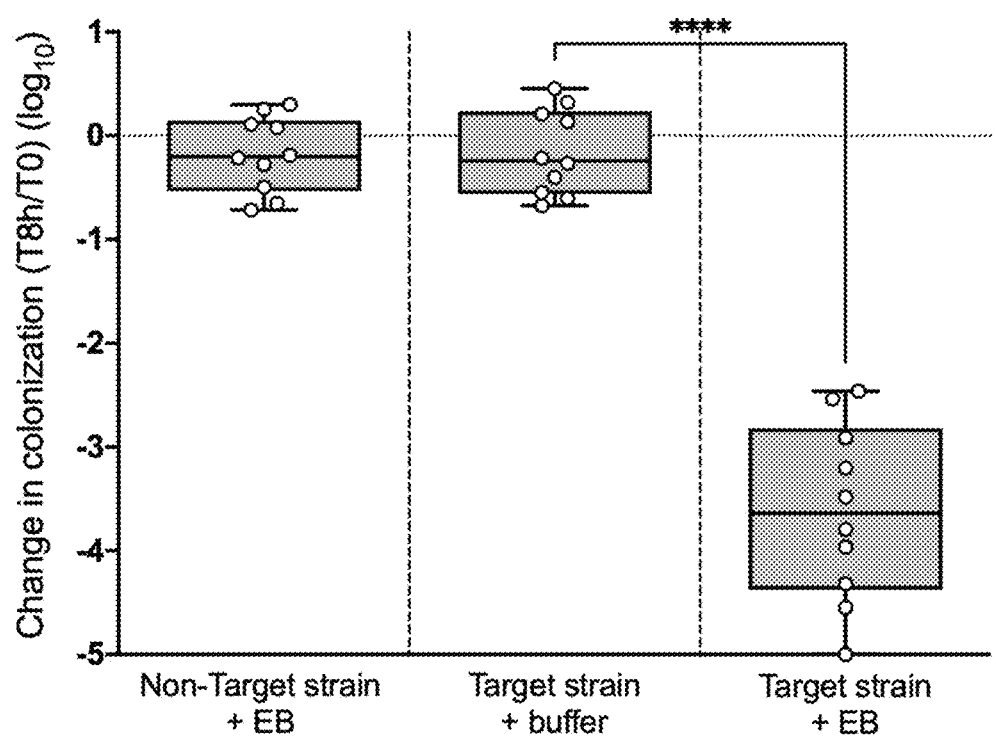
FIG. 12: Change in colonization in colonized mice orally administered with either a neutralizing buffer alone ('+buffer') or $10^{12}$ particles of packaged phagemids in a neutralizing buffer ('+EB'). Change in colonization between T0 and T8h is reported for each animal, and the median and quartiles of each experimental group were graphed. ****$p<0.0001$ by unpaired t test.

These levels were compared before treatment was initiated (termed 'T0') and 8 hours after the treatment (termed 'T8h'), and the change in colonization between T8h and T0 was calculated for each animal, and expressed as logarithmic change (see FIG. 12).

Results

The pH-neutralizing buffer alone had no effect on the Target strain colonization levels, whereas the packaged phagemids caused a 3.5-log reduction in bacterial burden recovered from the stool 8 hours after oral administration. As expected, the packaged phagemids had no effect on colonization levels of the Non-target strain, demonstrating the specificity of packaged phagemids towards their target sequence.

These results thus demonstrate that an efficient in vivo killing of targeted bacteria can be achieved by delivering in said targeted bacteria, packaged phagemids with a conditional origin of replication, which is not active in the targeted bacteria, said phagemids being this incapable to replicate in said targeted bacteria.

Example 6

Adenine Base Editing of β-Lactamase on the *E. coli* Genome after Phagemid Transduction In Vitro Using a Payload with a Conditional Origin of Replication This example presents a method for the base editing of the nucleic acid sequence encoding®-lactamase (SEQ ID NO: 30) on the *E. coli* MG1655 genome after phagemid transduction in vitro using a payload comprising a conditional origin of replication of sequence SEQ ID NO: 7, based on a primase-helicase.

The non-replicative payload comprises an adenine base editor (ABE8e), a transcribed guideRNA targeting the active site of the p-lactamase gene (K71E) on the genome, a lambda packaging sequence, a chloramphenicol resistance marker, and the conditional origin of replication of sequence SEQ ID NO: 7. Production of lambda phagemids, packaged inside a bacterial delivery vehicle comprising an A8 gpJ protein and an EB6 STF protein for delivery into *E. coli* MG1655, resulted in titers of $6.7 \times 10^6$ transduction units per μl (tu/μl).

Transduced cells were plated on LB plates 2 hours post transduction at different multiplicity of infections (MOI). The next day, 96 individual colonies for each MOI were spotted on LB and LB (carbenicillin) plates in order to analyse the base editing efficiency.

Figure 13:
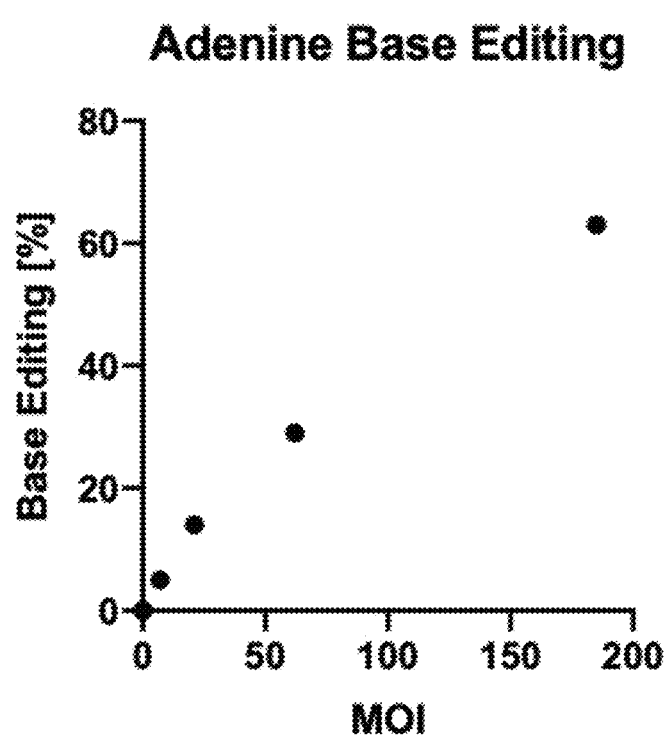
FIG. 13: Adenine base editing of β-lactamase on the *E. coli* genome after phagemid transduction in vitro using a payload comprising a conditional origin of replication of sequence SEQ ID NO: 7. 96 individual colonies for each MOI were spotted on LB and LB (carbenicillin) plates and base editing efficiencies were calculated.

As shown on FIG. 13, the efficiency of adenine base editing targeting the active site of the β-lactamase gene (K71E) on the genome was multiplicity of infection (MOI)-dependent. A base editing efficiency of ~63% of the bacterial population was obtained at high MOIs using the payload comprising a conditional origin of replication.

The invention claimed is:

1. A nucleic acid vector encoding a programmable nuclease, wherein said programmable nuclease kills a targeted receiver bacterial cell,
wherein said vector is a phagemid or recombinant phage nucleic acid vector, said vector comprising a conditional origin of replication which is inactive in the targeted receiver bacterial cell but is active in a donor bacterial cell, wherein said conditional origin of replication is SEQ ID NO: 4 which is the origin of replication from the phage-inducible chromosomal island (PICI) of the *Escherichia coli* strain CFT073, or said origin of replication is modified to be the sequence of SEQ ID NO: 6 or SEQ ID NO: 7, and wherein said conditional origin of replication is active in said donor bacterial cell because said donor bacterial cell expresses a primase-helicase comprising SEQ ID NO: 8 and wherein said vector is devoid of antibiotic resistance marker.

2. The nucleic acid vector of claim 1, wherein the nuclease is selected from the group consisting of Cpf1 nuclease, Cas9 nuclease, Mad4 nuclease, Mad7 nuclease, and Cms1 nuclease.

3. The nucleic acid vector of claim 1, wherein the nuclease is Cpf1 nuclease.

4. The nucleic acid vector of claim 1, wherein the nuclease is Cas9 nuclease.

5. The nucleic acid vector of claim 1, wherein the nuclease is Mad4 nuclease.

6. The nucleic acid vector of claim 1, wherein the nuclease is Mad7 nuclease.

7. The nucleic acid vector of claim 1, wherein the nuclease is Cms1 nuclease.

8. A bacterial delivery vehicle comprising the vector according to claim 1.

* * * * *